(12) United States Patent
Chandrasekaran et al.

(10) Patent No.: US 8,529,889 B2
(45) Date of Patent: Sep. 10, 2013

(54) METHODS AND COMPOSITIONS RELATED TO THE MODULATION OF INTERCELLULAR JUNCTIONS

(75) Inventors: Aarthi Chandrasekaran, Cambridge, MA (US); Shiladitya Sengupta, Waltham, MA (US); David A. Berry, Brookline, MA (US); Kristine Holley, Boston, MA (US); Ganlin Zhao, Arlington, MA (US); Ram Sasisekharan, Bedford, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/171,490

(22) Filed: Jun. 29, 2005

(65) Prior Publication Data

US 2006/0067927 A1 Mar. 30, 2006

Related U.S. Application Data

(60) Provisional application No. 60/584,438, filed on Jun. 29, 2004.

(51) Int. Cl.
*A61K 38/47* (2006.01)

(52) U.S. Cl.
USPC ........................... 424/94.61; 514/54; 514/56

(58) Field of Classification Search
None
See application file for complete search history.

(56) References Cited

U.S. PATENT DOCUMENTS

| | | | |
|---|---|---|---|
| 5,338,677 A | 8/1994 | Zimmermann et al. | |
| 5,411,733 A * | 5/1995 | Hozumi et al. ............... | 424/727 |
| 6,217,863 B1 | 4/2001 | Godavarti et al. | |
| 6,252,045 B1 | 6/2001 | Anderson et al. | |
| 6,312,686 B1 | 11/2001 | Staddon et al. | |
| 6,597,996 B1 | 7/2003 | Venkataraman et al. | |
| 6,610,653 B1 | 8/2003 | Bäckström et al. | |
| 6,686,341 B1 | 2/2004 | Bijlsma et al. | |
| 6,723,700 B1 | 4/2004 | Blaschuk et al. | |
| 6,869,789 B2 | 3/2005 | Liu et al. | |
| 6,962,699 B2 | 11/2005 | Pojasek et al. | |
| 7,056,504 B1 | 6/2006 | Sasisekharan et al. | |
| 7,083,937 B2 | 8/2006 | Sasisekharan et al. | |
| 7,105,334 B2 | 9/2006 | Pojasek et al. | |
| 7,110,889 B2 | 9/2006 | Venkataraman et al. | |
| 7,117,100 B2 | 10/2006 | Venkataraman et al. | |
| 7,129,335 B2 | 10/2006 | Pojasek et al. | |
| 7,139,666 B2 | 11/2006 | Venkataraman | |
| 7,247,445 B2 | 7/2007 | Sasisekharan et al. | |
| 7,270,815 B2 | 9/2007 | Sasisekharan et al. | |
| 7,390,633 B2 | 6/2008 | Liu et al. | |
| 7,396,824 B2 | 7/2008 | Sasisekharan et al. | |
| 7,399,604 B2 | 7/2008 | Sasisekharan et al. | |
| 7,412,332 B1 | 8/2008 | Venkataraman et al. | |
| 7,429,474 B2 | 9/2008 | Sasisekharan et al. | |
| 7,455,986 B2 | 11/2008 | Liu et al. | |
| 7,504,247 B2 | 3/2009 | Sasisekharan et al. | |
| 7,507,570 B2 | 3/2009 | Prabhakar et al. | |
| 7,508,206 B2 | 3/2009 | Sasisekharan et al. | |
| 7,553,950 B2 | 6/2009 | Prabhakar et al. | |
| 7,560,106 B2 | 7/2009 | Sasisekharan et al. | |
| 7,560,444 B2 * | 7/2009 | Richardson et al. ............ | 514/56 |
| 7,585,642 B2 | 9/2009 | Sasisekharan et al. | |
| 7,592,152 B2 | 9/2009 | Prabhakar et al. | |
| 7,662,604 B2 | 2/2010 | Prabhakar et al. | |
| 7,687,479 B2 | 3/2010 | Sasisekharan et al. | |
| 7,695,711 B2 | 4/2010 | Myette et al. | |
| 7,709,461 B2 | 5/2010 | Liu et al. | |
| 7,728,589 B2 | 6/2010 | Sasisekharan et al. | |
| 7,737,692 B2 | 6/2010 | Sasisekharan et al. | |
| 2002/0122793 A1 * | 9/2002 | Liu et al. .................... | 424/94.61 |
| 2002/0128225 A1 | 9/2002 | Liu et al. | |
| 2002/0169143 A1 | 11/2002 | Sasisekharan et al. | |
| 2003/0008820 A1 | 1/2003 | Kwan et al. | |
| 2003/0099628 A1 | 5/2003 | Liu et al. | |
| 2003/0105165 A1 * | 6/2003 | Griffith ........................ | 514/651 |
| 2003/0191587 A1 | 10/2003 | Venkataraman et al. | |
| 2004/0091471 A1 | 5/2004 | Myette et al. | |
| 2004/0091472 A1 | 5/2004 | Pojasek et al. | |
| 2004/0092037 A1 | 5/2004 | Sasisekharan et al. | |
| 2004/0197933 A1 | 10/2004 | Venkataraman et al. | |
| 2004/0204869 A1 | 10/2004 | Venkataraman et al. | |
| 2005/0037376 A1 | 2/2005 | Sasisekharan et al. | |
| 2005/0214276 A9 | 9/2005 | Myette et al. | |
| 2005/0227320 A1 | 10/2005 | Pojasek et al. | |
| 2005/0233402 A1 | 10/2005 | Liu et al. | |

(Continued)

FOREIGN PATENT DOCUMENTS

| WO | WO 91/04745 A1 | 4/1991 |
|---|---|---|
| WO | WO 96/37196 A1 | 11/1996 |

(Continued)

OTHER PUBLICATIONS

Dull et al., Am J Physiology Lung Cell Molecular Physiology, May 2003, vol. 285, L986-L995.*
Thanou et al., Advanced drug delivery Reviews, 2001, vol. 52, p. 117-1260.*
Banks et al., Journal of Cell Science, 1998, vol. 111, p. 533-540.*
Bendayan et al., Microscopy Research and Technique, 2002, vol. 57, p. 365-380.*
Hamai et al., The Journal of Biological Chemistry, 1997, vol. 272, No. 14, p. 9123-9130.*
McGrath et al., J Pathol, 1997, vol. 183, p. 251-252.*
Krautheim et al., Clin Pharamcokinet, 2003, vol. 42, No. 14, p. 1287-1304.*
Pickles et al., Journal of Virology, 2000, vol. 74, No. 13, p. 6050-6057.*

(Continued)

*Primary Examiner* — Kade Ariani
(74) *Attorney, Agent, or Firm* — Wolf, Greenfield & Sacks, P.C.

(57) ABSTRACT

The invention relates to compositions and methods for the modulation of the permeability of the epithelial cell barrier complex. In particular, the invention provides compositions and methods for using polysaccharides, preferably glycosaminoglycans, and agents that modify cell surface glycosaminoglycans, preferably glycosaminoglycan-degrading enzymes to modulate intercellular junctions. The compositions and methods provided can be used to facilitate the delivery of biologically active molecules.

15 Claims, 11 Drawing Sheets

(56) References Cited

U.S. PATENT DOCUMENTS

| | | |
|---|---|---|
| 2005/0233419 A1 | 10/2005 | Pojasek et al. |
| 2006/0024664 A1 | 2/2006 | Sasisekharan et al. |
| 2006/0057638 A1 | 3/2006 | Bosques et al. |
| 2006/0067927 A1 | 3/2006 | Chandrasekaran et al. |
| 2006/0067928 A1 | 3/2006 | Liu et al. |
| 2006/0078959 A1 | 4/2006 | Prabhakar et al. |
| 2006/0083711 A1 | 4/2006 | Berry et al. |
| 2006/0105430 A1 | 5/2006 | Sasisekharan et al. |
| 2006/0127950 A1 | 6/2006 | Bosques et al. |
| 2006/0154894 A1 | 7/2006 | Berry et al. |
| 2006/0177885 A1 | 8/2006 | Myette et al. |
| 2006/0177910 A1 | 8/2006 | Myette et al. |
| 2006/0177911 A1 | 8/2006 | Myette et al. |
| 2006/0182734 A1 | 8/2006 | Liu et al. |
| 2006/0183713 A1 | 8/2006 | Liu et al. |
| 2006/0183891 A1 | 8/2006 | Myette et al. |
| 2006/0292130 A1 | 12/2006 | Sasisekharan et al. |
| 2006/0292655 A1 | 12/2006 | Sasisekharan et al. |
| 2006/0292673 A1 | 12/2006 | Sasisekharan et al. |
| 2007/0004012 A1 | 1/2007 | Sasisekharan et al. |
| 2007/0020243 A1 | 1/2007 | Sengupta et al. |
| 2007/0065424 A1 | 3/2007 | Pojasek et al. |
| 2007/0065921 A1 | 3/2007 | Sasisekharan et al. |
| 2007/0066769 A1 | 3/2007 | Venkataraman et al. |
| 2007/0148157 A1 | 6/2007 | Prabhakar et al. |
| 2007/0148158 A1 | 6/2007 | Sasisekharan et al. |
| 2007/0148740 A1 | 6/2007 | Prabhakar et al. |
| 2007/0161073 A1 | 7/2007 | Sasisekharan et al. |
| 2007/0202563 A1 | 8/2007 | Prabhakar et al. |
| 2007/0224670 A1 | 9/2007 | Prabhakar et al. |
| 2008/0071148 A1 | 3/2008 | Bosques et al. |
| 2008/0278164 A1 | 11/2008 | Sasisekharan et al. |
| 2008/0301178 A1 | 12/2008 | Venkataraman et al. |
| 2009/0045811 A1 | 2/2009 | Sasisekharan et al. |
| 2009/0081635 A1 | 3/2009 | Liu et al. |
| 2009/0105463 A1 | 4/2009 | Berry et al. |
| 2009/0119027 A1 | 5/2009 | Venkataraman et al. |
| 2009/0156477 A1 | 6/2009 | Berry et al. |
| 2009/0269326 A1 | 10/2009 | Myette et al. |
| 2010/0062468 A1 | 3/2010 | Sasisekharan et al. |
| 2010/0119494 A1 | 5/2010 | Sengupta et al. |
| 2010/0129868 A1 | 5/2010 | Myette et al. |

FOREIGN PATENT DOCUMENTS

| | | |
|---|---|---|
| WO | WO 97/16556 A1 | 5/1997 |
| WO | WO 98/14186 A1 | 4/1998 |
| WO | WO 98/30211 A1 | 7/1998 |
| WO | WO 98/37096 A1 | 8/1998 |
| WO | WO 99/15649 A2 | 4/1999 |
| WO | WO 00/12726 A2 | 3/2000 |
| WO | WO 00/65521 A2 | 11/2000 |
| WO | WO 01/66772 A2 | 9/2001 |
| WO | WO 02/23190 A2 | 3/2002 |
| WO | WO 02/3240 A2 | 4/2002 |
| WO | WO 02/077199 A2 | 10/2002 |
| WO | WO 03/098991 A2 | 12/2003 |
| WO | WO 03/102160 A3 | 12/2003 |
| WO | WO 2004/055491 A2 | 7/2004 |
| WO | WO 2004/062592 A2 | 7/2004 |
| WO | WO 2004/069152 A2 | 8/2004 |
| WO | WO 2005/087920 A2 | 9/2005 |
| WO | WO 2005/110438 A2 | 11/2005 |
| WO | WO 2005/111627 A2 | 11/2005 |
| WO | WO 2006/076627 A2 | 7/2006 |
| WO | WO 2006/083328 A2 | 8/2006 |
| WO | WO 2006/088491 A2 | 8/2006 |
| WO | WO 2006/089206 A2 | 8/2006 |
| WO | WO 2006/105313 A2 | 10/2006 |
| WO | WO 2006/105315 A2 | 10/2006 |
| WO | WO 2007/044471 A2 | 4/2007 |
| WO | WO 2007/120478 A2 | 10/2007 |

OTHER PUBLICATIONS

Yang et al., Pharmaceutical Research, 2004, vol. 21, No. 7, p. 1127-1136.*

Boyle et al., Parts plus pipes: Synthetic Biology Approaches to Metabolic Engineering. Metab. Eng. 2011;1-10.

Kramer et al., Semi-synthetic mammalian gene regulatory networks. Metab. Eng. 2005; 7:241-50.

Pickles et al., Retargeting the Coxsackievirus and Adenovirus Receptor to the Apical Surface of Polarized Epithelial Cells Reveals the Glycocalyx as a Barrier to Adenovirus-Mediated Gene Transfer. J. of Virology Jul. 2000; 74(13):6050-57.

Weber et al., A novel hybrid dual-channel catalytic-biological sensor system for assessment of fruit quality. J. Biotechnology 2009; 139:314-17.

Weber et al., A biotin-triggered genetic switch in mammalian cells and mice. Metab. Eng. 2009; 11:117-24.

Yang et al., Cyclodextrins in Nasal Delivery of Low-Molecular-Weight Heparins: In vivo and in Vitro Studies. Pharmaceutical Research Jul. 2000 ; 21(7):1127-36.

Arribas et al., Diverse cell surface protein ectodomains are shed by a system sensitive to metalloprotease inhibitors. J Biol Chem. May 10, 1996;271(19):11376-82.

Asundi et al., Matrix metalloproteinase-dependent shedding of syndecan-3, a transmembrane heparan sulfate proteoglycan, in Schwann cells. J Neurosci Res. Sep. 1, 2003;73(5):593-602.

Atkinson et al., Role of protein tyrosine phosphorylation in acetaldehyde-induced disruption of epithelial tight junctions. Am J Physiol Gastrointest Liver Physiol. Jun. 2001;280(6):G1280-8.

Beauvais et al., Syndecan-1-mediated cell spreading requires signaling by alphavbeta3 integrins in human breast carcinoma cells. Exp Cell Res. Jun. 10, 2003;286(2):219-32.

Beauvais et al., Syndecans in tumor cell adhesion and signaling. Reprod Biol Endocrinol. Jan. 7, 2004;2:3.

Bernfield et al., Functions of cell surface heparan sulfate proteoglycans. Annu Rev Biochem. 1999;68:729-77.

Endo et al., Cleavage of syndecan-1 by membrane type matrix metalloproteinase-I stimulates cell migration. J Biol Chem. Oct. 17, 2003;278(42):40764-70. Epub Aug. 6, 2003.

Fitzgerald et al., Shedding of syndecan-1 and -4 ectodomains is regulated by multiple signaling pathways and mediated by a TIMP-3-sensitive metalloproteinase. J Cell Biol. Feb. 21, 2000;148(4):811-24.

Godavarti et al., A comparative analysis of the primary sequences and characteristics of heparinases I, II, and III from *Flavobacterium heparinum*. Biochem Biophys Res Commun. Dec. 24, 1996;229(3):770-7.

Godavarti et al., Heparinase I from *Flavobacterium heparinum*. Role of positive charge in enzymatic activity. J Biol Chem. Jan. 2, 1998;273(1):248-55.

Godavarti et al., Heparinase III from *Flavobacterium heparinum*: cloning and recombinant expression in *Escherichia coli*. Biochem Biophys Res Commun. Aug. 23, 1996;225(3):751-8.

González-Mariscal et al., Tight junction proteins. Prog Biophys Mol Biol. Jan. 2003;81(1):1-44.

Goodenough, Plugging the leaks. Proc Natl Acad Sci U S A. Jan. 19, 1999;96(2):319-21.

Harhaj et al., Regulation of tight junctions and loss of barrier function in pathophysiology. Intl J Biochem Cell Biol. 2004;36(7):1206-37.

Hooper et al., Membrane protein secretases. Biochem J. Jan. 15, 1997;321 ( Pt 2):265-79.

Itoh et al., Involvement of ZO-1 in cadherin-based cell adhesion through its direct binding to alpha catenin and actin filaments. J Cell Biol. Jul. 14, 1997;138(1):181-92.

Kiessling et al., Transforming the cell surface through proteolysis. Chem Biol. Mar. 1998;5(3):R49-62.

Knipp et al., Paracellular diffusion in Caco-2 cell monolayers: effect of perturbation on the transport of hydrophilic compounds that vary in charge and size. J Pharm Sci. Oct. 1997;86(10): 1105-10.

Lin et al., Antithrombin binding of low molecular weight heparins and inhibition of factor Xa. Biochim Biophys Acta. Apr. 3, 2001;1526(1):105-13.

Madara, Structural basis for physiological regulation of paracellular pathways in intestinal epithelia. J Membr Biol. 1987;100(2):149-64.

Majerus et al., Anticoagulant, thrombolylic, and antiplatelet drugs. In: Hardman et al., (eds.). Goodman & Gilman's The Pharmacological Bases of Therapeutics, 9th Ed. New York: McGraw Hill, 1996:1341-6.

Matter et al., Signalling to and from tight junctions. Nat Rev Mol Cell Biol. Mar. 2003;4(3):225-36.

Merlos-Suárez et al., Mechanisms controlling the shedding of transmembrane molecules. Biochem Soc Trans. Feb. 1999;27(2):243-6.

Park et al., Exploitation of syndecan-1 shedding by *Pseudomonas aeruginosa* enhances virulence. Nature. May 3, 2001;411(6833):98-102.

Park et al., Syndecan-1 shedding is enhanced by LasA, a secreted virulence factor of *Pseudomonas aeruginosa*. J Biol Chem. Feb. 4, 2000;275(5):3057-64.

Perrimon et al., Specificities of heparan sulphate proteoglycans in developmental processes. Nature. Apr. 13, 2000;404(6779):725-8.

Qi et al., Delivery of therapeutic levels of heparin and low-molecular-weight heparin through a pulmonary route. Proc Natl Acad Sci U S A. Jun. 29, 2004;101(26):9867-72.

Rhodes et al., Chondroitin sulphate proteoglycans: preventing plasticity or protecting the CNS? J Anat. Jan. 2004;204(1):33-48.

Rosenberg et al., Heparan sulfate proteoglycans of the cardiovascular system. Specific structures emerge but how is synthesis regulated? J Clin Invest. Dec. 1, 1997;100(11 Suppl):S67-75.

Sasisekharan et al., Heparin and heparin sulfate: biosynthesis, structure and function. Curr Opin Chem Biol. Dec. 2000;4(6):626-31.

Schlöndorff et al., Metalloprotease-disintegrins: modular proteins capable of promoting cell-cell interactions and triggering signals by protein-ectodomain shedding. J Cell Sci. Nov. 1999;112 ( Pt 21):3603-17.

Simon, What are the drug treatments for inflammatory bowel disease? Ulcerative Colitis: Inflammatory Bowel Disease—UMMC. Dec. 31, 2002. 6 pages.

Subramanian et al., Regulated shedding of syndecan-1 and -4 ectodomains by thrombin and growth factor receptor activation. J Biol Chem. Jun. 6, 1997;272(23):14713-20.

Sugahara et al., Heparin and heparan sulfate biosynthesis. IUBMB Life. Oct. 2002;54(4):163-75.

Tsukita et al., Multifunctional strands in tight junctions. Nat Rev Mol Cell Biol. Apr. 2001;2(4):285-93.

Turner et al., Role for ADAM-family proteinases as membrane protein secretases. Biochem Soc Trans. Feb. 1999 ;27(2):255-9.

Venkataraman et al., Fibroblast growth factors 1 and 2 are distinct in oligomerization in the presence of heparin-like glycosaminoglycans. Proc Natl Acad Sci U S A. Mar. 2, 1999;96(5):1892-7.

Venkataraman et al., Sequencing complex polysaccharides. Science. Oct. 5, 1999;286(5439):537-42.

Wan et al., Der p 1 facilitates transepithelial allergen delivery by disruption of tight junctions. J Clin Invest. Jul. 1999;104(1):123-33.

Willott et al., The tight junction protein ZO-1 is homologous to the *Drosophila* discs-large tumor suppressor protein of septate junctions. Proc Natl Acad Sci U S A. Aug. 15, 1993;90(16):7834-8.

\* cited by examiner

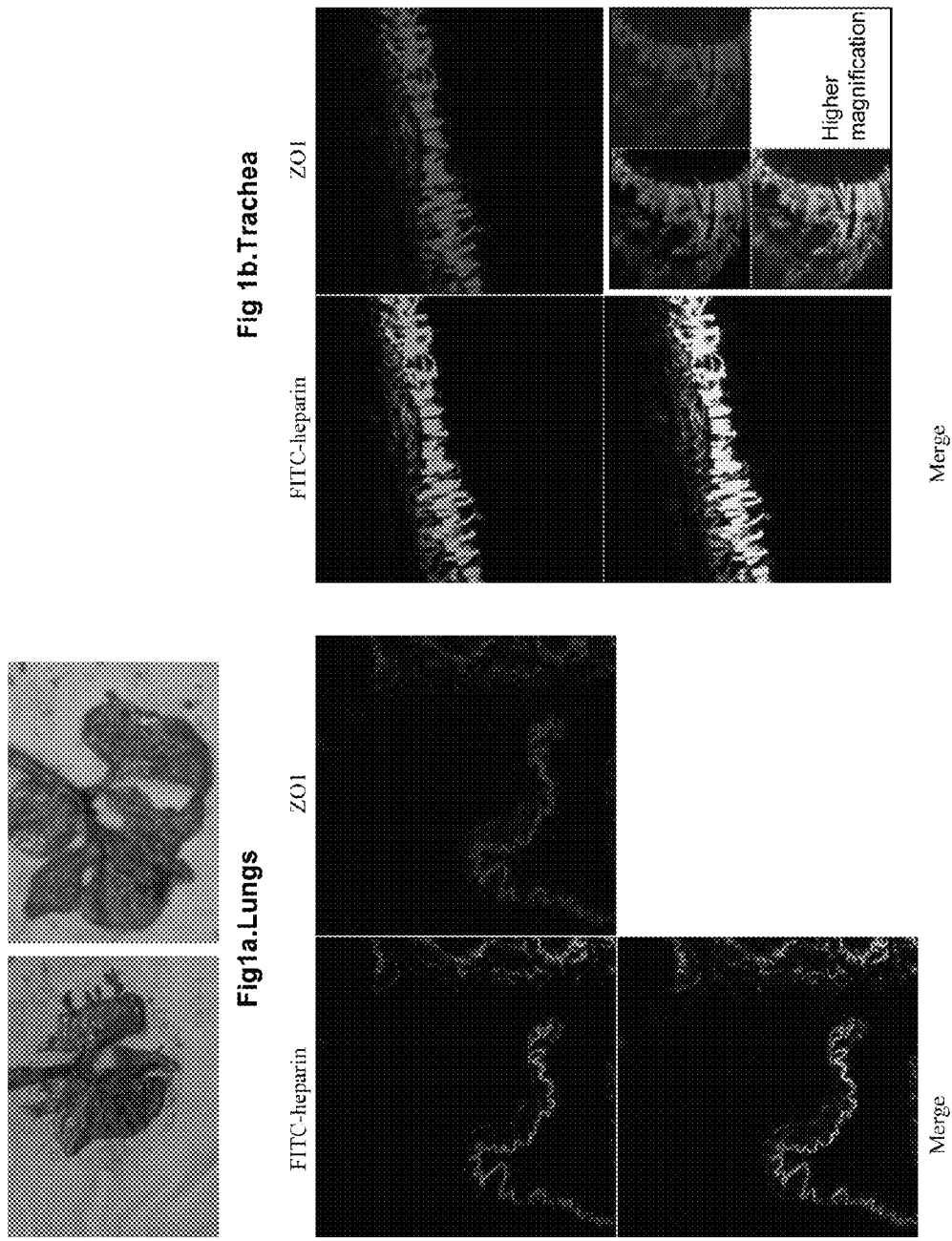
Figure 1: Uptake of heparin into lungs and trachea

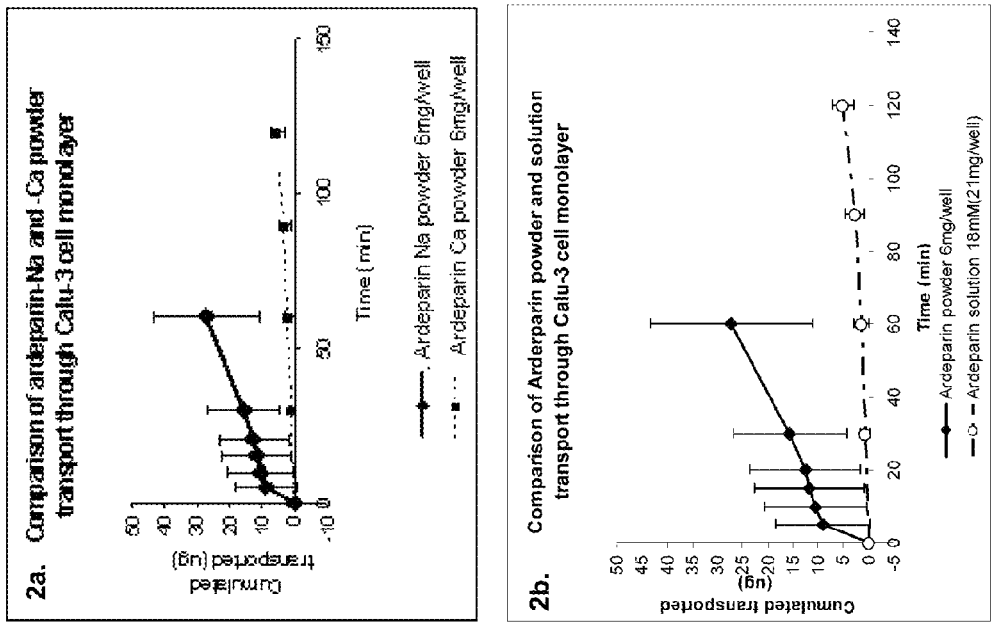
Figure 2: Transport of ardeparin powder through calu-3 epithelial cells

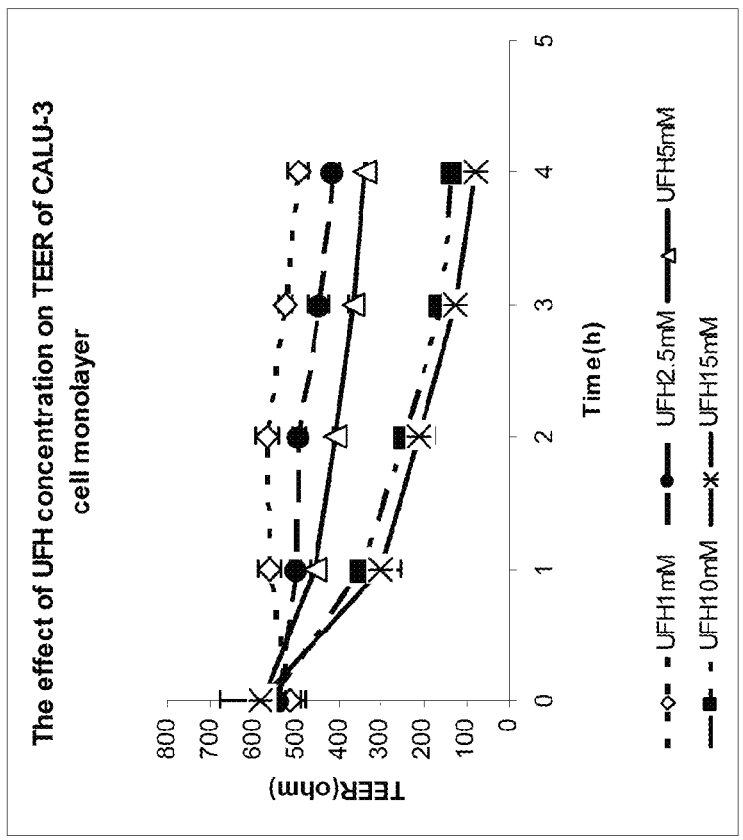
Figure 3: Effect of UFH on TEER of calu3 epithelial cells

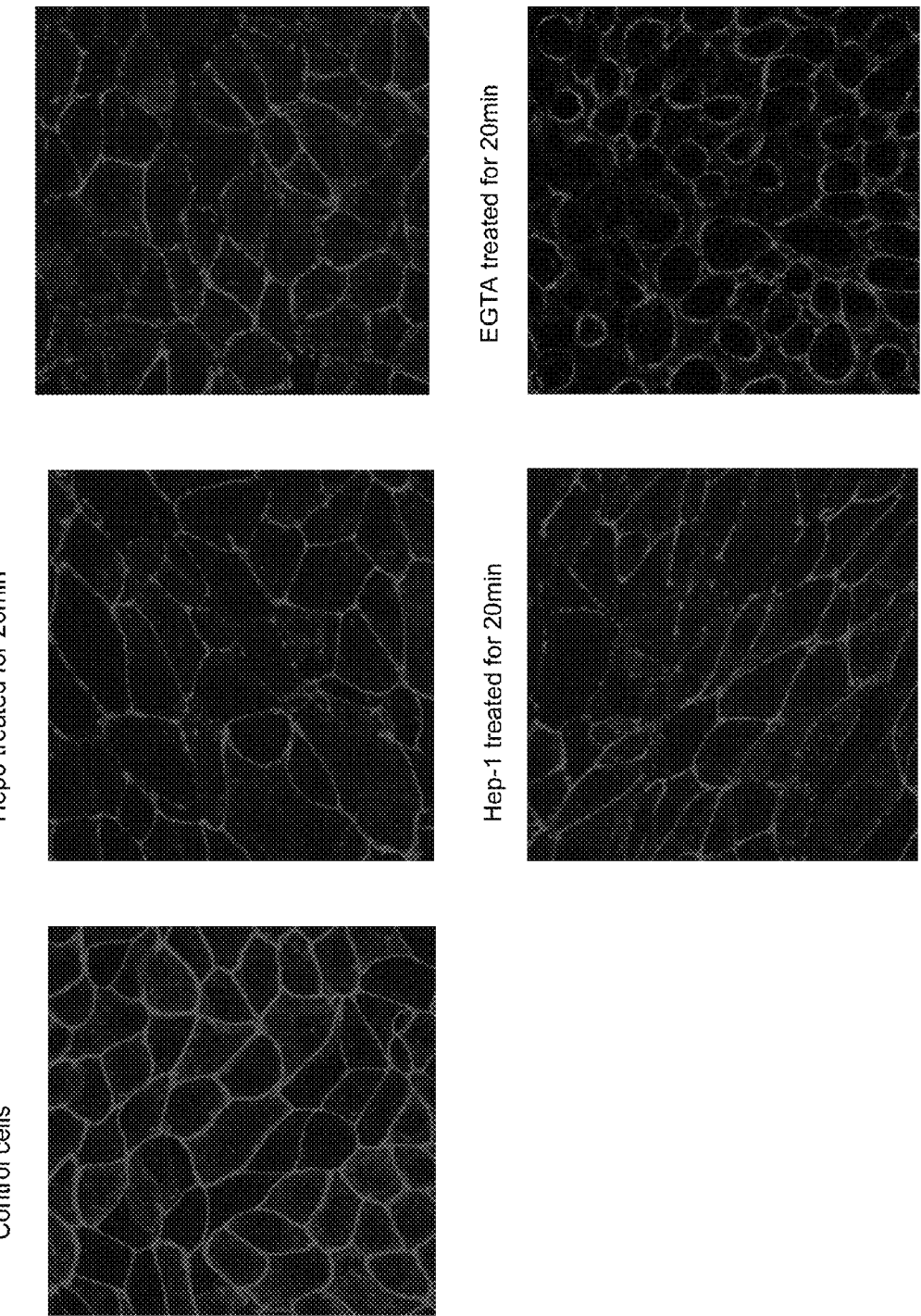

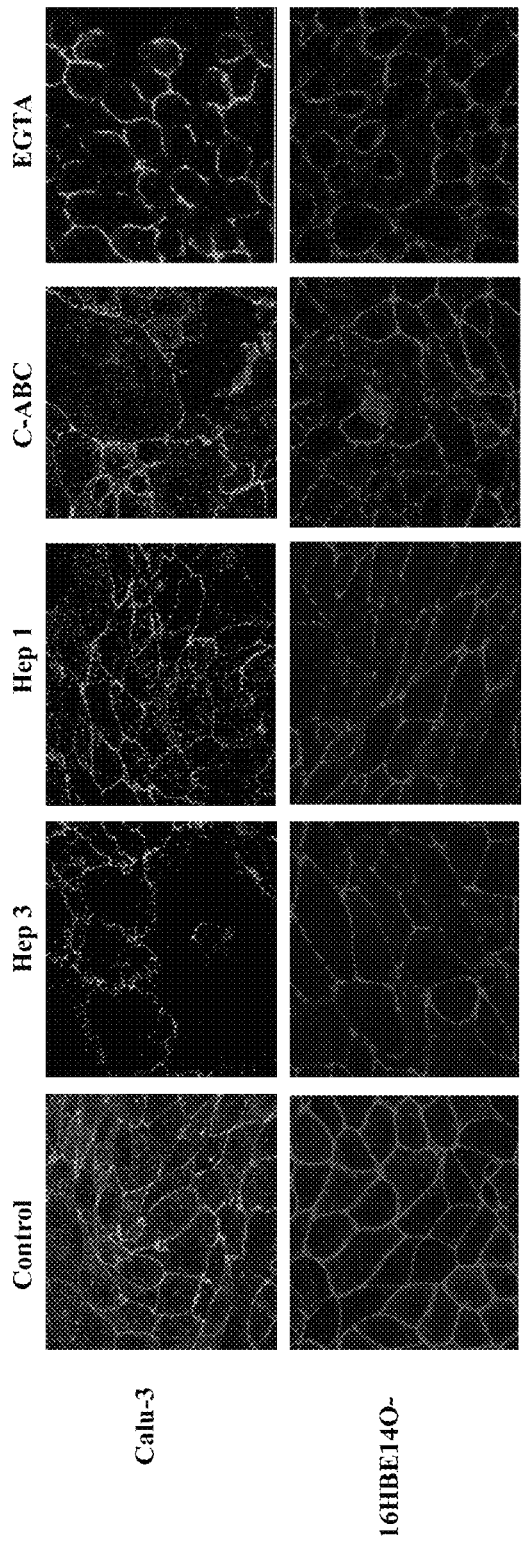
Fig 5: Immunofluorescence detection of ZO-1 in Calu-3 (human lung adenocarcinoma) and 16HBE14o- (virally transformed human bronchial epithelial cells) after treatment with glycosaminoglycan-degrading enzymes

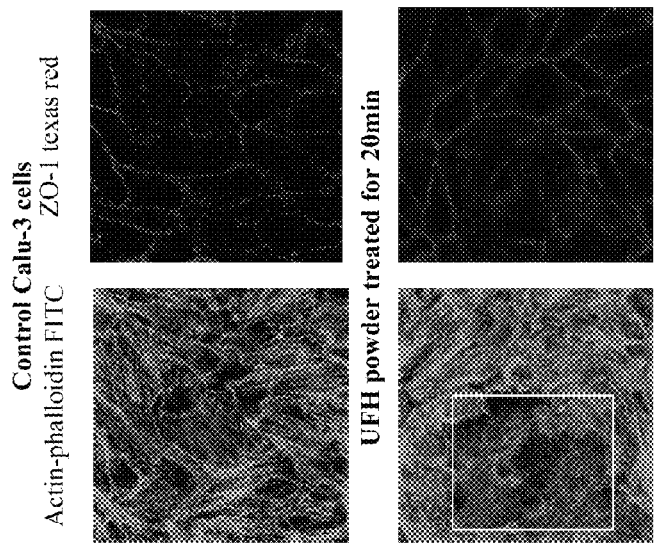
Figure 6: Effect of UFH on actin filaments and ZO-1 in calu3 epithelial cells
Figure 7: Effect of UFH on phosphorylation of ZO-1

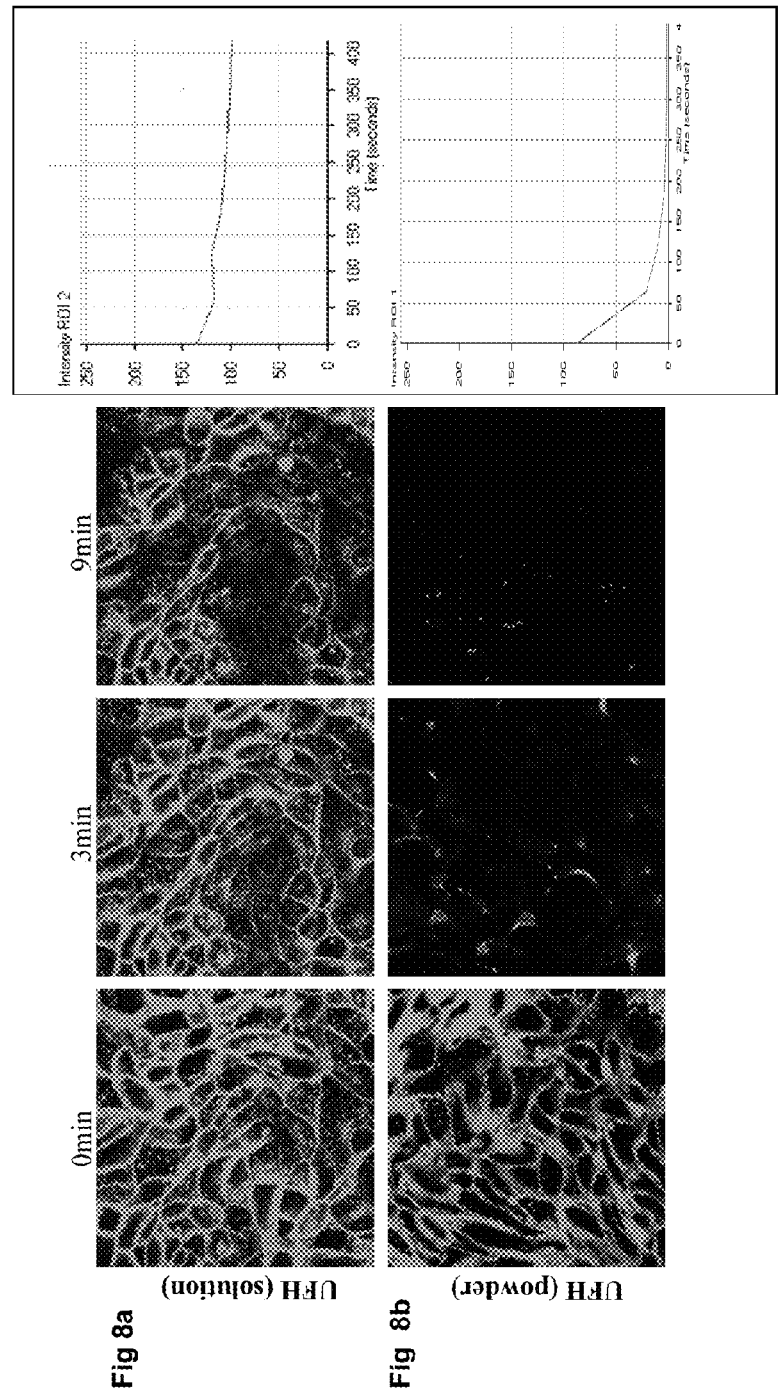
Figure 8: Influence of UFH on calcium level in Calu-3 epithelial cells

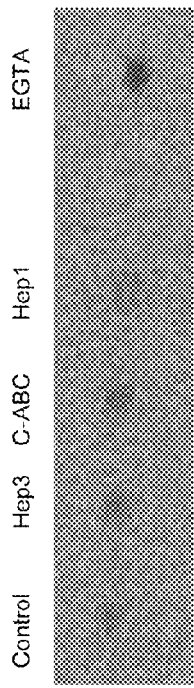
Fig 9b: Syndecan-4 ectodomain shedding in 16HBE14o-cells
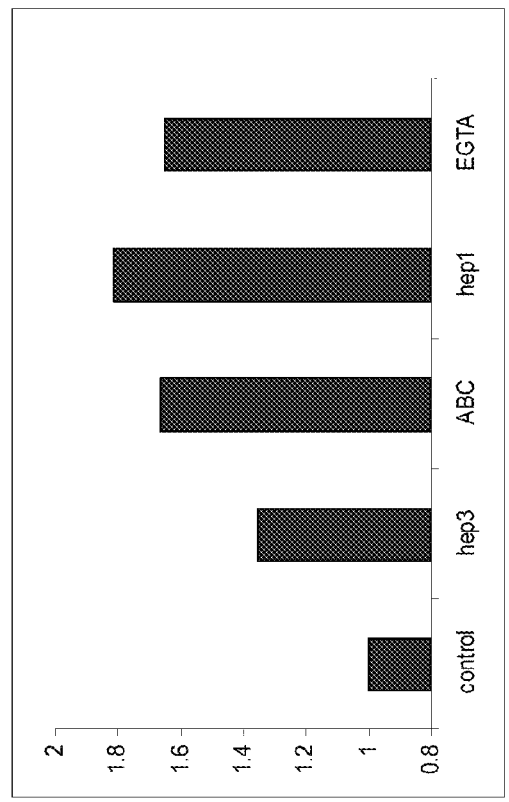
Figure 10: P-FAK levels in 16HBE14o-cells

METHODS AND COMPOSITIONS RELATED TO THE MODULATION OF INTERCELLULAR JUNCTIONS

RELATED APPLICATIONS

This application claims priority under 35 U.S.C. §119 from U.S. provisional application Ser. No. 60/584,438, filed Jun. 29, 2004, the entire contents of which is herein incorporated by reference.

GOVERNMENT SUPPORT

Aspects of the invention may have been made using funding from National Institutes of Health Grant number GM57073. Accordingly, the Government may have rights in the invention.

FIELD OF THE INVENTION

The invention relates to compositions and methods for the modulation of the permeability of the epithelial cell barrier complex. In particular, the invention provides compositions and methods of using polysaccharides, preferably glycosaminoglycans, and/or agents that modify cell surface glycosaminoglycans to modulate intercellular junctions. The compositions and methods provided can be used to facilitate the delivery of biologically active molecules.

BACKGROUND OF THE INVENTION

Epithelial tissues cover or line all body parts both externally and internally. With cells tightly packed together and with little intercellular space, the epithelial tissues form effective barriers between underlying tissues and external environment. Thus, the epithelial tissues are extremely important in regulating the exchange of materials between different body parts. Intercellular junctions are important for the development and functioning of epithelial tissues. In epithelia, tight junctions (or zonula occludens) are the most apical component of the intercellular junction complex (M. G. Farquhar et al., 1963), which also includes adherens junctions, desmosomes and gap junctions (Haraj N. S. et al., 2004).

The classical functions of the tight junctions (TJs) are the regulation of paracellular permeability and the restriction of apical-basolateral intramembrane diffusion of lipids (Matter K et al., 2003). Composed of occludin and various members of the claudin family of proteins (L. Gonzalez-Mariscal et al., 2003), the TJ strands can reject or retard certain solutes on the basis of their size and others on the basis of charge (G. T. Knipp et al., 1997). Thus, the formation of these intercellular junctional complexes between the epithelial cells provides protective barriers to the body against potentially harmful environmental conditions. These barriers, however, also obstruct the delivery of drugs to target tissues.

SUMMARY OF THE INVENTION

The invention relates, in part, to the discovery that polysaccharides, such as heparin, transiently disrupt intercellular junctions. This can result in the increased permeability of a cell barrier and, therefore, provides ways to enhance the delivery of biologically active molecules/agents. The invention further relates, in part, to the discovery that sodium heparin, ardeparin sodium, unfractionated heparin and polysaccharide-degrading enzymes, such as glycosaminoglycan-degrading enzymes like heparinase I (hep I), heparinase III (Hep III), chondroitinase ABC (cABC), etc., can also disrupt intercellular junctions.

In one aspect of the invention, therefore, methods and compositions for transiently disrupting intercellular junctions are provided. The methods include the step of contacting cells with a polysaccharide, a polysaccharide-degrading enzyme or both (also referred to herein as "intercellular junction disruption agents") in an amount effective to transiently disrupt one or more intercellular junctions. The methods can be in vitro methods or they can be in vivo methods. In in vivo methods the intercellular junction disruption agent is administered to a subject. In one embodiment the intercellular junction disruption agent results in the disruption of intercellular junctions and/or cell barrier permeability for more than 1 minute but less than 10 hours.

In some embodiments the subject is not ordinarily in need of the administration of the intercellular junction disruption agent. Therefore, in these embodiments, the subject does not suffer from a condition for which the use of the intercellular junction disruption agent is a recognized treatment. In other embodiments, however, the use of the intercellular junction disruption agent is a recognized treatment.

The intercellular junction disruption agents, biologically active agents and compositions provided herein can be administered by any means known in the art. In some embodiments the intercellular junction disruption agents and/or biologically active agents provided are administered via an ocular, nasal, topical, transdermal, or rectal route. In one embodiment the agent is administered via a nasal route in order to facilitate the delivery of the agent to the central nervous system (e.g., brain). Nasal administration can be accomplished, in some embodiments, with the use of nasal sprays, nasal drops or nasal gels containing the agent. In another embodiment delivery of the agent to the central nervous system (e.g., brain) is accomplished by the administration of the agent via an ocular route. Therefore the agent, in some embodiments, is in a form suitable for the administration to the eye. Such forms include an eye dropper, contact lens solution, ophthalmic ointment, eye pack or contact lens. Alternatively, the agent, in one embodiment, is administered in a composition that also contains a pharmaceutically acceptable carrier and an ophthalmic preservative. It follows that the agent in any of these forms suitable for administration to the eye is, in some embodiments, applied directly to the ocular surface (e.g., to the surface of the eye). In some embodiments the agent is administered to the mucous membranes. For such administration the agent is, in some embodiments, in an ointment, spray, a gel or mucoadhesive. In other embodiments the agent is administered via a pulmonary, sublingual, gastrointestinal, vaginal, rectal or oral route. For pulmonary delivery the agent, in some embodiments, is in an inhaler. For sublingual delivery, the agent, in some embodiments, is in a sublingual tablet or oral gel. For vaginal or rectal delivery the agent, in some embodiments, is in an ointment, tampon, suppository, enema or a mucoadhesive. For gastrointestinal delivery the agent, in some embodiments, is in an enteric-coated tablet or capsule. In one embodiment the agent is administered via the skin in order to facilitate its delivery to systemic circulation. Therefore, in some embodiments, the agent is administered topically. For topical administration, in some embodiments, the agent is in an ointment, lotion, spray, gel, cream, swab, wipe, bandage or patch. In another embodiment the agent is administered via a sublingual or gastrointestinal route to deliver it to systemic circulation. In still other embodiments the agent is administered intravenously, intraarterially or subcutaneously. In still other embodiments, for example, to enhance delivery across the blood-brain barrier, the agent is administered via the internal carotid artery. In another embodiment, for example, to facilitate delivery across the blood-brain barrier, an infusion pump is used to deliver the agent. The agent can be the intercellular junction disruption agent, the biologically active molecule or both.

In some embodiments the intercellular junction disruption agent is administered in a way not normally associated with its use as a therapeutic agent. In some embodiments the intercellular junction disruption agent is administered via a non-pulmonary route. In other embodiments the intercellular junction disruption agent is administered nonintravenously and/or nonsubcutaneously. In still other embodiments the intercellular junction disruption agent is administered via a route that is not oral and/or not gastrointestinal. In another embodiment the administration is not transdermal administration.

The intercellular junction disruption agent, in some embodiments, can be administered in a way that is different from the administration route of the biologically active agent. In other embodiments the agents can be administered in the same way.

In some embodiments the intercellular junction disruption agent is administered in an amount sufficient to disrupt intercellular junctions but not in an amount effective to treat a subject with a condition. In other embodiments the intercellular junction disruption agent is administered in an amount that is sufficient to disrupt intercellular junctions and is therapeutically effective. However, in some embodiments the therapeutically effective amount of the intercellular junction disruption agent is such that it is less effective for treating a condition than a biologically active agent that is administered to the subject prior to, after or concurrently with the intercellular junction disruption agent.

In some embodiments the biologically active agent is different from the intercellular junction disruption agent. The intercellular junction disruption agent and/or biologically active agent can be administered in any form suitable for the desired purpose. In some embodiments the agent is administered in particulate or powder form. In one embodiment the intercellular junction disruption agent is heparin or ardeparin which is in powder or particulate form. In another embodiment the intercellular junction disruption agent is sodium heparin or sodium ardeparin which is in powder or particulate form. In yet another embodiment the intercellular junction disruption agent is sodium heparin which is in powder or particulate form. In other embodiments the agent is administered in a solution. In one embodiment the solution is a solution suitable for administration to the ocular surface. In one embodiment the solution is an isotonic solution. In still other embodiments the agent is administered in an aerosol form. In an additional embodiment, the agent is administered in a suspension or a super-concentrated or supersaturated solution (a mix of a suspension or powder in a solution). In one embodiment the superconcentrated or supersaturated solution contains a concentration of an agent of greater than 20 mg/ml. In one embodiment the intercellular junction disruption agent is at a concentration of greater than 20 mg/ml. In another embodiment the solution contains greater than 20 mg/ml heparin. In yet other embodiments the biologically active agent is administered in a form different from the form of the intercellular junction disruption agent.

The intercellular junction disruption agent can be any polysaccharide that when contacted with cells, disrupts intercellular junctions. In one embodiment the polysaccharide is a digestible polysaccharide. In another embodiment the polysaccharide is a linear polysaccharide. In yet another embodiment the polysaccharide does not possess anticoagulant properties. The polysaccharide in another embodiment is a glycosaminoglycan. In some embodiments the glycosaminoglycan does not possess anticoagulant activity. In one embodiment the glycosaminoglycan (e.g., heparin) is missing the anticoagulant portions or parts thereof normally found in the glycosaminoglycan. In one embodiments the glycosaminoglycan does not have a complete and/or active antithrombin (AT) III binding domain. In one embodiment the glycosaminoglycan lacks an AT III binding domain.

In some embodiments the glycosaminoglycan is not associated with a proteoglycan. In other embodiments the glycosaminoglycan is a heparin-like glycosaminoglycan (HL-GAG) or heparan sulfate-like glycosaminoglycan (HSGAG). In still other embodiments the glycosaminoglycan is a chondroitin sulfate glycosaminoglycan (CSGAG). In yet other embodiments the glycosaminoglycan is not one generated by the activity of chondroitinase ABC I (cABC I). In other embodiments the glycosaminoglycan is a low molecular weight heparin. In some embodiments the glycosaminoglycan is heparin, such as sodium salt of heparin. In other embodiments the glycosaminoglycan is unfractionated heparin. In still other embodiments the glycosaminoglycan is ardeparin, such as ardeparin sodium.

The intercellular junction disruption agent can also be a polysaccharide-degrading enzyme. In some embodiments the polysaccharide-degrading enzyme is a glycosaminoglycan-degrading enzyme. In some embodiments the glycosaminoglycan-degrading enzyme is a heparinase, such as heparinase I (Hep I), heparinase II (Hep II) or heparinase III (Hep III). In other embodiments the glycosaminoglycan-degrading enzyme is a chondroitinase, such as chondroitinase AC (cAC), chondroitinase B (cB), chondroitinase C (cC), or chondroitinase ABC (cABC). In some embodiments the chondroitinase ABC is chondroitinase ABC I (cABC I) or chondroitinase ABC II (cABC II). In still other embodiments the glycosaminoglycan-degrading enzyme is a sulfatase or sulfotransferase. In still further embodiments the intercellular junction disruption agent can be a combination of one or more different polysaccharides and one or more different polysaccharide-degrading enzymes. In some embodiments it is the combination that is effective in disrupting intercellular junctions and/or is therapeutically effective.

The compositions and methods provided can be used to disrupt one or more intercellular junctions between cells of any type and result in the increased absorption of the intercellular junction disruption agent. The cells can be epithelial or endothelial cells. In some embodiments the methods provided further include contacting the cells with one or more different kinds of biologically active molecules. The methods provided, therefore, can result in the increased absorption of biologically active molecules. When performed in vivo the methods further include, in some embodiments, administering to a subject one or more biologically active molecules. In some embodiments the biologically active molecule is administered in an amount effective to treat the subject.

The agents provided herein can be administered in any amount effective for the desired purpose. In one embodiment the intercellular junction disruption agent is administered at a level from 3 micrograms to 14 micrograms per 4 square centimeters area of cells. In one embodiment the intercellular junction disruption agent administered at such a level is sodium heparin.

The biologically active molecules can be any molecule that has some desired biological effect. Biologically active molecules, which are also referred to herein as "biologically active agents", therefore, include therapeutic agents, such as a drug. The biologically active molecule, in some embodiments, is a polar or charged molecule. The biologically active molecule in some embodiments is a protein, chemical compound, nucleic acid, polysaccharide, small molecule or peptide therapeutic. When the biologically active molecule is a nucleic acid, in some of these embodiments, the nucleic acid is DNA, RNA or siRNA. In other embodiments the biologically active molecule is one that without the administration of the intercellular junction disruption agent would not permeate one or more cell barriers in a subject. In still other embodiments the biologically active molecule is one that has an enhanced permeation of one or more cell barriers because of the administration of the intercellular junction disruption agent. In some of these embodiments the permeation of the cell barrier of the biologically active agent is 5%, 10%, 15%, 20%, 25%, 30%, 40%, 50%, 60%, 70%, 80%, 90%, 100%, 200%, 300%, 400%, 500%, 1000%, 2000%, 5000%, or more more than the permeation of the biologically active agent without the administration of the intercellular junction disruption agent.

The intercellular junction disruption agent can be administered prior to, concurrently with or after the administration of a biologically active agent. In one aspect of the invention the intercellular junction disruption agent is administered concurrently with or prior to the administration of the biologically active agent. In another aspect of the invention the intercellular junction disruption agent is administered prior to the administration of the biologically active agent. In some embodiments the intercellular junction disruption agent is administered 1, 2, 3, 4, 5, 10, 15, 20, 25, 30, 60 or more minutes prior to the administration of the biologically active agent. In other embodiments the intercellular junction disruption agent is administered 1, 2, 3, 4, 5, 6, 7, 8, 9, 10, 15, 20 or more hours prior to the administration of the biologically active agent. In still other embodiments the intercellular junction disruption agent is administered at least 10 minutes prior to the administration of the biologically active agent. In still other embodiments the intercellular junction disruption agent is administered no more than 1, 2, 3, 4, 5, 6, 7, 8, 9, or 10 hours before the administration of the biologically active agent. In still other embodiments the intercellular junction disruption agent is administered anywhere from 1 minute to 10 hours prior to the administration of the biologically active agent.

In another embodiment the biologically active agent is administered prior to the administration of the intercellular junction disruption agent. In some embodiments the biologically active agent is administered 1, 2, 3, 4, 5, 10, 15, 20, 25, 30, 60 or more minutes prior to the administration of the intercellular junction disruption agent. In other embodiments the biologically active agent is administered 1, 2, 3, 4, 5, 6, 7, 8, 9, 10, 15, 20, 30, 40, 50, 60, 75, 100 or more hours prior to the administration of the intercellular junction disruption agent. In still other embodiments the biologically active agent is administered at least 10 minutes prior to the administration of the intercellular junction disruption agent. In yet other embodiments the biologically active agent is administered 1, 2, 3, 4, 5, 10, 20, 30 or more days prior to the administration of the intercellular junction disruption agent. In further embodiments the biologically active agent is administered 1, 2, 3, 4, 5, 10, 20, 30 or more months prior to the administration of the intercellular junction disruption agent. In yet other embodiments the biologically active agent is administered 1, 2, 3, 4, 5 or more years prior to the administration of the intercellular junction disruption agent. In some embodiments, therefore, administration can be accomplished with the use of slow (also referred to herein as "controlled") release materials, such as polyanhydride wafers or block copolymers, such as poly(ethylene glycol) (PEG)/poly(lactic-co-glycolic acid) (PLGA) block copolymers as an example. In still other embodiments the biologically active agent is administered no more than 1, 2, 3, 4, 5, 6, 7, 8, 9, 10, 15, 24, 36 or 72 hours before the administration of the intercellular junction disruption agent.

In other aspects of the invention, therefore, compositions and methods for increasing the permeability of a cell barrier by contacting the cell barrier with an intercellular junction disruption agent in an amount effective to increase the permeability of the cell barrier are provided.

In one embodiment the method is performed in a subject not ordinarily in need of the administration of the intercellular junction disruption agent.

In another embodiment the biologically active molecule is an agent for treating a central nervous system disorder, for treating a coagulation disorder, for treating a cardiovascular disorder, for treating arteriosclerosis, for treating atherosclerosis, for treating a respiratory disorder, for treating an infection or infection related disorder, for treating cancer, for treating an inflammatory disorder, for treating an immunologic disorder, for treating an allergic disorder, for treating an angiogenic disorder, for treating a dermatologic disorder, for treating a renal disorder, for treating a gastrointestinal disorder, for treating an endocrinal disorder, for treating diabetes or for treating an ocular disorder. In another embodiment the agent is an anticancer agent, an antiangiogenic agent, an anticoagulant, an antithrombotic agent, an antimicrobial agent, an antiprotozoal agent, an antibacterial agent, an antiviral agent, an antifungal agent, an antidepressant, an antiasthmatic agent, an antiinflammatory agent, an antihypertension agent, a diuretic, an anti-ulcer agent, an agent for hormonal therapy, insulin, a bronchodilator or an antiallergic agent.

From the above it follows that the cell barrier can be an epithelial cell barrier or an endothelial cell barrier. The methods, in some embodiments, can also further comprise the step of contacting the cell barrier with a biologically active molecule. The cell barriers in some embodiments can be the blood-brain barrier, nasal membrane, skin, or sublingual membrane. In other embodiments the cell barrier is in the gastrointestinal tract or upper or lower respiratory tracts. In still other embodiments the cell barrier includes those formed by pericytes, pneumocytes, and glial cells (e.g., astrocytes). In another embodiment the cell barrier is in muscle (e.g., smooth muscle).

In other aspects of the invention, methods and compositions for enhancing the delivery of one or more biologically active molecules by administering to a subject one or more intercellular junction disruption agents and one or more biologically active molecules are provided. In some embodiments the intercellular junction disruption agent is a polysaccharide-degrading enzyme. In one embodiment the intercellular junction disruption agent is a glycosaminoglycan-degrading enzyme. In some embodiments the intercellular junction disruption agent is administered prior to or after the biologically active agent is administered. In such embodiments the biologically active agent is administered at a time whereby the intercellular disrupting effects of the intercellular junction disruption agent allows for the enhanced delivery of the biologically active agent. In one embodiment the intercellular junction disruption agent is administered to a subject not ordinarily in need of the intercellular junction disruption agent. In still other embodiments the intercellular junction disruption agent is a polysaccharide-degrading enzyme or both a polysaccharide-degrading enzyme and a polysaccharide.

In some aspects of the invention methods and compositions for enhancing the delivery of one or more biologically active molecules through the upper or lower respiratory tract in a subject by administering to the subject one or more intercellular junction disruption agents and one or more biologically active molecules are provided. In one aspect the intercellular junction disruption agent and/or the biologically active agent is administered to the upper or lower respiratory tract of a subject. In one embodiment this is accomplished by inhalation using a medical device. In another embodiment the medical device is an inhaler. In still another embodiment the administration of the intercellular junction disruption agent and/or the biologically active agent is accomplished by nasal administration. In one aspect, therefore, compositions and methods for enhancing the delivery of a biologically active molecule through nasal administration in a subject by administering via the nasal membrane of the subject an intercellular junction disruption agent and a biologically active molecule are provided.

The administration of the intercellular junction disruption agent and/or the biologically active agent can also be accomplished by ocular administration. In another aspect of the invention compositions and methods for enhancing the delivery of a biologically active molecule through ocular administration in a subject by administering ocularly to the subject an intercellular junction disruption agent and a biologically active molecule are provided.

The administration of the intercellular junction disruption agent and/or the biologically active agent can also be accomplished by administration through the skin, sublingual or gastrointestinal route. Therefore, in still other aspects of the invention compositions and methods for enhancing the delivery of a biologically active molecule through the skin, sublingual or gastrointestinal route in a subject by administering via the skin, sublingual tissue or gastrointestinal tissue of the subject an intercellular junction disruption agent and a biologically active agent are provided. In some embodiments the administration is carried out with a bandage, slow or controlled release patch, engineered or biodegradable scaffold, slow or controlled release polymer, tablet or capsule. In some embodiments the intercellular junction disruption agent and/or biologically active agent are topically applied.

In other aspects of the invention a method for enhancing the delivery of a biologically active molecule through the blood-brain barrier by administering to a subject an intercellular junction disruption agent and a biologically active molecule is provided. In one embodiment the intercellular junction disruption agent and/or biologically active molecule is administered via a nonpulmonary, nonintravenous, nonsubcutaneous, nonoral, nongastrointestinal and nontransdermal route. In still another embodiment the intercellular junction disruption agent and/or biologically active molecule is administered via the internal carotid artery. In yet another embodiment the intercellular junction disruption agent and/or biologically active molecule is linked to a molecule that targets the blood-brain barrier. In another embodiment the molecule that targets the blood-brain barriers is an antibody to a receptor on the blood-brain barrier. In another embodiment the antibody is an antibody to transferrin receptor. In still another embodiment the antibody is OX 26. In yet another embodiment the antibody is an antibody to PGP1. In still another embodiment the intercellular junction disruption agent is administered prior to, concurrently with or after the biologically active molecule.

In some embodiments the methods provided herein enhance the delivery of the biologically active molecule to systemic circulation and/or the central nervous system (e.g., brain).

The methods and compositions provided herein can be used to treat a subject with a disease or disorder. In some embodiments the subject has a systemic disease. In some embodiments the subject has a coagulation disorder. In some embodiments the coagulation disorder is thrombosis associated with cardiovascular disease or a vascular condition. In some embodiments the subject has a cardiovascular disorder. In one embodiment the cardiovascular disorder is acute myocardial infarction, unstable angina or atrial fibrillation. In other embodiments the subject has a vascular condition. In another embodiment the vascular condition is deep venous thrombosis, stroke or pulmonary embolism. In some embodiments the subject has atherosclerosis. In still further embodiments the subject has an angiogenic disorder. In some embodiments the angiogenic disorder is a neovascular disorder of the eye, osteoporosis, psoriasis, arthritis, an angioma, a port wine stain or a vascular cyst. In still other embodiments the angiogenic disorder is cancer. In other embodiments the subject has a cerebrovascular condition. In some embodiments the cerebrovascular condition is stroke, carotid artery stenosis, carotid artery atherosclerosis, cerebral arteriosclerosis, cerebral aneurysm, intracranial hemorrhage (subarachnoid hemorrhage, berry aneurysms, etc.), lacunar infarcts, slit hemorrhages (hypertension related), hypertensive encephalopathy, cerebral autosomal dominant arteriopathy with subcortical infarcts and leukoencephalopathy (CADASIL) or cerebral artery disease.

In other embodiments the subject has a respiratory disorder. In some of these embodiments the subject has asthma, emphysema/chronic obstructive pulmonary disease, adult respiratory distress syndrome (ARDS), neonatal respiratory distress syndrome or lung reperfusion injury. In another embodiment the subject has a lung disease. In some embodiments the lung disease is fibrosis, restrictive lung disease, obstructed lung disease, mesothelioma, pneumonia, tuberculosis, sarcoidosis, Wegener's disease or cystic fibrosis. In one embodiment the subject has fibrotic lungs.

In some embodiments the subject has cancer. In one embodiment the cancer is a carcinoma. In another embodiment the cancer is a sarcoma. In other embodiments the subject has biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreatic cancer; prostate cancer; rectal cancer; sarcomas; skin cancer; testicular cancer; thyroid cancer; or renal cancer.

In other embodiments the subject has an inflammatory disorder. In some embodiments the inflammatory disorder is non-autoimmune inflammatory bowel disease, post-surgical adhesions, coronary artery disease, hepatic fibrosis, acute respiratory distress syndrome, acute inflammatory pancreatitis, endoscopic retrograde cholangiopancreatography-induced pancreatitis, burns, atherogenesis of coronary, cerebral and peripheral arteries, appendicitis, cholecystitis, diverticulitis, visceral fibrotic disorders, wound healing, skin scarring disorders (keloids, hidradenitis suppurativa), granulomatous disorders (sarcoidosis, primary biliary cirrhosis), asthma, pyoderma gandrenosum, Sweet's syndrome, Behcet's disease, primary sclerosing cholangitis or an abscess. In still another embodiment the inflammatory condition is an autoimmune condition. The autoimmune condition in some embodiments is rheumatoid arthritis, rheumatic fever, ulcerative colitis, Crohn's disease, autoimmune inflammatory bowel disease, insulin-dependent diabetes mellitus, diabetes mellitus, juvenile diabetes, spontaneous autoimmune diabetes, gastritis, autoimmune atrophic gastritis, autoimmune hepatitis, thyroiditis, Hashimoto's thyroiditis, insulitis, oophoritis, orchitis, uveitis, phacogenic uveitis, multiple sclerosis, myasthenia gravis, primary myxoedema, thyrotoxicosis, pernicious anemia, autoimmune haemolytic anemia, Addison's disease, scleroderma, Goodpasture's syndrome, Guillain-Barre syndrome, Graves' disease, glomerulonephritis, psoriasis, pemphigus vulgaris, pemphigoid, sympathetic opthalmia, idiopathic thrombocylopenic purpura, idiopathic feucopenia, Siogren's syndrome, Wegener's granulomatosis, poly/dermatomyositis or systemic lupus erythematosus.

In another embodiment the subject has an immunologic disorder. In one embodiment the immunologic disorder is lupus. In one embodiment the immunologic disorder is primary immune deficiency disease or an autoimmune disease or disorder. In another embodiment the autoimmune disease or disorder is autoimmune deficiency syndrome (AIDS), systemic lupus erythematosus (SLE), rheumatic fever, rheumatoid arthritis, systemic sclerosis, autoimmune Addison's disease, Anklosing spondylitis or sarcoidosis.

In still another embodiment the subject has an infection (e.g., *pseudomonas* infection or *S. aureus* infection) or an infection related disorder. In some embodiments the infection is a viral infection, a bacterial infection or a fungal infection.

In still other embodiments the subject has an allergic disorder. In some embodiments the allergic disorder is eczema, allergic rhinitis or coryza, hay fever, conjunctivitis, bronchial asthma, urticaria (hives) and food allergies or other atopic conditions.

In still another embodiment the subject has inflammatory bowel disease (IBD). In one embodiment the IBD is Crohn's disease. In another embodiment the IBD is ulcerative colitis.

In another embodiment the subject has a renal disorder. In some embodiments the subject has kidney stones or a renal infection. In another embodiment the subject has a urinary tract infection. In still another embodiment the renal disorder is human glomerulonephritis (GN), end-stage renal disease, chronic diabetic nephropathy, diabetic glomerulopathy, diabetic renal hypertrophy, hypertensive nephrosclerosis, hypertensive glomerulosclerosis, chronic glomerulonephritis, hereditary nephritis, renal dysplasia or chronic rejection following renal allograft transplantation.

In yet another embodiment the subject has a gastrointestinal disorder. In one embodiment the gastrointestinal disorder is gastrointestinal ulceration.

In still a further embodiment the subject has an endocrinal disorder. In one embodiment the endocrinal disorder is Addison disease, Acromegaly, adrenal gland disease, congenital adrenal hyperplasia, androgen-insensitivity syndrome, cretinism, cushing syndrome, diabetes insipidus, diabetes mellitis, grave's disease, Kallman syndrome, pituitary diseases, parathyroid diseases, precocious puberty, renal osteodystrophy, autoimmune polyendocrinopathies, Nelson syndrome, hyperglycemic hyperosmolar nonketotic coma, hyperpituitarism, hyperprolactinemia, hyperthyroidism, hyperaldosteronism, gigantism, gonadal disorders, Empty Sella syndrome thyroid nodule, thyroiditis, autoimmune thyroiditis, subacute thyroiditis or wolfram syndrome.

In some embodiments the subject has a central nervous system disorder. In some embodiments the central nervous system disorder is Alzheimers, Parkinson's disease, Hunting-ton's disease, cerebrovascular disease, epilepsy, depression, mania, bipolar disorder, schizophrenia or a psychotic disorder. In another embodiment the subject has suffered a brain and/or spinal cord injury. In some embodiments the subject is in need of improved cerebral/behavioral function (i.e., the subject suffers from cerebral injury and/or loss of cerebral/behavioral function). In other embodiments the subject is in need of neural regeneration and/or spinal cord repair.

In other embodiments the subject has a dermatological disorder. In some embodiments the dermatological disorder is vitiligo, melanoma, dysplasic nevi, seborrheic keratoses, acanthosis nigricans, adnexal tumors, other epidermal tumors (actinic keratosis, squamous cell carcinoma, basal cell carcinoma, merkel cell carcinoma, histiocytosis X, mycosis fungoides/cutaneous T-cell lymphoma), mastocytosis, eczema/acute eczematous dermatitis, urticaria, erythema multiforme, psoriasis, lichen planus, lupus/systemic lupus erythematosus, bullous diseases, acne vulgaris, cellulitis, folliculitis, fascitis, keloids, exuberant granulation or panniculitis. In one embodiment the dermatological disorder is not psoriasis.

In yet another embodiment the subject has an ocular disorder. In some embodiments the ocular disorder is glaucoma, ocular degeneration, central retinary artery occlusion, central retinal vein occlusion, retinal detachment, macular degeneration, a retinopathy, cataract or an ocular infection.

In still other embodiments the subject has diabetes, encephalitis, hydrocephalus, obesity, varicose veins, vasculititides, lymphangitis, lymphedema, hypertension, superior vena caval syndrome, myocarditis, restrictive cardiomyopathy, pericarditis, a hereditary hemopoetic disorder, disseminated intravascular coagulation, Wilson's disease, alpha1-antitrypsin disease, cholecystitis, cholangitis, gall stones, a bladder infection or a protein deficiency (e.g. Tay Sachs).

In yet another embodiment the subject has a chronic wound. In one embodiment the compositions provided are administered to a wound bed.

In another aspect of the invention methods for treating a subject by administering to the subject one or more intercellular junction disruption agent and one or more biologically active molecules are provided. In one aspect a method for treating a subject by administering to the subject an intercellular junction disruption agent and a biologically active molecule, wherein the subject has a central nervous system disorder is provided. In one embodiment the subject is not administered a chondroitinase ABC I-generated chondroitin sulfate fragment or chondroitinase ABC I. In another embodiment the biologically active molecule is an agent for treating a central nervous system disorder.

In another aspect of the invention a method for treating a subject by administering to the subject an intercellular junction disruption agent and a biologically active molecule, wherein the subject has an infection or an infection related disorder is provided. In one embodiment the intercellular junction disruption agent is a heparan sulfate-like glycosaminoglycan, a heparin-like glycosaminoglycan or an enzyme that degrades heparan sulfate-like glycosaminoglycans or heparin-like glycosaminoglycans or some combination thereof. In another embodiment the biologically active molecule is an agent for treating the infection or infection related disorder. In one embodiment the agent for treating the infection or infection related disorder is an antimicrobial agent.

In another aspect of the invention a method for treating a subject by administering to the subject an intercellular junction disruption agent and a biologically active molecule, wherein the subject has an infection or infection related disorder is provided. In one embodiment the infection is not maternal malarial infection. In another embodiment the subject is not administered a chondroitinase ABC I-generated chondroitin sulfate fragment or chondroitinase ABC I. In yet another embodiment the biologically active molecule is an agent for treating the infection or infection related disorder. In one embodiment the agent for treating the infection or infection related disorder is an antimicrobial agent.

In yet another aspect of the invention a method for treating a subject by administering to the subject a intercellular junction disruption agent and a biologically active molecule, wherein the subject has a respiratory disorder is provided. In one embodiment the intercellular junction disruption agent is a glycosaminoglycan-degrading enzyme. In another embodiment the biologically active molecule is an agent for treating the respiratory disorder. In yet another embodiment the agent is an antiasthmatic agent. In still a further embodiment the intercellular junction disruption agent is administered via a nonpulmonary route. In yet another embodiment the respiratory disorder is lung infection. In another embodiment the respiratory disorder is tuberculosis or pneumonia. In one embodiment where the respiratory disorder is tuberculosis the intercellular junction disruption agent and/or the biologically active agent is administered orally or intramuscularly. In another embodiment where the respiratory disorder is pneumonia the intercellular junction disruption agent and/or the biologically active agent is administered orally or intravenously. In other embodiments the administration of the intercellular junction disruption agent and/or the biologically active molecule is by oral, intramuscular or intravenous administration. In another embodiment the biologically active molecule is an agent for treating the respiratory disorder. In still a further embodiment the biologically active agent is an antiasthmatic agent.

In still a further aspect of the invention a method for treating a subject by administering to the subject an intercellular junction disruption agent and a biologically active molecule, wherein the subject has an ocular disorder is provided. In one embodiment the intercellular junction disruption agent is a chondroitin sulfate glycosaminoglycan or a chondroitinase. In another embodiment the biologically active molecule is an agent for treating the ocular disorder. In still another embodiment the ocular disorder is central retinary artery occlusion, central retinal vein occlusion, retinal detachment, glaucoma, macular degeneration, ocular degeneration, a retinopathy, cataract or an ocular infection. In another embodiment the biologically active molecule is an agent for treating the ocular disorder. In still a further embodiment the agent for treating the ocular disorder is an antimicrobial agent, an antithrombotic agent, an antiangiogenic agent, an antiproliferative agent, a vasodilatory agent, an antiglaucoma agent, an agent for treating diabetes or an agent for promoting neuronal regeneration.

In yet another aspect of the invention a method for treating a subject by administering to the subject an intercellular junction disruption agent and a biologically active molecule, wherein the subject has an immunologic disorder is provided. In still another embodiment the immunologic disorder is not rheumatoid arthritis or psoriasis. In yet another embodiment the biologically active molecule is an agent for treating the immunologic disorder. In yet another embodiment the immunologic disorder is not psoriasis. In a further embodiment the intercellular junction disruption agent is a chondroitin sulfate glycosaminoglycan or a chondroitinase. In yet a further embodiment the immunologic disorder is not psoriasis, and the intercellular junction disruption agent is a chondroitin sulfate glycosaminoglycan or a chondroitinase.

In still a further aspect of the invention a method for treating a subject by administering to the subject an intercellular junction disruption agent and a biologically active molecule, wherein the subject has a dermatologic disorder is provided.

In one embodiment the dermatologic disorder is not psoriasis. In yet another embodiment the biologically active molecule is an agent for treating the dermatologic disorder.

Compositions of intercellular junction disruption agents and/or biologically active agents are also provided herein in some aspects of the invention. In one aspect of the invention a composition is provided that contains an intercellular junction disruption agent and a biologically active molecule, wherein the biologically active molecule is an agent for treating central nervous system disorders. In one embodiment the intercellular junction disruption agent is not a chondroitinase ABC I-generated chondroitin sulfate fragment or chondroitinase ABC I.

In another aspect of the invention a composition is provided that contains an intercellular junction disruption agent and a biologically active molecule, wherein the biologically active agent is an agent for treating an infection or an infection related disorder. In one embodiment the intercellular junction disruption agent is a heparan sulfate-like glycosaminoglycan, a heparin-like glycosaminoglycan, or an enzyme that degrades heparan sulfate-like glycosaminoglycans or heparin-like glycosaminoglycans or some combination thereof. In another embodiment the agent for treating the infection or infection related disorder is an antimicrobial agent. In another embodiment the biologically active agent is not an agent for treating maternal malarial infection. In another embodiment the intercellular junction disruption agent is not a chondroitinase ABC I-generated chondroitin sulfate fragment or chondroitinase ABC I. In still a further embodiment the biologically active agent is not an agent for treating maternal malarial infection, and the intercellular junction disruption agent is not a chondroitinase ABC I-generated chondroitin sulfate fragment or chondroitinase ABC I.

In another aspect of the invention a composition is provided that contains an intercellular junction disruption agent and a biologically active molecule, wherein the biologically active agent is an agent for treating a respiratory disorder. In one embodiment the biologically active agent is an antiasthmatic agent.

In still a further aspect of the invention a compositions is provided that contains an intercellular junction disruption agent and a biologically active molecule, wherein the biologically active agent is an agent for treating an ocular disorder. In one embodiment the intercellular junction disruption agent is a chondroitin sulfate glycosaminoglycan or a chondroitinase. In another embodiment the ocular disorder is central retinary artery occlusion, central retinal vein occlusion, retinal detachment, glaucoma, macular degeneration, ocular degeneration, a retinopathy, cataract or an ocular infection.

In still a further aspect of the invention a composition is provided that contains an intercellular junction disruption agent and a biologically active molecule, wherein the biologically active agent is an agent for treating an immunologic disorder. In one embodiment the immunologic disorder is not rheumatoid arthritis or psoriasis.

In still a further aspect of the invention a composition is provided that contains an intercellular junction disruption agent and a biologically active molecule, wherein the biologically active agent is an agent for treating an immunologic disorder. In one embodiment the immunologic disorder not psoriasis. In another embodiment the intercellular junction disruption agent is a chondroitin sulfate glycosaminoglycan or a chondroitinase. In still a further embodiment the immunologic disorder not psoriasis, and the intercellular junction disruption agent is a chondroitin sulfate glycosaminoglycan or a chondroitinase.

In yet another aspect of the invention a composition is provided that contains an intercellular junction disruption agent and a biologically active molecule, wherein the biologically active agent is an agent for treating a dermatologic disorder. In one embodiment the dermatologic disorder is not psoriasis.

In yet another aspect of the invention a composition is provided that contains an intercellular junction disruption agent and a biologically active molecule, wherein the intercellular junction disruption agent and/or the biologically active molecule is linked to a molecule that targets the blood-brain barrier.

In yet another aspect of the invention a composition is provided that contains an intercellular junction disruption agent and a biologically active molecule, wherein the composition is in a form suitable for administration to the eye. In one embodiment the form suitable for administration to the eye is an eye dropper, a contact lens solution, an ophthalmic ointment, an eye pack, a contact lens or an isotonic solution.

In still another aspect of the invention a composition is provided that contains an intercellular junction disruption agent and a biologically active molecule, wherein the composition further contains a pharmaceutically acceptable carrier that comprises an ophthalmic preservative.

In one embodiment the biologically active molecule is an agent for treating an ocular disorder. In another embodiment the biologically active molecule is an agent for treating a central nervous system disorder. In still another embodiment the biologically active molecule is an agent for treating a cerebrovascular condition.

In another aspect of the invention a composition is provided that contains an intercellular junction disruption agent and a biologically active molecule, wherein the composition is in a form suitable for nasal administration. In one embodiment the form suitable for nasal administration is a nasal spray, nasal drop or nasal gel.

In still a further aspect of the invention a composition is provided that contains an intercellular junction disruption agent and a biologically active molecule, wherein the composition is in a form suitable for topical administration. In one embodiment the form suitable for topical administration is an ointment, lotion, spray, gel, cream, swab, wipe, bandage or patch.

In yet another aspect of the invention a composition is provided that contains an intercellular junction disruption agent and a biologically active molecule, wherein the composition is in a form suitable for pulmonary delivery. In one embodiment the form suitable for pulmonary delivery is an inhaler.

In still a further aspect of the invention a composition is provided that contains an intercellular junction disruption agent and a biologically active molecule, wherein the composition is in a form suitable for sublingual delivery. In one embodiment the form suitable for sublingual delivery is a sublingual tablet or oral gel.

In still another aspect of the invention a composition is provided that contains an intercellular junction disruption agent and a biologically active molecule, wherein the composition is in a form suitable for vaginal or rectal delivery. In one embodiment the form suitable for vaginal or rectal delivery is an ointment, tampon, suppository, enema or a mucoadhesive formulation.

In yet another aspect of the invention a composition is provided that contains an intercellular junction disruption agent and a biologically active molecule, wherein the compositions is in a form suitable for gastrointestinal delivery. In one embodiment the form suitable for gastrointestinal delivery is an enteric tablet or capsule.

The biologically active agent in the compositions provided and for use in the methods provided can be any agent for the treatment of any of the disorders as provided herein. In one embodiment the agent is an agent for treating a coagulation disorder. In one embodiment the biologically active agent is an anticoagulant. In another embodiment the biologically active agent is an antithrombotic agent. In still another embodiment the biologically active agent is a therapeutic agent for treating a cardiovascular disease/disorder, a vascular condition or a cerebrovascular condition. In another embodiment the biologically active agent is an antiangiogenic agent. In yet another embodiment the biologically active agent is a therapeutic agent for treating a respiratory disorder. In one embodiment the therapeutic agent for treating a respiratory disorder is an antiasthmatic agent. In still another embodiment the biologically active agent is a therapeutic agent for treating a lung disease. In still a further embodiment the biologically active agent is an anticancer agent. In one embodiment the anticancer agent is an antiangiogenic agent. In yet another embodiment the biologically active agent is an antiinflammatory agent. In still further embodiment the biologically active agent is an antiallergic agent. In still another embodiment the biologically active agent is a therapeutic agent used to treat an immunologic disorder. In yet another embodiment the biologically active agent is a therapeutic agent to treat an infection or infection related disorder. In one embodiment the therapeutic agent for treating an infection or infection related disorder is an antimicrobial agent. In another embodiment the antimicrobial agent is an antiprotozoal, antifungal, antibacterial or antiviral agent. In another embodiment the biologically active agent is a therapeutic agent for treating a dermatological disorder. In still another embodiment the biologically active agent is a therapeutic agent for treating an ocular disorder or ocular infection. In one embodiment the biologically active agent for treating an ocular disorder or ocular infection is an antimicrobial agent. In another embodiment the antimicrobial agent is an antiprotozoal, antifungal, antibacterial or antiviral agent. In yet another embodiment the biologically active agent is a therapeutic agent for treating diabetes. In yet another embodiment the therapeutic agent is an agent for treating a central nervous system disorder. In one embodiment agents for treating a central nervous system disorder include agents for treating neurodegenerative disease/disorders, agents used to treat spinal cord injury and agents for promoting neuronal regeneration. In still a further embodiment the agent is an agent for treating a renal disorder. In another embodiment the agent is an agent for treating a gastrointestinal disorder. In yet another embodiment the agent is an agent for treating an endocrinal disorder.

In one embodiment the agent for treating a disease associated with a coagulation disorder, such as cardiovascular disease, a vascular condition or a cerebrovascular condition, is an anticoagulant, an antithrombotic an anti-platelet agent, a fibrinolytic agent, a lipid reducing agent or a direct thrombin inhibitor. In one embodiment the anticoagulant is warfarin, coumadin, dicumarol, phenprocoumon, acenocoumarol, ethyl biscoumacetate or an indandione derivatives. In another embodiment the antithrombotic agent is a thrombolytic agent. In some embodiments the thrombolytic agent is plasminogen, $a_2$-antiplasmin, streptokinase, antistreplase, tissue plasminogen activator (tPA) or urokinase.

In one embodiment the agent for treating a central nervous system disorder is a benzodiazepine, a benzodiazepine antagonist, a barbiturate, buspirone, chloral hydrate, ethchlorvynol, ethinamate, hydroxyzine, meprobamate, paraldehyde, zaleplon, zolpidem, a therapeutic for acute alcohol withdrawal syndrome; a therapeutic for the prevention of alcohol abuse, a therapeutic for acute methanol or ethylene glycol poisoning, an anti-epileptic drug, a general anesthetic, a local anesthetic, a skeletal muscle relaxant, a spasmolytic, an anti-Parkinsonism agent, a movement disorder agent, an antipsychotic agent, a mood stabilizer, an anti-depressant agent, a second or third generation agent, a selective serotonin reuptake inhibitor, a monoamine oxidase inhibitors, an opioid analgesic or antagonist, an opioid analgesic, an opioid antagonist or an antitussive. In another embodiment the agent is an agent for promoting neuronal regeneration. In still another embodiment the agent for promoting neuronal regeneration is a nerve growth factor, neurotrophic factor, such as NGF, BDNF, GDNF, LIF, CNTF, or neural stem cell replacement therapy.

In another embodiment the agent is an agent for treating asthma. In one embodiment such agents include steroids, PDE-4 inhibitors, bronchodilator/beta-2 agonists, K+ channel openers, VLA-4 antagonists, neurokin antagonists, TXA2 synthesis inhibitors, xanthanines, arachidonic acid antagonists, 5 lipoxygenase inhibitors, thromboxin A2 receptor antagonists, thromboxane A2 antagonists, inhibitor of 5-lipox activation proteins, and protease inhibitors. In another embodiment the agent is a bronchodilator. In one embodiment the bronchodilator is salmeterol, salbutamol, albuterol, terbutaline, D2522/formoterol, fenoterol, bitolterol, pirbuerol methylxanthines or orciprenaline.

In another embodiment the agent is an antidepressant. In one embodiment the antidepressant is a monoamine oxidase inhibitor (MAOI), tricyclic or serotonin inhibitor. In another embodiment antidepressants include, but are not limited to, Iproniazid, Prozac, Paxil, Celexa, Lexapro, Wellbutrin, Luvox, Paxil and Zoloft.

In still another emodient the agent is an antihypertension agent. In one embodiment the agent is a calcium channel blockers (CCB) (e.g. Amlodipine), beta-blocker (e.g. Bisoprolol), Angiotensin converting enzyme inhibitor (ACEI) (e.g. Lisinopril or Accupril), alpha-blocker (e.g. Doxazosin) or Thiazide (Bendrofluazide).

In another embodiment the agent is an agent for treating a gastrointestinal disorder. In one embodiment the agent is an anti-ulcer agent. In another embodiment the anti-ulcer agent includes H2-blockers, acid pump inhibitors and mucosal protective medications.

In another embodiment the agent is an agent for treating atherosclerosis. In one embodiment such an agent is Advicor® (niacin/lovastatin), Altoprev™ (lovastatin), Caduet® (amlodipine beslate/atorvastatin calcium), Cholox (a blend of cholesterol and homocysteine-lowering factors), Inderal® (propanolol hydrochloride), Lescol® (fluvastatin sodium), Lipitor® (atorvastatin calcium), Lofibra® (fenofibrate capsules), Niaspan® (niacin extended-release), Pravachol® (pravastatin sodium) or Mevacor® (lovastatin).

In another embodiment the agent is an agent for treating arteriosclerosis. In one embodiment such an agent is Lofibra® (Fenofibrate), Ortho-cept® (desogestrel and ethinyl estriadol), or Ortho Evra® (norelgestromin/ethinyl estradiol).

In another embodiment the agent is a diuretic. In one embodiment the diuretic is Dichlorphenamide, methazolamide, bendroflumethiazide, or polythiazide.

In still another embodiment the agent is a hormone therapy. In one embodiment the hormone therapy is Combipatch® (estradiol/norethindrone acetate), Androgel® (testosterone gel), Arimidex® (anastrozole), Casodex® (bicalutamide), Claripel™ (hydroquinone USP), Cytomel® (liothyrone sodium), Delatestryl® (testosterone enanthate), or Epiquine™ (hydroquinone USP).

In still another embodiment the agent is an agent for treating urinary tract infection. In one embodiment the agent is trimethoprim (Trimpex), trimethoprim/sulfamethoxazole (Bactrim, Septra, Cotrim), amoxicillin (Amoxil, Trimox, Wymox), nitrofurantoin (Macrodantin, Furadantin), ampicillin, tetracycline, trimethoprim/sulfamethoxazole (TMP/SMZ), doxycycline, quinolines ofloxacin (Floxin), norfloxacin (Noroxin), ciprofloxacin (Cipro) or trovafloxin (Trovan).

In yet another embodiment the agent is an antidiabetic agent. In one embodiment such an agent is Avandamet, Fortamet, Metaglip, a Glucosidase inhibitor, Insulin such as Humalog® (insulin lispro) Humulin, Novolin, Lantus, or Apidra, a Meglitinide such as Prandin or Starlix, a Sulfonylurea, a Thiazolidinedione such as Actos® (pioglitazone hydrochloride), Avandamet® (rosiglitazone maleate and metformin hydrochloride), or Avandia® (rosiglitazone maleate).

In still another embodiment the agent is an agent for treating an ocular disorder. In one embodiment such an agent is a steroidal eye drop, topical steroid such as Vexol, a regional injecton steroid such as Triamcinolone acetonide, an antibiotic such as cyclosporine A, an anti-VEGF2 therapy, NOVASORB™ or EYEJECT™.

In still another embodiment the agent is an antiangiogenic agent. In one embodiment the antiangiogenic agent is tetrathiomolybdate, N-acetylcysteine (NAC), a MMP-2 (matrix-metalloproteinase 2) inhibitor, a MMP-9 (matrix-metalloproteinase 9) inhibitor, a COX-II (cyclooxygenase II) inhibitor, a COX-II inhibitor including CELEBREX™ (celecoxib), valdecoxib, rofecoxib, parecoxib, deracoxib, SD-8381, ABT-963, etoricoxib, lumiracoxib, BMS-347070, NS-398, RS 57067 or meloxicam.

In yet another embodiment the agent is a dermatologic agent. In one embodiment the dermatologic agent is tretinoin (Retin A, Avita), adapalene (Differin), tazarotene (Tazorac), azelaic acid, a keratolytic agent, an antibiotic, benzoyl peroxide, a sulfone, an antiandrogen/estrogen or a glucocorticoid.

In another aspect of the invention compositions are provided which comprise one or more intercellular junction disruption agents and one or more biologically active agents. In one embodiment the compositions provided include pharmaceutically acceptable carriers. Methods of using the compositions are also provided.

In another embodiment of the invention the compositions provided are mixed with a generally recognized as safe agent (GRAS). In some embodiment the GRAS is tween, glycerin, Glutamic acid, Glutamic acid hydrochloride, Hydrochloric acid, Phosphoric acid, Sodium acid pyrophosphate, Aluminum sulfate, Aluminum ammonium sulfate, Methylcellulose or glycerin.

In another aspect of the invention the biologically active agent is attached to the intercellular junction disruption agent. In yet another aspect of the invention the biologically active agent and/or the intercellular junction disruption agent is attached to a targeting molecule. In one embodiment the targeting molecule targets a particular cell barrier. The cells/cell barrier can be any cells/cell barrier as provided herein. The targeting molecules can be any molecule that preferentially targets a particular molecule associated with a particular cell/cell barrier. Targeting molecules can in some embodiments be used to target disease markers. In one embodiment the disease marker is a cancer antigen. In another embodiment the cell barrier is the blood-brain barrier and the targeting molecule targets the blood-brain barrier.

In one embodiment the targeting molecule is an antibody (e.g., a monoclonal antibody (mAb) to a cancer antigen or a receptor present on the blood-brain barrier). In one embodiment the targeting molecule is an antibody, such as monoclonal antibody OX26, to transferrin receptor (present in the blood-brain barrier as well as the liver in higher amounts than in other tissues). In another embodiment the targeting molecule is a monoclonal antibody to PGP1 (P-glycoprotein 1).

In another aspect of the invention compositions and methods are provided for modulating cellular processes and molecules involved in controlling intercellular junctions. In one embodiment methods and compositions are provided for altering syndecan shedding. In another embodiment such methods and compositions for altering syndecan shedding to control intercellular junctions include the use of EGTA, Hep I, Hep III or cABC. In another embodiment the compositions and methods can be used for altering integrin (e.g., αV, β1 and/or β3). In another embodiment the compositions and methods provided can be used to control FAK phosphorylation and/or localization, CD44 properties (e.g., localization), the wnt pathway or calcium flux.

In one embodiment the polysaccharide and/or polysaccharide-degrading enzymes for use in the compositions and methods provided are not in a food. In another embodiment the polysaccharide and/or polysaccharide-degrading enzymes are isolated.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE FIGURES

FIG. 1 shows the uptake of unfractionated heparin into the lungs (FIG. 1A) and trachea (FIG. 1B) of mice.

FIG. 2 shows the transport of ardeparin sodium and ardeparin calcium powder (FIG. 2A) and sodium ardeparin powder and solution (FIG. 2B) through calu-3 human lung adenocarcinoma epithelial cells.

FIG. 3 illustrates the effect of unfractionated heparin sodium powder on the Trans Epithelial Electrical Resistance (TEER) in calu-3 human lung adenocarcinoma epithelial cells.

FIG. 4 depicts the effect of heparinase III, chondroitinase ABC lyase, heparinase I and EGTA on the tight junctional protein zona occludens-1 (ZO-1) localization in 16HBE14O-human virally transformed bronchial epithelial cells. The figure also shows untreated cells as control.

FIG. 5 shows the immunofluorescence detection of ZO-1 in calu-3 (human lung adenocarcinoma) and 16HBE14O- (virally transformed human bronchial epithelial) cells after treatment with glycosaminoglycan-degrading enzymes.

FIG. 6 shows the effect of unfractionated heparin powder on actin cytoskeletal filaments and tight junctional protein ZO-1 in calu-3 human lung adenocarcinoma epithelial cells.

FIG. 7 shows the effect of unfractionated heparin powder on the phosphorylation of tight junctional protein ZO-1.

FIG. 8 illustrates the influence of unfractionated heparin solution (FIG. 8A) and unfractionated heparin powder (FIG. 8B) on intracellular calcium levels in calu-3 human lung adenocarcinoma epithelial cells.

FIG. 9 shows the results of the proteoglycan shedding experiments. FIG. 9B shows the effect of the same treatment on the shedding of syndecan-4 proteoglycan. Endogenous shedding of the proteoglycan in untreated cells is also shown as a control in both figures.

FIG. 10 describes the effect of heparinase III, chondroitinase ABC, heparinase I and EGTA on phosphorylation levels of Focal Adhesion Kinase (FAK) in 16HBE14O-human virally transformed bronchial epithelial cells.

DETAILED DESCRIPTION

Figure 9A:
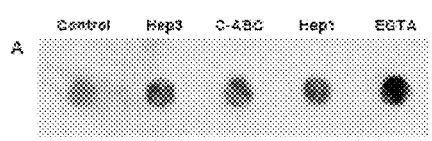
FIG. 9A shows syndecan-1 shedding in response to treatment of 16HBE14O-human virally transformed bronchial epithelial cells with heparinase III, chondroitinase ABC, heparinase I and EGTA.

The transport of macromolecules and drugs occurs either via the transcellular or the paracellular pathway. Transcellular transport, is the movement of substances across the epithelial cell membrane, diffusion through the cytosol, and exit across the membrane on the other side. Since non-invasive routes of drug delivery (which mainly includes oral, nasal, transdermal, ocular, rectal and other non-parenteral routes) are receiving increasing attention, transepithelial transport mechanisms are gaining more and more importance. Paracellular transport, on the other hand, is the movement of substances through the epithelium by diffusion between adjacent cells of the epithelium. This movement is, however, limited by tight junctions. Modulating tight junctions is a very important target for drug delivery. Potential targets could be the blood-brain barrier (BBB) that includes highly organized endothelial tight junctions, the upper airway, trachea and lungs, the skin, the sublingual membrane and the gastrointestinal tract.

Several methods of modulating the tight junction permeability have been described. U.S. Pat. No. 6,312,686 describes the modulation of tight junction permeability in endothelial cells with a vanadium agent that affects tyrosine phosphorylation of proteins. The modulation of tight junctions with this agent, however, can exert non-specific adverse effects. U.S. Pat. No. 6,610,653 describes a method of increasing the paracellular permeability of insulin powder by using lipid-based enhancers. U.S. Pat. No. 6,252,045 describes a method of enhancing drug absorption though epithelial and endothelial cells by using occludin inhibitors. U.S. Pat. No. 6,723,700 discusses the polypeptide sequences and methods that can modulate claudin-mediated cell adhesion and thus increase blood-brain barrier permeability.

Provided herein are compositions and methods for modulating intercellular complexes and improving drug delivery across permeability barriers. Therefore, agents that are capable of modulating intercellular junctions and hence modulate the barrier function of epithelial cells are also provided. The modulating agents described include polysaccharides, such as polysaccharides that belong to the glycosaminoglycan family, and enzymes that modulate cell surface glycosaminoglycan activity. Preferably, in some embodiments, the polysaccharides are linear. The methods described herein reversibly inhibit tight junction function and thus facilitate delivery of biologically active molecules to certain tissues or tumors.

In one aspect of the invention compositions and methods for transiently disrupting intercellular junctions are provided. The methods include the step of contacting cells with one or more polysaccharides, polysaccharide-degrading enzyme or both in an amount effective to transiently disrupt one or more of the intercellular junctions. As used herein, a "polysaccharide" is a polymer composed of monosaccharides linked to one another. In many polysaccharides the basic building block of the polysaccharide is actually a disaccharide unit, which can be repeating or non-repeating. Thus, a unit when used with respect to a polysaccharide refers to a basic building block of a polysaccharide and can include a monomeric building block (monosaccharide) or a dimeric building block (disaccharide). The term polysaccharide is also intended to embrace an oligosaccharide. In some embodiments the polysaccharide is a digestible polysaccharide. The term "digestible" is meant to mean that the polysaccharide can be digested by digestive enzymes. The term is also meant to include polysaccharides that have already been digested. The polysaccharides, in some embodiments, are glycosaminoglycans (GAGs). In some embodiments the glycosaminoglycans are not associated with proteoglycans. In another embodiment the polysaccharide and/or polysaccharide-degrading enzymes for use in the compositions and methods provided are not in a food and/or found in a food for consumption. In another embodiment the polysaccharide and/or polysaccharide-degrading enzymes are isolated. The biologically active molecules provided herein can also be isolated.

An "isolated" molecule is a molecule that is substantially pure and is free of other substances with which it is ordinarily found in nature or in vivo systems to an extent practical and appropriate for its intended use. In particular, the molecular species are sufficiently pure and are sufficiently free from other biological constituents of host cells so as to be useful in, for example, producing pharmaceutical preparations. Because an isolated molecular species of the invention may be admixed with a pharmaceutically-acceptable carrier in a pharmaceutical preparation, the molecular species may comprise only a small percentage by weight of the preparation. The molecular species is nonetheless substantially pure in that it has been substantially separated from the substances with which it may be associated in living systems.

Figure 11:
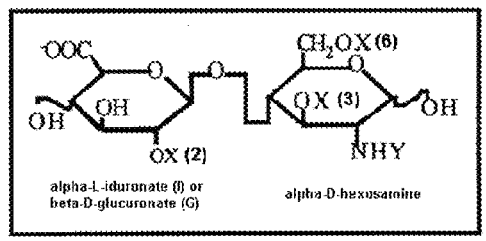
FIG. 11 shows the structure of heparan-sulfate glycosaminoglycans.

Heparan sulfate like glycosaminoglycans are chemically complex and heterogeneous polysaccharides because the HSGAG/HLGAG side chains can vary in terms of the number of disaccharide repeat units. Within the disaccharide repeat there are four potential sites for chemical modification. The basic disaccharide repeat unit of HLGAG is a uronic acid [α-L-iduronic acid (I) or $^3$-D-glucuronic acid (G)] linked 1,4 to α-D-hexosamine (H) (FIG. 11). The chemical modifications that could take place within each disaccharide repeat are: primary sulfation at the 2-O, 3-O, 6-O (represented in FIG. 11 as X(2), X(3) and X(6), respectively) and N sulfation or acetylation (marked as Y in FIG. 11). Together, the four different modifications give rise to $2^4=16$ different possible structures for a disaccharide repeat with a particular uronic acid isomer. Since there are two uronic acid isomers: I and G, there could be 16×2=32 different plausible disaccharide units for HLGAGs. Different combinations of the 32 building blocks yield tetra-, hexa-, or longer saccharides (Venkatraman et al, 1999).

Figure 12:
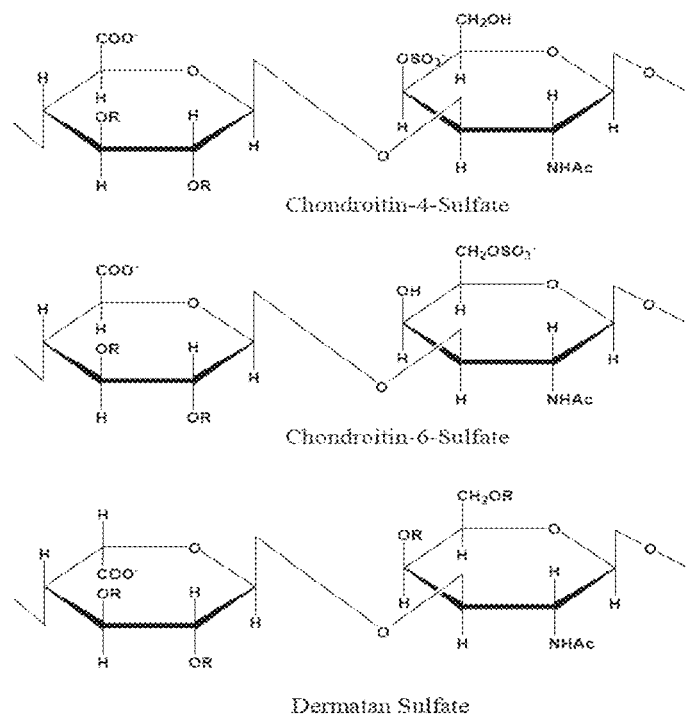
FIG. 12 shows the structure of chondroitin sulfate glycosaminoglycans and dermatan sulfate glycosaminoglycans.

Glycosaminoglycans also include galactosaminoglycans (GalAGs). Galactosaminoglycans are one of four classes of structurally complex linear polysaccharides called glycosaminoglycans (GAGs). GalAGs are composed of disaccharide repeat units of uronic acid [α-L-iduronic (IdoA) or β-D-glucuronic (GlcA)] (1→3) linked to N-acetyl-D-galactosamine (GalNAc). These basic disaccharide units are linearly associated via β(1→4) linkages to form polymers of chondroitin sulfate (CS) or dermatan sulfate (DS). The uronic acids in CS are exclusively GlcA; with DS, epimerization at the C-5 position of the uronic acid moiety during biosynthesis results in a mixture of IdoA and GlcA epimers. Biosynthesis of CS and DS also involves sulfation of the sugar backbone at various positions which generates diversity in their oligosaccharide sequences. Chondroitin sulfate is commonly O-sulfated at the C-4 of the galactosamine (chondroitin-4-sulfate, C4S or CSA) or the C6 of the galactosamine (chondroitin-6-sulfate, C6S or CSC). Other modifications in CS, such as 2-O or 3-O sulfation of the GlcA moiety, occasionally occur. In the case of DS, O-sulfation at C-4 of GalNAc is a common modification; O-sulfation at C-6 of GalNAc and C-2 of the IdoA are rare. FIG. 12 provides example structures of chondroitin sulfate and dermatan sulfate.

In some embodiments the glycosaminoglycan does not possess anticoagulant properties. Therefore, in some embodiments the glycosaminoglycan is one that lacks an AT III binding domain or a portion thereof. In some embodiments the glycosaminoglycan is a heparin lacking its anticoagulant portions, such as a complete AT III binding domain. Therefore, these glycosaminoglycans can include heparins that contain only a portion of the AT III binding domain or those that do not contain the AT III domain whatsoever. Glycosaminoglycans, such as heparin, can be manipulated to remove the anticoagulant portions, such as the AT III binding domain, with no more than routine methods known in the art.

Glycosaminoglycans are complex polymers based on repeated disaccharide units consisting of an uronic acid and a hexosamine. This group of polysaccharides includes: heparin, heparan sulfate, chondroitin sulfates, dermatan sulfate, keratan sulfate, low molecular weight heparins (LMWHs), hyaluronic acid and salts, derivatives and analogs thereof. In one embodiment the glycosaminoglycan is heparin. The glycosaminoglycan can also be, in some embodiments, the sodium salt of heparin, ardeparin, such as ardeparin sodium, UFH, etc. Glycosaminoglycans also include heparin/heparan sulfate-like glycosaminoglycans (HLGAGs/HSGAGs), which are complex acidic polysaccharides present both within the ECM that surrounds cells and at the cell surface as protein-carbohydrate conjugates (termed proteoglycans). HSGAG proteoglycans are found at the surface of virtually every cell type, where they act as important biological mediators of various cell-related events such as proliferation, morphogenesis, adhesion, migration, and cell death (apoptosis) (Sasisekharan R et al., 2000). At a fundamental level, the role of these complex polysaccharides has become a very important dimension in our understanding of biological processes in the post-genomic era. Given their role in fundamental cellular events, HSGAGs have been found to be important regulators of biological processes ranging from embryogenesis (Perrimon N et al., 2000) to hemostasis (Rosenberg R. D et al., 1997) as well as in the pathophysiology of disease states. Chondroitin sulfate glycosaminoglycans present on the cell surface and in the ECM are also implicated in several biological processes such as wound healing and cartilage formation. In some embodiments the glycosaminoglycans for use in the methods and compositions provided are not chondroitin sulfates (including fragments thereof) generated by the action of cABC I. As used herein "cABC I-generated" chondroitin sulfates include any chondroitin sulfate that is produced by the activity of cABC I. These can be chondroitin sulfates that are modified in any way by the activity of the enzyme. Modifications include cleavage and alteration.

The observations described herein show that polysaccharides can disrupt intercellular junctions. For example, the observations describe the involvement of heparan sulfate and chondroitin sulfate cell surface proteoglycans in intercellular junction modulation. The basic structure of all proteoglycans (PGs) includes a core protein and several branched chains of glycosaminoglycans (GAGs). There are two major families of membrane-bound proteoglycans, the syndecans and the glypicans. Heparan sulfate proteoglycans (HSPGs) have been implicated in a wide variety of biological processes such as growth factor signaling, cell adhesion, wound healing, and tumor metastasis. The prototype cell surface HSPG, syndecan-1, was first identified as a developmentally regulated type-I transmembrane protein that bound extracellular-matrix (ECM) components to epithelial cells. By way of their heparan sulfate (HS) chains, syndecans and glypicans can bind a wide variety of soluble and insoluble extracellular ligands (Bernfield M et al., 1999). All adherent cells express at least one syndecan and some express multiple syndecans.

The syndecan family of proteoglycans has been widely implicated in the maintenance of epithelial morphology and formation of focal contacts. The results of the study of this family of proteoglycans is described below in the Examples. These cell surface proteoglycans have a membrane bound core protein, the extracellular domain (ectodomain), which is attached to glycosaminoglycan side chains. The syndecan family of proteoglycans belongs to the HSPG family. The core protein of syndecans contains eight multifunctional domains. The ectodomain of the syndecan family has regions for glycosaminoglycan attachment, cell interaction, proteolytic cleavage and oligomerization (Bernfield M et al., 1999). This ectodomain of the syndecans is constitutively shed. Ectodomain shedding is a proteolytic mechanism of releasing the extracellular domains of cell surface proteins as soluble ectodomains. Ectodomain shedding is mediated by peptide hydroxamate-sensitive metalloproteinases, which are collectively called sheddases or secretases (J Schlondorff et al., 1999). Ectodomain shedding can also be affected by several external factors such as stress and activation of several signaling pathways (Bernfield M et al., 1999).

Cell surface heparan sulfate proteoglycans (HSPGs) can enhance the formation of receptor-ligand signaling complexes, can direct ligands into the cell for degradation or recycling, and can themselves be shed from the cell surface as soluble PGs. This shedding can be part of HSPG turnover but can also be accelerated by effectors, generating potent soluble HSPG inhibitors and cells that are less responsive to ligands (Bernfield M et al., 1999). The exact mechanism of syndecan shedding remains largely unknown, but ectodomain shedding of the syndecans appears to contribute to diverse pathophysiological events such as host defense, wound healing, arthritis, and Alzheimer's disease (Kiessling, L. L. et al 1998, Hooper, N. M et al, 1999, Merlos-Suarez, A et al, 1999). Shedding of syndecan-1 has also been implicated in infection. For instance, *Pseudomonas aeruginosa* accelerates shedding to enhance its infectivity both in vivo and in vitro (Park P W et al., 2000, Park P W et al, 2001). The cleavage process has been ascribed to sheddases, secretases, or convertases, which are known to be zinc-dependant metalloproteinases (Arribas, J et al, 1996, Fitzgerald M L et al., 2000).

HSGAGs play an important role in maintaining the structure and function of the tight junctions. It is demonstrated herein that the addition of agents that modify the HSGAGs of the extracellular matrix and glycosaminoglycan side chains of cell surface proteoglycans, modulate tight junctional permeability. These agents in some embodiments modify syndecans and/or controls its shedding. In addition, the complex linear polysaccharide heparin, which has been implicated in several biological functions, has now been found to be a modulator of tight junction permeability. Heparin is a mixture of sulfate-containing mucopolysaccharides with a strongly acidic reaction and a large electronegative charge. It is a glycosaminoglycan composed of long chains of alternating D-glucuronic acid and N-acetyl-D-glucosamine sugar residues, which undergo a series of chemical modifications, primarily sulfation, leading to the formation of unique pentasaccharide sequences. Heparin polysaccharides are heterogeneous in length and vary in mass from 5000 to 30,000 kDa (Majerus P W et al., 1996) and is a natural product, mainly used as an anticoagulant and to prevent formation of blood clots (after surgery and in other settings) and in circumstances to help dissolve blood clots already formed (deep vein thrombosis, pulmonary embolism, and other situations involving excessive blood clotting).

Initial in vivo experiments showed that inhalation of the unfractionated heparin powder (UFH) caused the absorption of the polysaccharide into the trachea and lungs of mice (FIG. 1A and FIG. 1B). It is believed that the polysaccharides were transported by paracellular mechanisms rather than transcellular mechanisms as few hydroxyl groups on each of the monosaccharide residues in heparin may be sulfated giving rise to a polymer that is highly negatively charged. The average negative charge of individual saccharide residues is about 2.3 (Majerus P W et al., 1996). With such a high surface negative charge, it is not possible for the polysaccharide to be transported through transcellular mechanisms (through the cell membrane) due to the electrostatic repulsion between the polysaccharide and the negatively charged cell membrane.

To test if the UFH indeed caused a disruption in the function of the intercellular junctional complex, calu-3 cells (human lung adenocarcinoma epithelial cells) were chosen as a model system. Trans Epithelial Electrical Resistance (TEER) measurements, which measure the integrity of an epithelial monolayer and hence the permeability of the tight junctions, were done on the calu-3 cells before and after treatment with UFH. It was found that there was a marked decrease in the TEER with time after UFH addition in a concentration dependant manner (FIG. 3). This observation was the first proof that UFH caused an increase in permeability of tight junctions in epithelial cells.

Several other experiments were done to validate the above results. The localization of the tight junction protein zona occludens-1 (ZO-1) was studied before and after the addition of UFH powder. ZO-1, with a molecular weight of about 220 kDa, is a peripheral membrane phosphoprotein that is expressed both in epithelial and endothelial cells. The tight junction protein is located at the cytoplasmic membrane surface precisely at the sites of cell-cell contacts (E Willott et al., 1993). It is known that this protein is involved in maintaining the integrity of the tight junctions, and thus a disruption of ZO-1 indicates an increase in the permeability of tight junctions. Visual investigation of the localization of ZO-1 in calu-3 cells using confocal microscopy has shown a disruption in the ZO-1 pattern after addition of UFH powder (FIG. 6). Actin filaments have been also implicated in the structural and functional organization of the tight junction (Madara J L et al., 1987), and ZO-1 has been shown to bind directly to F-actin in vitro (Masahiko Itoh et al., 1997). Thus, a disruption in actin filaments would correspond with a disruption in tight junction integrity. The experiments described herein have shown a disruption of actin filaments in calu-3 cells after UFH addition (FIG. 6). Further, it is known that an increase in tyrosine phosphorylation of ZO-1 causes an increase in intercellular permeability in epithelial cells (Atkinson K J et al., 2001). It has now been observed that addition of UFH powder causes an increase in ZO-1 phosphorylation in about 10 minutes after the sugar addition (FIG. 7). All these results show that UFH causes an increase in tight junction permeability in epithelial cells.

Another example of a modulator of transepithelial permeability provided is ardeparin, such as ardeparin sodium powder. Ardeparin is a low molecular weight heparin (LMWH)

that is also used as an anticoagulant. LMWHs are produced artificially by various methods of depolymerizing native heparin, which yield chemically distinct products in terms of end group polysaccharides and molecular weight distribution (Lin P et al., 2001). It has now been shown that ardeparin sodium powder was effectively transported through calu-3 cell monolayers (FIG. 2A), ardeparin sodium solution or ardeparin calcium was not transported effectively (FIG. 2A and FIG. 2B).

The cells have been found to completely recover from the effects of UFH in about 6-8 hours (similar results were observed for the enzymes and are described below). Therefore, the effect of the compositions of polysaccharides and/or polysaccharide degrading enzymes provided can be transient and short term. The compositions and methods provided can be used, therefore, to transiently disrupt one or more intercellular junctions for 1, 2, 5, 10, 15, 20, 30, 60 or more minutes. The compositions and methods can also be used to transiently disrupt one or more intercellular junctions for 1, 2, 3, 4, 5, 6, 7, 8, 9, 10, 12, 15, 20, 24, 30, 36 or more hours. In one embodiment the compositions and methods are used to transiently disrupt one or more intercellular junctions anywhere from 1 minute to 10 hours. As used herein to "transiently disrupt" means to temporarily disturb one or more intercellular junctions such that the junction(s) no longer links the cells and/or are more permeable than in the native state or in the presence of an intercellular junction opening inhibitor (i.e., any agent that can inhibit intercellular junction disruption and/or decrease intercellular permeability). Examples of intercellular junction opening inhibitors are provided below. As used herein "intercellular junction" includes the points where cells are joined and/or the areas of the cells in between which the passage of molecules is inhibited or retarded as compared to the native state or to the passage of the molecules in the presence of an intercellular junction opening inhibitor. Intercellular junctions include tight junctions, adherens junctions, desmosomes, etc. In some instances in the literature "intracellular" has been used instead of "intercellular".

In addition to polysaccharides from natural sources, the polysaccharides of the invention also include molecules that are biotechnologically prepared, chemically modified and synthetic. The term "biotechnological prepared" encompasses polysaccharides that are prepared from natural sources of polysaccharides which have been chemically modified. This is described for example in Razi et al., Bioche. J. Jul. 15, 1995; 309 (Pt 2): 465-72 and in Yates et al., Carbohydrate Res Nov. 20, 1996; 294:15-27, and is known to those of skill in the art. Synthetic polysaccharides are also well known to those of skill in the art and are described in Petitou, M. et al., Bioorg Med Chem Lett. Apr. 19, 1999; 9(8):1161-6. Polysaccharides can also be produced from the interaction of naturally occurring or non-naturally occurring polysaccharides, such as those described above, with polysaccharide-degrading enzymes. Any polysaccharide that results from the interaction with one or more polysaccharide-degrading enzymes, wherein the enzyme cleaved or somehow modified the polysaccharide, is referred to herein as a "polysaccharide fragment".

The polysaccharide of the compositions and methods described herein can include LMWH. Several LMWH preparations are commercially available, but, LMWHs can also be prepared from heparin, using e.g., glycosaminoglycan-degrading enzymes. Commercially available LMWH include, but are not limited to, enoxaparin (brand name Lovenox; clexane by Rhone-Poulenc Rorer), dalteparin (Fragmin, Pharmacia and Upjohn), certoparin (Sandobarin, Novartis), ardeparin (Normiflo, Wyeth Lederle), nadroparin (Fraxiparine, Sanofi-Winthrop), pharnaparin (Fluxum, Wassermann), reviparin (Clivarin, Knoll AG), and tinzaparin (Innohep, Leo Laboratories, Logiparin, Novo Nordisk).

Like the polysaccharides provided, one or more polysaccharide-degrading enzymes can also be used to transiently disrupt intercellular junctions. A "polysaccharide degrading enzyme" as used herein is any enzyme which cleaves or somehow modifies a polysaccharide. Preferably, the polysaccharide-degrading enzyme is a polysaccharide lyase that catalyzes cell surface glycosaminoglycans. Polysaccharide-degrading enzymes include, therefore, glycosaminoglycan-degrading enzymes. A "glycosaminoglycan-degrading enzyme" is any enzyme that cleaves or somehow modifies a glycosaminoglycan. Glycosaminoglycan-degrading enzymes include but are not limited to chondroitinases (e.g. chondroitinase ABC I, chondroitinase AC, chondroitinase B, chondroitinase C, chondroitinase ABC II), chondro-4-sulfatase, chondro-6-sulfatase, hyaluronate lyase, heparinase-I, heparinase-II, heparinase-III, keratanase, D-glucuronidase, delta 4, 5-glycuronidase and L-iduronidase, 2-O sulfatase, sulfotransferases, modified versions of these enzymes, variants and functionally active fragments thereof.

Heparinases and chondroitinases are enzymes that cleave heparan sulfate glycosaminoglycans and chondroitin sulfate glycosaminoglycans (both present in the ECM or at the cell surface), respectively, with a very high degree of specificity (Godavarti R et al., 1996a). Heparinases are lyases that depolymerize HLGAGs/HSGAGs in a sequence specific fashion. Three heparinases, heparinase I, II and III have been isolated. Though heparinase I and III are both cloned from *Flavobacterium heparinum*, they do not have similar sequence homology, and they are also specific to different sulfation sites of the polysaccharide. Heparinase I cleaves the more sulfated regions, while heparinase III cleaves the less/unsulfated regions of the polysaccharides (Godavarti R et al., 1998). Heparinase I cleaves HSGAGs at sites with an O-sulfated L-iduronic linkage (i.e., heparin-like regions) (Godavarti R et al., 1996a). Conversely, heparinase III requires primarily an unsulfated D-glucuronic moiety (i.e., heparan sulfate-like regions) (Godavarti R et al., 1998). Chondroitinases digest chondroitin sulfates and belong to the chondroitinase lyase family that includes chondroitinase A, chondroitinase B, chondroitinase C, chondroitinase AC and chondroitinase ABC (e.g., cABC I, cABC II). Chondrotinase ABC cleaves all types of chondroitin sulfates. The other enzyme that was found to affect epithelial permeability is chondroitinase ABC that is obtained from *Proteus vulgaris*.

It was observed that incubation of 16HBE14O-human virally transformed bronchial epithelial cells and calu-3 (human lung adenocarcinoma) cells with glycosaminoglycan-degrading enzymes caused a disruption of ZO-1, which was observed using confocal microscopy (FIGS. 4 and 5). It was also observed that different enzymes affected epithelial permeability to different extents. In 16HBE14O-cells, Hep I and cABC had more pronounced effect than Hep III. On the other hand, Hep III and cABC had more effect than Hep I in calu-3 cells. The effects of these enzymes and UFH powder and solution were also studied in two other cell lines, namely, the caco-2 (human colon adenocarcinoma) and MCF-7 (human mammary cancer) cells. In these tumor cell lines it was observed that Hep III had more effect on tight junction disruption than cABC and Hep I. These results indicate that the enzymes influence intercellular junctions to different extents depending upon the cell type. EGTA, which was used as a positive control, caused a disruption of the junctional complex in all the cell lines, and UFH also increased epithelial permeability in all of these cell lines. Heat inactivated enzymes, however, did not have any effect on these cells lines, and all of the cell lines recovered from the effect of the different treatments (enzyme, EGTA and UFH) in about 8 hours.

It has now also been observed that the addition of hep I, hep III, cABC causes syndecan-1 ectodomain shedding (FIG. 9A). The different enzymes cause shedding of the ectodomain of syndecan-1 to different extents in the two cell lines. Interestingly, the enzymes did not cause an increase in syndecan-4 ectodomain shedding (FIG. 9B). This shedding could be important in controlling tight junction permeability. An increase in shedding seems to correlate with opening of the junctions. It is known that syndecan interacts with the actin cytoskeleton and modulates the reorganization of the actin filaments (Bernfield M et al., 1999). The reorganization of the actin filaments due to syndecan shedding could cause the opening of the junctions. Another likely possibility to explain the role played by syndecan in tight junction modulation is that the PDZ (post synaptic density protein (PSD)-95, Discs large (Dlg) and ZO-1) domain of syndecan could interact with the PDZ domain of ZO-1, and the shedding could affect this interaction leading to the opening of the junctions.

It can be speculated that the enzymes cause syndecan shedding by PKC (protein kinase C) activation. This is unlikely to be a direct effect, but it is possible that the enzymes cause cleavage of the HS and chondroitin sulfate (CS) side chains resulting in an imbalance in intra and extra cellular calcium levels which causes the activation of PKC (which is involved in calcium signaling). It is known that activated PKC causes activation of a matrix metalloproteinase (sheddase) that causes syndecan shedding (Fitzgerald M L et al., 2000).

An alternate mechanism for the shedding could be the release of active sheddase (which could be attached to the HS and CS side chains of the syndecan) as a result of enzymatic cleavage of the side chains of syndecan-1. In addition, it is also likely the enzymes independently cause a change in the oligomerization or phosphorylation state of syndecan-1 and -4. This effect could also be a cause or a result of the shedding. It has been shown recently that syndecan-1 and -4 have a coreceptor binding domain and that they might regulate tumor cell functions like cell adhesion and invasion by such coreceptor interactions with integrins (Beauvis and Raprae-ger, 2003). Other researchers have shown the colocalization of beta-I integrin with occludin (an intercellular tight junctional protein) in MDCK cells (Madin-Darby Canine Kidney cells). Based on these observations, it is likely that the integrins, syndecans and ZO-1 could probably be interacting with one another either directly or indirectly and that syndecan shedding or changes in oligomerization state/phosphorylation state could affect interaction with the integrins which could in turn trigger downstream signaling events resulting eventually in the opening of junctions.

Experiments were also done to study the changes in the phosphorylation of Focal Adhesion Kinase (FAK, which is downstream of integrins) upon enzyme addition. Interestingly, in the 16HBE14O-cells an increase in phosphorylation of FAK was observed at different levels with the different enzyme treatments (FIG. 10). It is known that syndecan-4 is involved in the focal adhesion complex, and it directly interacts with FAK. Paxillin (which also binds to syndecan-4) is known to interact with FAK and mediate interactions with several structural and regulatory proteins important for coordinating changes in the actin cytoskeleton. Thus, it is possible that a change in the oligomerization state of syndecan-4 upon enzyme addition causes an increase in phosphorylation of FAK either directly or through the integrins, which eventually leads to the opening of the tight junctions by causing a remodeling of the actin filaments.

All of the results presented show that the transient disruption of the intercellular tight junctions can result in the increased absorption of the polysaccharides and/or polysaccharide-degrading enzymes described herein. These polysaccharides and polysaccharide-degrading enzymes are also referred to as "intercellular junction disruption agents". Methods for increasing the absorption of these molecules are, therefore, provided. The transient disruption of intercellular junctions can also facilitate the passage of biologically active molecules through the otherwise impermeable cell barriers, such as the epithelial or endothelial barriers. Provided herein, therefore, are compositions and methods for increasing the absorption of one or more biologically active molecules. Such methods include contacting cells with the intercellular junction disruption agents provided prior to, concurrently with or after the administration of the one or more biologically active molecules. The biologically active molecules can be administered in the same way as the intercellular junction disruption agents, or they can be administered differently.

The methods provided include methods for enhancing the delivery of one or more biologically active molecules to target tissues by transiently disrupting the intercellular seals formed by the tight junctions. As used herein "enhanced" means to increase the delivery of the biologically active molecule to a particular cell or tissue or to systemic circulation generally. The term also refers to the increased passage of a biologically active molecule via paracellular transport. In some embodiments the enhanced delivery refers to the passage of a biologically active molecule that otherwise would not be able to traverse the intercellular junctions. In other embodiments the delivery is enhanced 5%, 10%, 15%, 20%, 25%, 30%, 40%, 50%, 60%, 70%, 80%, 90%, 100%, 200%, 300%, 500%, 1000% or more more than the delivery that would be accomplished without the use of an intercellular junction disruption agent as provided herein. It has been found, for example, that inhalational administration of effective amounts of unfractionated sodium heparin powder in mice resulted in the absorption of the polymer into the lungs and trachea in mice. In vitro it has been observed that the addition of the polymer causes the disruption of tight junctions in different types of epithelial cells, which is associated with shedding of syndecans. Thus a biologically active molecule, such as a drug, that is administered along with an intercellular junction disruption agent, such as heparin, can be effectively delivered to target tissues or tumors. In some embodiments the biologically active agent is attached to the intercellular junction disruption agent. Furthermore, the intercellular junction disruption agents can be modulators of syndecan shedding and be used to modify tight junctions and impinge on paracellular transport through this mechanism. In some embodiments the use of ardeparin sodium powder for enhancing transepithelial drug delivery by affecting the barrier function between the epithelial cells is provided. In other embodiments glycosaminoglycan-degrading enzymes are used to disrupt the tight junctions and/or to modulate drug delivery across the cellular barrier. These enzymes include hep-I, hep-III and C-ABC.

As used herein a "biologically active molecule/agent" is any molecule/agent that has some biological effect. Biologically active molecules include polar or charged molecules, such as anionic polysaccharides like heparin. In some embodiments the biologically active molecule is different from the intercellular junction disruption agent. The biologically active agent can be administered prior to, concurrently with or after the intercellular junction disruption agent is administered. Preferably, the biologically active agent and intercellular junction disruption agent are administered so that the delivery of the biologically active agent is enhanced because of the disruption of the intercellular junctions. In some embodiments the intercellular junction disruption agent is administered 1, 2, 3, 4, 5, 10, 15, 20, 25, 30, 60 or more minutes prior to the administration of the biologically active agent. In other embodiments the intercellular junction disruption agent is administered 1, 2, 3, 4, 5, 6, 7, 8, 9, 10, 15, 20 or more hours prior to the administration of the biologically active agent. In still other embodiments the intercellular junction disruption agent is administered at least 10 minutes prior to the administration of the biologically active agent. In still other embodiments the intercellular junction disruption agent is administered no more than 1, 2, 3, 4, 5, 6, 7, 8, 9, or 10 hours before the administration of the biologically active agent. In still other embodiments the intercellular junction disruption agent is administered anywhere from 1 minute to 10 hours prior to the administration of the biologically active agent.

In some embodiments the biologically active agent is administered 1, 2, 3, 4, 5, 10, 15, 20, 25, 30, 60 or more minutes prior to the administration of the intercellular junction disruption agent. In other embodiments the biologically active agent is administered 1, 2, 3, 4, 5, 6, 7, 8, 9, 10, 15, 20, 30, 40, 50, 60, 75, 100 or more hours prior to the administration of the intercellular junction disruption agent. In still other embodiments the biologically active agent is administered at least 10 minutes prior to the administration of the intercellular junction disruption agent. In yet other embodiments the biologically active agent is administered 1, 2, 3, 4, 5, 10, 20, 30 or more days prior to the administration of the intercellular junction disruption agent. In further embodiments the biologically active agent is administered 1, 2, 3, 4, 5, 10, 20, 30 or more months prior to the administration of the intercellular junction disruption agent. In yet other embodiments the biologically active agent is administered 1, 2, 3, 4, 5 or more years prior to the administration of the intercellular junction disruption agent. In some embodiments, therefore, administration can be accomplished with the use of slow release materials, such as polyanhydride wafers or block copolymers, such as poly(ethylene glycol) (PEG)/poly(lactic-co-glycolic acid) (PLGA) block copolymers as an example. In still other embodiments the biologically active agent is administered no more than 1, 2, 3, 4, 5, 6, 7, 8, 9, 10, 15, 24, 36 or 72 hours before the administration of the intercellular junction disruption agent.

The biologically active agents and intercellular junction disruption agents can be administered in different ways. For example, for enhanced delivery across the blood-brain barrier the intercellular junction disruption agent can be administered via the internal carotid artery while the biologically active agent is administered intravenously, subcutaneously, etc. In another example, the intercellular junction disruption agent, attached to a targeting molecule, can be administered such that it enters systemic circulation (e.g., via a pulmonary, sublingual, gastrointestinal or topical route), and the biologically active agent can be administered intravenously. The biologically active agent in another embodiment of this example can be administered with an intercellular junction disruption agent that is the same as or different from the intercellular junction disruption agent linked to the targeting molecule. In such an embodiment the intercellular junction disruption agent linked to a targeting molecule would allow for the disruption of intercellular junctions at the targeted site, while the intercellular junction disruption agent administered with the biologically active agent could allow for its enhanced delivery via any of the administration routes provided herein.

In one embodiment the intercellular junction disruption agent can be linked to a molecule that targets the blood-brain barrier (e.g., an antibody to transferrin receptor, such as OX 26, or an antibody to PGP1). In another embodiment the biologically active agent can be administered prior to the intercellular junction disruption agent via a slow release device, and the intercellular junction disruption agent can then be administered via any mode provided. The intercellular junction disruption agent can be linked to a targeting molecule in one embodiment. In another embodiment it is the biologically active agent that is linked to a targeting molecule.

In other embodiments the biologically active agent is the same as the intercellular junction disruption agent but is used in a different amount or is administered at a different time, etc.

Biologically active agents include proteins, chemical compounds, nucleic acids, polysaccharides (which includes monosaccharides, disaccharides, or oligosaccharides), small molecules and peptide therapeutics. Nucleic acids include DNA, RNA, antisense oligonucleotides, interfering RNA (RNAi), small interfering RNA (siRNA), etc. The nucleic acids can be single-, double-, triple-stranded, etc. Biologically active agents also include the other therapeutic agents/drugs described herein. In one aspect of the invention compositions are provided which comprise the intercellular junction disruption agents and the biologically active agents provided herein.

The intercellular junction disruption agent preferably serves as the mechanism to help deliver the biologically active agent or agents. In some embodiments, the biologically active molecule is different from the intercellular junction disruption agents. In other embodiments the biologically active molecule is not a polysaccharide. In some of these embodiments the biologically active molecule is not heparin.

The compositions and methods provided herein can be used, depending on the intercellular junction disruption agent, to treat or prevent a number of disorders. For instance, in some embodiments the compositions and methods provided are useful for preventing and/or treating coagulation, angiogenesis, thrombotic disorders, cardiovascular disease, vascular conditions, cerebrovascular conditions, stroke, atherosclerosis, neurodegenerative disease, respiratory disorders, asthma, inflammatory disorders, immunologic disorders, lupus, allergic disorders, circulatory shock and related disorders, central nervous system disorders, Alzheimer's disease, dermatological disorders, psoriasis, inflammatory bowel disease, Crohn's disease, ulcerative colitis, fibrotic lungs, infection or an infection related disorder, *pseudomonas* infection, *S. aureus* infection, or inhibiting cancer cell growth and metastasis.

The compositions and treatments provided can also be used to prevent and/or treat disorders which include diabetes, encephalitis, hydrocephalus, obesity, varicose veins, vasculititides, lymphangitis, lymphedema, hypertension, superior vena caval syndrome, myocarditis, restrictive cardiomyopathy, pericarditis, hereditary hemopoetic disorders, disseminated intravascular coagulation, restrictive lung diseases, obstructive lung disease, cystic fibrosis, gastrointestinal ulcerations, Wilson's disease, alpha1-antitrypsin disease, cholecystsitis, gall stones, kidney stones, renal and bladder infections/urinary tract infections or protein deficiencies (e.g. Tay Sachs). The compositions and methods provided can also be used to promote neural regeneration and/or spinal cord repair.

Each of these disorders is well-known in the art and/or is described, for instance, in *Harrison's Principles of Internal Medicine* (McGraw Hill, Inc., New York), which is incorporated by reference.

Compositions and methods for increasing the permeability of a cell barrier are also provided. The methods include contacting the cell barrier with the compositions provided herein in an amount effective to increase the permeability of the cell barrier. The cell barrier can be an epithelial cell barrier or an endothelial cell barrier. Non-limiting examples of particular cell barriers in the body include barriers formed by pericytes, pneumocytes, muscle cells (e.g., smooth muscle cells), and glial cells (e.g., astrocytes). Further examples are provided directly below. The results presented herein show that heparin sodium powder, ardeparin sodium powder, heparinase I, heparinase III and chondroitinase ABC can be effectively used as modulators of transepithelial permeability and thus can play a role in drug delivery to target tissues. There are several target tissues, to which drug delivery is otherwise complicated, that can be benefited from this system of drug delivery that modulates the epithelial barrier function. Some examples of these tissues are provided.

The compositions and methods provided can be used to increase the permeability of the blood-brain barrier (BBB) and, therefore, can be used to enhance the delivery of biologically active molecules through the BBB. The BBB separates the molecular, cellular and ionic environment of the blood from the brain, and the intercellular tight junctional complex present in the BBB achieves this barrier function. To deliver membrane impermeant drugs to the brain the need to circumvent this barrier by the reversible opening of the tight junctions arises. A drug that is combined with the compositions provided could easily traverse the BBB by the transient opening of the tight junctions in the BBB. The compositions and methods thus have a huge potential in the field of drug delivery to the brain and to the central nervous system. Such compositions and methods are provided.

The compositions and methods provided can also be used to increase the permeability and thereby enhance the delivery of biologically active molecules across the nasal tract membrane. Such compositions and methods interestingly can also be used to enhance central nervous system drug delivery. A recent development in the delivery of biologically active molecules to the brain has been the possibility of direct absorption into the brain following administration through a nasal route, avoiding the blood-brain barrier altogether. However, the nasal tract is lined with epithelial cells with tight junctions, which act as a barrier to the absorption of any polar or large molecule. Accordingly, the compositions and methods provided can be used to circumvent this barrier and enhance delivery to the central nervous system (e.g., the brain) via nasal administration.

In addition, provided herein are compositions and methods for ocular administration. Enhanced delivery to the central nervous system (e.g., the brain) can be accomplished via ocular administration, and therefore, compositions and methods for accomplishing this are provided.

The mucosal epithelium overlying the airway smooth muscle also poses a formidable barrier to macromolecule drug delivery. The mucosal epithelium in the upper airway functions as a critical barrier to protect the internal environment from pathogens and toxins in the external environment. The apical surface, which prevents transcellular passage of macromolecules, and tight junctions, which define the junction between the apical and basolateral surfaces, prevent paracellular leakage of macromolecules and apical-to-basal delivery of therapeutic macromolecules. The compositions and methods provided thus also have applications to the upper respiratory tract or airway. Provided herein are compositions and methods for enhancing the delivery of one or more biologically active molecules through the upper respiratory tract in a subject. The method includes contacting the upper respiratory tract with the compositions described herein and one or more biologically active molecules. The compositions and methods can be used for asthma therapy and for treatment of other upper airway disorders by modulating the barrier function of the mucosal epithelium.

Pulmonary delivery of drugs is gaining increasing importance because of its enormous advantages over other delivery techniques. Several drugs cannot be orally administered in effective doses because enzymes in the gastrointestinal tract and the acidic environment in the stomach degrade them. These drugs could be directly injected into the bloodstream but the necessity of injections causes a great deal of inconvenience and discomfort to the patients. Thus there is a need for other methods of delivery similar to nasal administration. A substance that can enhance the absorption of the drug in the lower respiratory tract (lungs, trachea, larynx, bronchial tree, etc.) so that it can be directly absorbed by the blood would thus have a great potential in the field of drug delivery. Pulmonary delivery of heparin powder has been shown to cause effective amounts of the sugar to be absorbed into the lungs and trachea. Compositions and methods for enhancing the delivery of one or more biologically active molecules through the lower respiratory tract in a subject are also provided. These methods allow for a painless delivery of effective amounts of drug to the lower respiratory tract and hence to the blood.

The compositions and methods provided also pertain to the enhanced delivery of biologically active molecules via the skin, sublingual membranes or gastrointestinal tract. In some embodiments the method of delivery enhances the delivery of a biologically active agent to the systemic circulation. The skin has long been looked on favorably as a route of systemic drug administration because it has a number of advantages over more conventional routes of delivery. Transdermal delivery of drugs can be achieved by modulating the epithelial barrier function of the skin. Thus, epithelial permeability modulators like the intercellular junction disruption agents provided can effectively be used for transdermal delivery of drugs. Therefore, the compositions and methods provided can be used for the treatment of chronic wounds and subdermal infections. The compositions and methods are also used via the gastrointestinal route as oral delivery has long been an easy was to administer drugs to subjects. The methods and compositions provided enhance the ability to delivery biologically active molecules via the gastrointestinal tract. This includes in some embodiments allowing for the delivery of otherwise impermeant drugs.

Sublingual, meaning 'under the tongue' refers to a method of administering substances via the mouth in such a way that the substances are rapidly absorbed via the blood vessels under the tongue rather than via the digestive tract. The route of absorption via the highly vascularised buccal mucosa allows the substances a more direct access to the blood circulation, thus providing direct systemic administration. Medically, sublingual drug administration is used in the field of cardiovascular drugs, steroids, some barbiturates and enzymes. It has been a developing field in the administration of many vitamins and minerals, which are found to be readily and thoroughly absorbed by this method (Squier C A et al., 1975). There is considerable evidence that most sublingual substances are absorbed by simple diffusion. However, not all substances are permeable and accessible to the buccal mucosa. Drugs that are not permeable through the buccal mucosa can be administered sublingually with the methods provided as drug absorption can be achieved by modulating the permeability of the buccal epithelium. Also provided are methods and compositions that enhance the delivery of drugs that are permeable through the buccal mucosa. These methods and compositions allow for the more rapid and/or efficacious delivery of such drugs. In some embodiments, a lower amount of the drug is required.

The compositions and methods provided have not only uses in vitro but also in vivo, such as for a number of therapeutic purposes. The compositions of the invention can be used for the treatment of any condition in which one or more intercellular junction disruption agents allow for the enhanced delivery of one or more biologically active molecules that have been identified as a therapeutic for the condition. In some embodiments the intercellular junction disruption agent is in an effective amount to disrupt the intercellular junction, and this amount is not a therapeutically effective amount for the particular condition. In other embodiments the intercellular junction disruption agent is in an effective amount to disrupt the intercellular junction, and this amount is a therapeutically effective amount to treat the condition. In some of these embodiments the therapeutic effect of the intercellular junction disruption agent is less than the therapeutic effect of the one or more biologically active agents. Whether or not the intercellular junction disruption agent will have a therapeutic effect in addition to the intercellular junction disruption effect will depend on the particular condition treated as well as the particular intercellular junction disruption agent. The therapeutic effect can be less than one or some combination of the biologically active agents that are administered to treat the condition.

In some embodiments, the compositions of intercellular junction disruption agents can be administered to a subject "not ordinarily in need of treatment thereof". A subject not ordinarily in need of treatment thereof refers to a subject who suffers from a condition where the intercellular junction disruption agent is not normally administered to treat the condition. Conditions which are not ordinarily treated with intercellular junction disruption agents can include in some embodiments nonangiogenic, noncoagulation, nonthrombotic, nonrespiratory, noninflammatory, nonimmunologic, nonallergic and/or nonvascular disorders. In some embodiments, depending on the particular intercellular junction disruption agent, the condition is not a neurodegenerative disease and/or not a central nervous system disorder. In some embodiments the condition is not spinal cord injury. In other embodiments the subject is not in need of neural regeneration. In some embodiments the condition is not Alzheimers. In some embodiments the condition is a central nervous system disorder that is not Alzheimers. In other embodiments the condition is not a dermatological disorder. In other embodiments the condition is not psoriasis. In some embodiments the condition is a dermatological disorder that is not psoriasis. In some embodiments the subject does not have a circulatory shock or related disorder, cardiovascular disease, atherosclerosis, cancer, stroke and/or Alzheimers. In some embodiments the subject has a condition that is not inflammatory bowel disease (e.g., Crohn's, ulcerative colitis). In some embodiments the condition is not a respiratory disorder. In other embodiments the subject does not have asthma, fibrotic lungs and/or an infection or an infection related disorder. In still other embodiments the subject has a condition that is a respiratory disorder that is not asthma. In some embodiments the subject does not have a *pseudomonas* infection or a *S. aureus* infection. In other embodiments the subject has an infection that is not a *pseudomonas* infection or a *S. aureus* infection. In some embodiments the condition is not an inflammatory disorder. In some embodiments the condition is not an immunologic disorder. In other embodiments the condition is not lupus. In some embodiments the condition is an immunologic disorder that is not lupus. In other embodiments the subject is not undergoing a tissue or organ transplant or a surgical procedure where the use of the intercellular junction disruption agent would be normally desired.

As stated above the compositions and methods provided herein can be used, depending on the intercellular junction disruption agent, to treat and/or prevent a number of disorders.

In some embodiments, the compositions are useful for treating or preventing disorders associated with coagulation. A "disease associated with coagulation" as used herein refers to a condition characterized by local inflammation resulting from an interruption in the blood supply to a tissue due to a blockage of the blood vessel responsible for supplying blood to the tissue such as is seen for myocardial or cerebral infarction. Coagulation disorders include, but are not limited to, cardiovascular disease and vascular conditions such as cerebral ischemia. The compositions and methods of the invention are also useful for treating cardiovascular disease. Cardiovascular diseases include, but are not limited to, acute myocardial infarction, unstable angina, and atrial fibrillation.

The compositions and methods provided thus can also include anti-inflammatory agents, anti-thrombotic agents, anti-platelet agents, fibrinolytic agents, lipid reducing agents, direct thrombin inhibitors, and glycoprotein IIb/IIIa receptor inhibitors.

Anti-inflammatory agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam;

Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium.

Lipid reducing agents include gemfibrozil, cholystyramine, colestipol, nicotinic acid, probucol lovastatin, fluvastatin, simvastatin, atorvastatin, pravastatin, cirivastatin.

Glycoprotein IIb/IIIa receptor inhibitors are both antibodies and non-antibodies, and include but are not limited to ReoPro (abcixamab), lamifiban, tirofiban.

Anti-thrombotic agents and anti-platelet agents are described in more detail below.

The compositions provided are also useful for treating vascular conditions. Vascular conditions include, but are not limited to, disorders such as deep venous thrombosis, cerebral ischemia, including stroke, and pulmonary embolism. Because it is often difficult to discern whether a stroke is caused by a thrombosis or an embolism, the term "thromboembolism" is used to cover strokes caused by either of these mechanisms. The compositions can also be very valuable in the treatment of venous thromboembolism. The methods of the invention in some embodiments are directed to the treatment of acute thromboembolic stroke. An acute stroke is a medical syndrome involving neurological injury resulting from an ischemic event, which is an interruption in the blood supply to the brain.

Compositions and methods, therefore, are also provided to treat a cerebrovascular condition. Cerebrovascular conditions include, for example, stroke, cerebral arteriosclerosis, cerebral aneurysm, intracranial hemorrhage (subarachnoid hemorrhage, berry aneurysms etc.), lacunar infarcts, slit hemorrhages (hypertension related), hypertensive encephalopathy, cerebral autosomal dominant arteriopathy with subcortical infarcts and leukoencephalopathy (CADASIL), and cerebral artery disease. The compositions and methods provided can also be used to treat brain injury and/or enhance brain function such as enhancing cerebral/behavioral function.

An effective amount of the compositions provided for the treatment of stroke is that amount sufficient to reduce in vivo brain injury resulting from the stroke. A reduction of brain injury is any prevention of injury to the brain which otherwise would have occurred in a subject experiencing a thromboembolic stroke absent the treatment of the invention. Several physiological parameters may be used to assess reduction of brain injury, including smaller infarct size, improved regional cerebral blood flow, and decreased intracranial pressure, for example, as compared to pretreatment patient parameters, untreated stroke patients or stroke patients treated with thrombolytic agents alone.

The compositions provided may be used for treating a disease associated with coagulation. Examples of therapeutics useful in the treatment of diseases associated with coagulation include anticoagulation agents, antiplatelet agents, and thrombolytic agents.

Anticoagulation agents prevent the coagulation of blood components and thus prevent clot formation. Anticoagulants include, but are not limited to, warfarin, coumadin, dicumarol, phenprocoumon, acenocoumarol, ethyl biscoumacetate, and indandione derivatives.

Antiplatelet agents inhibit platelet aggregation and are often used to prevent thromboembolic stroke in patients who have experienced a transient ischemic attack or stroke. Antiplatelet agents include, but are not limited to, aspirin, thienopyridine derivatives such as ticlopodine and clopidogrel, dipyridamole and sulfinpyrazone, as well as RGD mimetics and also antithrombin agents such as, but not limited to, hirudin.

Thrombolytic agents lyse clots which cause the thromboembolic stroke. Thrombolytic agents have been used in the treatment of acute venous thromboembolism and pulmonary emboli and are well known in the art (e.g. see Hennekens et al, *J Am Coll Cardiol*; v. 25 (7 supp), p. 18S-22S (1995); Holmes, et al, *J Am Coll Cardiol*; v. 25 (7 suppl), p. 10S-17S(1995)). Thrombolytic agents include, but are not limited to, plasminogen, $a_2$-antiplasmin, streptokinase, antistreplase, tissue plasminogen activator (tPA), and urokinase. "tPA" as used herein includes native tPA and recombinant tPA, as well as modified forms of tPA that retain the enzymatic or fibrinolytic activities of native tPA. The enzymatic activity of tPA can be measured by assessing the ability of the molecule to convert plasminogen to plasmin. The fibrinolytic activity of tPA may be determined by any in vitro clot lysis activity known in the art, such as the purified clot lysis assay described by Carlson, et. al., *Anal. Biochem.* 168, 428-435 (1988) and its modified form described by Bennett, W. F. Et al., 1991, Supra, the entire contents of which are hereby incorporated by reference.

Pulmonary embolism as used herein refers to a disorder associated with the entrapment of a blood clot in the lumen of a pulmonary artery, causing severe respiratory dysfunction. Pulmonary emboli often originate in the veins of the lower extremities where clots form in the deep leg veins and then travel to lungs via the venous circulation. Thus, pulmonary embolism often arises as a complication of deep venous thrombosis in the lower extremity veins. Symptoms of pulmonary embolism include acute onset of shortness of breath, chest pain (worse with breathing), and rapid heart rate and respiratory rate. Some individuals may experience haemoptysis.

The products and methods of the invention are also useful for treating or preventing atherosclerosis. Atherosclerosis is one form of arteriosclerosis that is believed to be the cause of most coronary artery disease, aortic aneurysm and atrial disease of the lower extremities, as well as contributing to cerebrovascular disease.

The compositions provided are also valuable in treatment of respiratory diseases such as asthma, allergic disorder, emphysema, adult respiratory distress syndrome (ARDS), lung reperfusion injury, ischemia-reperfusion injury of the lung, kidney, heart, and gut, and lung tumor growth and metastasis. Asthma is a disorder of the respiratory system characterized by inflammation, narrowing of the airways and increased reactivity of the airways to inhaled agents. Asthma is frequently, although not exclusively, associated with atopic or allergic symptoms. Asthma may also include exercise induced asthma, bronchoconstrictive response to bronchostimulants, delayed-type hypersensitivity, auto immune encephalomyelitis and related disorders. Allergies are generally caused by IgE antibody generation against allergens. Emphysema is a distention of the air spaces distal to the terminal bronchiole with destruction of alveolar septa. Emphysema arises out of elastase induced lung injury. Adult respiratory distress syndrome is a term which encompasses many acute defuse infiltrative lung lesions of diverse ideologies which are accompanied by severe atrial hypoxemia. One of the most frequent causes of ARDS is sepsis. Other types of inflammatory diseases which are treatable with the compositions provided are refractory ulcerative colitis, non-specific ulcerative colitis and interstitial cystitis.

The compositions and methods provided are also useful for treating lung disease, such as chronic obstructive pulmonary disease/disorder (COPD), fibrosis, restrictive lung disease, mesothelioma, pneumonia, sarcoidosis and cystic fibrosis.

The compositions can also be used for inhibiting angiogenesis. Angiogenesis as used herein is the inappropriate formation of new blood vessels. "Angiogenesis" often occurs in tumors when endothelial cells secrete a group of growth factors that are mitogenic for endothelium causing the elongation and proliferation of endothelial cells which results in a generation of new blood vessels. The inhibition of angiogenesis can cause tumor regression in animal models, suggesting a use as a therapeutic anticancer agent. An effective amount for inhibiting angiogenesis is an amount which is sufficient to diminish the number of blood vessels growing into a tumor. This amount can be assessed in an animal model of tumors and angiogenesis, many of which are known in the art. Angiogenic disorders include, but are not limited to, neovascular disorders of the eye, osteoporosis, psoriasis, and arthritis.

The compositions are also useful for inhibiting neovascularization associated with eye disease. In another embodiment, the composition is administered to treat psoriasis. Psoriasis is a common dermatologic disease associated with chronic inflammation.

The compositions and methods provided are also useful for treating dermatological disorders. In some embodiments the dermatological disorder is not psoriasis. Dermatological disorders include vitiligo, melanoma, dysplasic nevi, seborrheic keratoses, acanthosis nigricans, adnexal tumors, other epidermal tumors (actinic keratosis, squamous cell carcinoma, basal cell carcinoma, merkel cell carcinoma, histiocytosis X, mycosis fungoides/cutaneous T-cell lymphoma), mastocytosis, eczema/acute eczematous dermatitis, urticaria, erythema multiforme, psoriasis, lichen planus, lupus/systemic lupus erythematosus, bullous diseases, acne vulgaris, and panniculitis.

The compositions may also inhibit cancer cell growth and metastasis. Thus the methods of the invention are useful for treating tumor cell proliferation or metastasis in a subject. The terms "treat" and "treating" as used herein refer to inhibiting completely or partially the biological effect, e.g., angiogenesis or proliferation or metastasis of a cancer or tumor cell, as well as inhibiting any increase in the biological effect, e.g., angiogenesis or proliferation or metastasis of a cancer or tumor cell.

The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreatic cancer; prostate cancer; rectal cancer; sarcomas; skin cancer; testicular cancer; thyroid cancer; and renal cancer, as well as other carcinomas and sarcomas.

A subject in need of treatment may be a subject who has a high probability of developing cancer. These subjects include, for instance, subjects having a genetic abnormality, the presence of which has been demonstrated to have a correlative relation to a higher likelihood of developing a cancer and subjects exposed to cancer-causing agents such as tobacco, asbestos, or other chemical toxins, or a subject who has previously been treated for cancer and is in apparent remission.

Anti-cancer drugs that can serve as biologically active molecules are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Anti-cancer agents can also include cytotoxic agents and agents that act on tumor neovasculature. Cytotoxic agents include cytotoxic radionuclides, chemical toxins and protein toxins. The cytotoxic radionuclide or radiotherapeutic isotope preferably is an alpha-emitting isotope such as $^{225}$Ac, $^{211}$At, $^{212}$Bi, $^{213}$Bi, $^{212}$Pb, $^{224}$Ra or $^{223}$Ra. Alternatively, the cytotoxic radionuclide may a beta-emitting isotope such as $^{186}$Rh, $^{188}$Rh, $^{177}$Lu, $^{90}$Y, $^{131}$I, $^{67}$Cu, $^{64}$Cu, $^{153}$Sm or $^{166}$Ho. Further, the cytotoxic radionuclide may emit Auger and low energy electrons and include the isotopes $^{125}$I, $^{123}$I or $^{77}$Br.

Suitable chemical toxins or chemotherapeutic agents include members of the enediyne family of molecules, such as calicheamicin and esperamicin. Chemical toxins can also be taken from the group consisting of methotrexate, doxorubicin, melphalan, chlorambucil, ARA-C, vindesine, mitomycin C, cis-platinum, etoposide, bleomycin and 5-fluorouracil. Toxins also include poisonous lectins, plant toxins such as ricin, abrin, modeccin, botulina and diphtheria toxins. Of course, combinations of the various toxins are also provided thereby accommodating variable cytotoxicity. Other chemotherapeutic agents are known to those skilled in the art.

Agents that act on the tumor vasculature can include tubulin-binding agents such as combrestatin A4 (Griggs et al., *Lancet Oncol.* 2:82, 2001), angiostatin and endostatin (reviewed in Rosen, *Oncologist* 5:20, 2000, incorporated by reference herein), interferon inducible protein 10 (U.S. Pat. No. 5,994,292), and the like. Anticancer agents also include immunomodulators such as α-interferon, γ-interferon, and tumor necrosis factor alpha (TNFα).

The invention also contemplates compositions and methods for the treatment of subjects having or at risk of developing neurodegenerative disease or suffering an injury to nerve cells. Neuronal cells are predominantly categorized based on their local/regional synaptic connections (e.g., local circuit interneurons vs. longrange projection neurons) and receptor sets, and associated second messenger systems. Neuronal cells include both central nervous system (CNS) neurons and peripheral nervous system (PNS) neurons. There are many different neuronal cell types. Examples include, but are not limited to, sensory and sympathetic neurons, cholinergic neurons, dorsal root ganglion neurons, proprioceptive neurons (in the trigeminal mesencephalic nucleus), ciliary ganglion neurons (in the parasympathetic nervous system), c-fibers (pain fibers) etc. A person of ordinary skill in the art will be able to easily identify neuronal cells and distinguish them from non-neuronal cells such as glial cells, typically utilizing cell-morphological characteristics, expression of cell-specific markers, secretion of certain molecules, etc.

"Neurodegenerative disease/disorder" is defined herein as a disorder in which progressive loss of neurons occurs either in the peripheral nervous system or in the central nervous system. As used herein "central nervous system disorders" is intended to include neurodegenerative diseases/disorders, injuries to the central nervous system (e.g., spinal cord injury), etc. Examples of neurodegenerative disorders include: (i) chronic neurodegenerative diseases such as familial and sporadic amyotrophic lateral sclerosis (FALS and ALS, respectively), familial and sporadic Parkinson's disease, Huntington's disease, familial and sporadic Alzheimer's disease, multiple sclerosis, olivopontocerebellar atrophy, multiple system atrophy, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, vertigo as result of CNS degeneration; pathologies arising with chronic alcohol or drug abuse including, for example, the degeneration of neurons in locus coeruleus and cerebellum; pathologies arising with aging including degeneration of cerebellar neurons and cortical neurons leading to cognitive and motor impairments; and pathologies arising with chronic amphetamine abuse including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor). and Wernicke-Korsakoff's related dementia. Neurodegenerative diseases affecting sensory neurons include Friedreich's ataxia, diabetes, peripheral neuropathy, and retinal neuronal degeneration. Neurodegenerative diseases of limbic and cortical systems include cerebral amyloidosis, Pick's atrophy, and Retts syndrome. The foregoing examples are not meant to be comprehensive but serve merely as an illustration of the term "neurodegenerative disorder."

The compositions provided, therefore, can include biologically active molecules for the promotion of nerve regeneration and/or treatment of neurodegenerative disease.

The biologically active molecules, therefore, can be antiparkinsonian agents, which include, for example, Benztropine Mesylate; Biperiden; Biperiden Hydrochloride; Biperiden Lactate; Carmantadine; Ciladopa Hydrochloride; Dopamantine; Ethopropazine Hydrochloride; Lazabemide; Levodopa; Lometraline Hydrochloride; Mofegiline Hydrochloride; Naxagolide Hydrochloride; Pareptide Sulfate; Procyclidine Hydrochloride; Quinelorane Hydrochloride; Ropinirole Hydrochloride; Selegiline Hydrochloride; Tolcapone; Trihexyphenidyl Hydrochloride. Drugs for the treatment of amyotrophic lateral sclerosis include but are not limited to Riluzole. Drugs for the treatment of Paget's disease include but are not limited to Tiludronate Disodium.

Biologically active molecules can also be agents that promote neuronal regeneration. Neuronal regenerative agents include growth factors and neurotrophic agents that promote neuronal growth and/or survival. Such examples include, but are not limited to, nerve growth factor (NGF), brain-derived neurotrophic factor (BDNF), cardiotrophin-1 (CT-1), choline acetyltransferase development factor (CDF), ciliary neurotrophic factor (CNTF) fibroblast growth factor-1 (FGF-1), FGF-2, FGF-5, glial cell-line-derived neurotrophic factor (GDNF), insulin, insulin-like growth factor-1 (IGF-1), IGF-2, interleukin-6 (IL-6), leukemia inhibitor factor (LIF), neurite promoting factor (NPF), neurotrophin-3 (NT-3), NT-4, platelet-derived growth factor (PDGF), protease nexin-1 (PN-1), S-100, transforming growth factor.beta. (TGF-.beta.), decorin, anti-TGF-beta antibodies, mutated TGF-beta, and vasoactive intestinal peptide (VIP) (Oppenheim, 1996, Neuron 17:195-197).

The compositions and methods provided can also be used to treat a subject with a central nervous system disorder. Central nervous system disorders include, for example, Alzheimers, Parkinson's disease, Huntington's disease, cerebrovascular disease, epilepsy, depression, mania, schizophrenia and psychotic disorders.

The compositions provided, therefore, can include agents for treating and/or preventing central nervous system disorders. Such agents include the following examples.

Benzodiazepines (e.g., Alprazolam, Chlordiazepoxide, Clorazepate, Clonazepam, Diazepam, Estazolam, Flurazepam, Halazepam, Lorazepam, Midazolam, Oxazepam, Prazepam, Quazepam, Temazepam, Triazolam); Benzodiazepine Antagonist (e.g., Flumazenil); Barbiturates (e.g., Amobarbital, Aprobarbital, Butabarbital sodium, Mephobarbital, Pentobarbital, Phenobarbital, Secobarbital); Buspirone; Chloral Hydrate; Ethchlorvynol; Ethinamate; Hydroxyzine; Meprobamate; Paraldehyde; Zaleplon; Zolpidem; Treatments of acute alcohol withdrawal syndrome (e.g., Clorazepate, Diazepam, Oxazepam, Thiamine); Treatments for the prevention of alcohol abuse (e.g., Disulfiram, Naltrexone); Treatments of acute methanol or ethylene glycol poisoning (e.g., Ethanol, Fomepizole); Anti-Epileptic Drugs (e.g., Carbamazepine, Clonazepam, Clorazepate Dipotassium, Diazepam, Ethusuximide, Ethotoin, Felbamate, Fosphenytoin, Gabapentin, Lamotrigine, Levetiracetam, Lorazepam, Mephenytoin, Mephobarbital, Methsuximide, Oxycarbapazepine, Paramethadione, Pentobarbital, Phensuximide, Phenytoin, Primidone, Tiagabine, Topiramate, Trimethadione, Valproic Acid); General Anesthetics (e.g., Desflurane, Demadetomidine, Diazepam, Enflurane, Etomidate, Halothane, Isoflurane, Ketamine, Lorazepam, Mthohexital, Mrthoxyflurane, Midazolam, Nitrous Oxide, Propofol, Sevoflurane, Thiamylal, Thiopental); Local Anesthetics (e.g., Benzocaine, Bupivacaine, Butamben Pictate, Choloprocaine, Cocaine, Dibucaine, Dyclonine, Etidocaine, Levobupivacaine, Lidocaine, Mepivacaine, Pramoxine, Prilocaine, Procaine, Proparacaine, Propoxicaine, Ropivacaine, Tetracaine); Skeletal Muscle Relaxants (e.g., Neuromascular Blocking Agents: Atracurium, Cisatracurium, Doxacurium, Metocurine, Mivacurium, Pancuronium, Pipecuronium, Rapacuronium, Rocurinium, Succunylcholine, Tubocurarine, Vecuronium); Spasmolytics (e.g., Baclofen, Botulinum Toxin Type A, Carisoprodol, Chlorphenesin, Chlorzoxazone, Cyclobenzaprine, Diazepam, Gabapentin, Metaxalone, Methocarbamol, Orphenadrine, Riluzole, Tizanidine); Anti-Parkinsonism Agents (also movement disorder agents) (e.g., Amantadine, Benztropine, Biperiden, Bromocriptine, Carbidopa, Entacapone, Levodopa, Orphenadrine, Penicillamine, Pergolide, Pramipexole, Procyclidine, Ropinirole, Selegiline, Tolcapone, Trientine, Trihexyphenidyl); Antipsychotic Agents (e.g., Acetophenazine, Chlorpromazine, Chlorprothixene, Clozapine, Fluphenazine (& esters), Haloperidol (& esters), Loxamine, Mesoridazine, Molindone, Olanzapine, Perphenazine, Pimozide, Prochlorperazine, Promazine, Quetiapine, Risperidone, Sertindole, Thioridazine, Thiothixene, Trifluoperazine, Triflupromazine, Ziprasidone); Mood Stabilizers (e.g., Carbamazepine, Divalproex, Lithium, Valproic Acid); Anti-Depressant Agents (e.g., Tricyclics: Amitriptyline, Clomipramine, Desipramine, Doxepin, Imipramine, Nortryptyline, Protryptyline, Trimipramine); Second & Third Generation Agents (e.g., Amoxapine, Bupropion, Maprotiline, Mirtazapine, Nefazodone, Trazodone, Venlafaxine); Selective Serotonin Reuptake Inhibitors (e.g., Citalopram, Flouxetine, Fluvoxamine, Paroxetine, Sertraline); Monoamine Oxidase Inhibitors (e.g., Phenelzine, Tranylcypromine); Opioid Analgesics & Antagonists; Opioid Analgesics (e.g., Alfentanil, Buprenorphine, Butorphanol, Codeine, Dezocine, Fentanyl, Hydromorphone, Levomethadyl Acetate, Levorphanol, Meperidine, Methadone, Morphine, Nalbuphine, Oxycodone, Oxymorphone, Pentazocine, Propoxyphene, Remifentanil, Sufentanil, Tramadol); Opioid Antagonists (e.g., Nalmefene, Naloxone, Naltrexone); and Antitussives (e.g., Codeine, Dextromethorphan).

The compositions provided herein can also be used for the treatment of rheumatoid arthritis, osteoarthritis or psoriasis. Treatment of osteoarthritis refers to any reduction of the subject's symptoms associated with osteoarthritis or controlling the progression of the disease. Generally treatment of osteoarthritis includes reducing pain and/or improving joint movement. Treatment of psoriasis includes the reduction of symptoms of the disease, such as reducing the shedding of skin, or controlling the progression of the disease. Treatment includes, therefore, methods for reducing inflammation associated with psoriasis. As used herein "controlling the progression of the disease" refers to any reduction in the rate of the progression of the disease. The term also includes halting disease progression.

The methods and compositions provided herein, therefore, in some embodiments include treatments used in osteoarthritis or psoriatic subjects. Other osteoarthritic treatments include NSAIDS and corticosteroids. Other psoriatic treatments include steroids, such as cortisone; scalp treatment with coal tar or cortisone (at times in combination with salicylic and lactic acid); anthralin; vitamin D (synthetic vitamin D analogue (calcipotriene)); retinoids (prescription vitamin A-related gels, creams (tazarotene), and oral medications (isotrentinoin, acitretin)); coal tar; Goeckerman Treatment (coal tar dressings and ultraviolet light); light therapy (Ultraviolet light B (UVB)); psoralen and UVA (PUVA); methotrexate; cyclosporine; alefacept; etancercept; infliximab; adalimumab; and efalizumab.

An "infection or infection related disorder" refers to any condition that results from the presence of one or more pathogenic microorganisms in the body of a subject. An infection or infection related disorder can be the result of a virus, bacteria, fungus, etc. Examples of viruses that have been found in humans include but are not limited to: *Retroviridae* (e.g. human immunodeficiency viruses, such as HIV-1 (also referred to as HDTV-III, LAVE or HTLV-III/LAV, or HIV-III; and other isolates, such as HIV-LP; *Picornaviridae* (e.g. polio viruses, hepatitis A virus; enteroviruses, human Coxsackie viruses, rhinoviruses, echoviruses); *Calciviridae* (e.g. strains that cause gastroenteritis); *Togaviridae* (e.g. equine encephalitis viruses, rubella viruses); *Flaviridae* (e.g. dengue viruses, encephalitis viruses, yellow fever viruses); *Coronoviridae* (e.g. coronaviruses); *Rhabdoviradae* (e.g. vesicular stomatitis viruses, rabies viruses); *Filoviridae* (e.g. ebola viruses); *Paramyxoviridae* (e.g. parainfluenza viruses, mumps virus, measles virus, respiratory syncytial virus); *Orthomyxoviridae* (e.g. influenza viruses); *Bungaviridae* (e.g. Hantaan viruses, bunga viruses, phleboviruses and Nairo viruses); *Arena viridae* (hemorrhagic fever viruses); *Reoviridae* (e.g. reoviruses, orbiviurses and rotaviruses); *Birnaviridae; Hepadnaviridae* (Hepatitis B virus); *Parvovirida* (parvoviruses); *Papovaviridae* (papilloma viruses, polyoma viruses); *Adenoviridae* (most adenoviruses); *Herpesviridae* (herpes simplex virus (HSV) 1 and 2, varicella zoster virus, cytomegalovirus (CMV), herpes virus; *Poxviridae* (variola viruses, vaccinia viruses, pox viruses); and *Iridoviridae* (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Gram positive bacteria include, but are not limited to, *Pasteurella* species, *Staphylococci* species, and *Streptococcus* species. Gram negative bacteria include, but are not limited to, *Escherichia coli, Pseudomonas* species, and *Salmonella* species. Specific examples of infectious bacteria include but are not limited to, *Helicobacter pyloris, Borelia burgdorferi, Legionella pneumophilia, Mycobacteria* sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A Streptococcus), *Streptococcus agalactiae* (Group B Streptococcus), *Streptococcus* (viridans group), *Streptococcus faecalis, Streptococcus bovis, Streptococcus*

(anaerobic sps.), *Streptococcus pneumoniae*, pathogenic *Campylobacter* sp., *Enterococcus* sp., *Haemophilus influenzae*, *Bacillus antracis*, *corynebacterium diphtheriae*, *corynebacterium* sp., *Erysipelothrix rhusiopathiae*, *Clostridium perfringers*, *Clostridium tetani*, *Enterobacter aerogenes*, *Klebsiella pneumoniae*, *Pasturella multocida*, *Bacteroides* sp., *Fusobacterium nucleatum*, *Streptobacillus moniliformis*, *Treponema pallidium*, *Treponema pertenue*, *Leptospira*, *Rickettsia*, and *Actinomyces israelli*.

Examples of fungi include *Cryptococcus neoformans*, *Histoplasma capsulatum*, *Coccidioides immitis*, *Blastomyces dermatitidis*, *Chlamydia trachomatis*, *Candida albicans*.

Other infectious organisms (i.e., protists) include *Plasmodium* spp. such as *Plasmodium falciparum*, *Plasmodium malariae*, *Plasmodium ovale*, and *Plasmodium vivax* and *Toxoplasma gondii*. Blood-borne and/or tissues parasites include *Plasmodium* spp., *Babesia microti*, *Babesia divergens*, *Leishmania tropica*, *Leishmania* spp., *Leishmania braziliensis*, *Leishmania donovani*, *Trypanosoma gambiense* and *Trypanosoma rhodesiense* (African sleeping sickness), *Trypanosoma cruzi* (Chagas' disease), and *Toxoplasma gondii*.

Other medically relevant microorganisms have been described extensively in the literature, e.g., see C. G. A Thomas, *Medical Microbiology*, Bailliere Tindall, Great Britain 1983.

Anti-bacterial agents useful in the invention include, but are not limited, to natural penicillins, semi-synthetic penicillins, clavulanic acid, cephalolsporins, bacitracin, ampicillin, carbenicillin, oxacillin, azlocillin, mezlocillin, piperacillin, methicillin, dicloxacillin, nafcillin, cephalothin, cephapirin, cephalexin, cefamandole, cefaclor, cefazolin, cefuroxine, cefoxitin, cefotaxime, cefsulodin, cefetamet, cefixime, ceftriaxone, cefoperazone, ceftazidine, moxalactam, carbapenems, imipenems, monobactems, euztreonam, vancomycin, polymyxin, amphotericin B, nystatin, imidazoles, clotrimazole, miconazole, ketoconazole, itraconazole, fluconazole, rifampins, ethambutol, tetracyclines, chloramphenicol, macrolides, aminoglycosides, streptomycin, kanamycin, tobramycin, amikacin, gentamicin, tetracycline, minocycline, doxycycline, chlortetracycline, erythromycin, roxithromycin, clarithromycin, oleandomycin, azithromycin, chloramphenicol, quinolones, co-trimoxazole, norfloxacin, ciprofloxacin, enoxacin, nalidixic acid, temafloxacin, sulfonamides, gantrisin, and trimethoprim; Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofingin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; and Zorbamycin.

Anti-viral agents include, but are not limited to, immunoglobulins, amantadine, interferon, nucleoside analogues, and protease inhibitors. Specific examples of anti-virals include, but are not limited to, Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Anti-fungal agents include, but are not limited to, imidazoles, FK 463, amphotericin B, BAY 38-9502, MK 991, pradimicin, UK 292, butenafine, chitinase, 501 cream, Acrisorcin; Ambruticin; Amorolfine, Amphotericin B; Azaconazole; Azaserine; Basifugin; Bifonazole; Biphenamine Hydrochloride; Bispyrithione Magsulfex; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole; Itraconazole; Kalafumgin; Ketoconazole; Lomofungin; Lydimycin; Mepartricin; Miconazole; Miconazole Nitrate; Monensin; Monensin Sodium; Naftifine Hydrochloride; Neomycin Undecylenate; Nifuratel; Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Proclonol; Pyrithione Zinc; Pyrrolnitrin; Rutamycin; Sanguinarium Chloride; Saperconazole; Scopafingin; Selenium Sulfide; Sinefingin; Sulconazole Nitrate; Terbinafine; Terconazole; Thiram; Ticlatone; Tioconazole; Tolciclate; Tolindate; Tolnaftate; Triacetin; Triafungin; Undecylenic Acid; Viridofulvin; Zinc Undecylenate; and Zinoconazole Hydrochloride.

An "allergic disorder" is any condition that is the result of the body's improper sensitivity to an allergen. The allergen can be a self or non-self antigen. The term is meant to include allergies and allergic reactions. Allergic disorders include but are not limited to eczema, allergic rhinitis or coryza, hay fever, conjunctivitis, bronchial asthma, urticaria (hives) and food allergies, and other atopic conditions. Agents used to treat allergic disorders are known in the art and include antihistamines as well as corticosteroids.

In another aspect of the invention the compositions and methods provided can further include agents or steps for inhibiting the opening of intercellular junctions, respectively. The inhibition of intercellular junction opening can be used in combination with the polysaccharides and polysaccharide-degrading enzymes as provided herein to further control the passage of materials through cell barriers. U.S. Pat. No. 6,686,341 provides nutritional components that contain negatively charged polysaccharides that exert an inhibitory effect on the opening of the tight junctions, thereby reducing the transport of high molecular weight substances, allergens and microorganisms. These polysaccharides include nondigestible polysaccharides, such as modified dextrans, modified galactomannans, glucomannans and arbinoxylans. In some embodiments, therefore, the intercellular junction disruption agent is not a nondigestible polysaccharide (i.e., a digestible polysaccharide) In other embodiments the intercellular junction disruption agent in not a dextran, galactomannan, glucomannan and/or arbinoxylan and/or a modified version thereof.

In another aspect of the invention screening methods are provided whereby the intercellular junction disruption agents provided can be used to screen for intercellular junction disruption inhibiting agents. In such methods the candidate intercellular junction disruption inhibiting agents are contacted with cells in the presence of an intercellular junction disruption agent. The method further includes the step of evaluating whether or not the candidate agent inhibited the disruption of the intercellular junctions by the intercellular junction disruption agent. Compositions and methods are further provided using these discovered intercellular junction disruption inhibiting agents.

Effective amounts of the compositions of the invention are administered to subjects in need of such treatment. Effective amounts are those amounts which will result in a desired improvement in the condition or symptoms of the condition, e.g., for cancer this is a reduction in cellular proliferation or metastasis, while for neurodegenerative disease or damage this is the regeneration of nerve cells, the prolonged survival of nerve cells, the migration of nerve cells or the restoration of nerve function. Such amounts can be determined with no more than routine experimentation.

It is believed that doses ranging from 1 nanogram/kilogram to 100 milligrams/kilogram, depending upon the mode of administration, will be effective. In some embodiments the level of administration is between 3 micrograms to 14 milligrams per 4 square centimeter area of cells. In one such embodiment it is heparin sodium that is administered at this level in powder or particulate form. The absolute amount will depend upon a variety of factors (including whether the administration is in conjunction with other methods of treatment, the number of doses and individual patient parameters including age, physical condition, size and weight) and can be determined with routine experimentation. It is preferred generally that a maximum dose be used, that is, the highest safe dose according to sound medical judgment. The mode of administration may be any medically acceptable mode including oral, ocular, topical, transdermal, rectal, nasal, subcutaneous, intravenous, etc. or via administration to a mucous membrane. In some embodiments the mode of administration is topical administration. In one embodiment the administration is via the internal carotid artery.

In general, when administered for therapeutic purposes, the formulations of the invention are applied in pharmaceutically acceptable solutions. Such preparations may routinely contain pharmaceutically acceptable concentrations of salt, buffering agents, preservatives, compatible carriers, adjuvants, and optionally other therapeutic ingredients.

The compositions of the invention may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); parabens (0.01-0.25% W/V) and thimerosal (0.004-0.02% W/V).

The present invention provides pharmaceutical compositions, for medical use, which comprise the polysaccharides provided and/or the polysaccharide-degrading enzymes together with one or more pharmaceutically acceptable carriers and optionally other therapeutic ingredients. The pharmaceutical compositions can also, in some embodiments, include one or more biologically active molecules. The term "pharmaceutically-acceptable carrier" as used herein, and described more fully below, means one or more compatible solid or liquid filler, dilutants or encapsulating substances which are suitable for administration to a human or other animal. In the present invention, the term "carrier" denotes an organic or inorganic ingredient, natural or synthetic, with which the active ingredient is combined to facilitate the application. The components of the pharmaceutical compositions also are capable of being commingled with each other, in a manner such that there is no interaction which would substantially impair the desired pharmaceutical efficiency.

The compositions will be provided in different vessels, vehicles or formulations depending upon the disorder and mode of administration. For example, and as described in greater detail herein, for oral application, the compounds can be administered as sublingual tablets, gums, mouth washes, toothpaste, candy, gels, films, etc.; for ocular application, as eye drops in eye droppers, eye ointments, eye gels, eye packs, as a coating on a contact lens or an intraocular lens, in contacts lens storage or cleansing solutions, etc.; for topical application, as lotions, ointments, gels, creams, sprays, tissues, swabs, wipes, etc.; for vaginal or rectal application, as an ointment, a tampon, a suppository, a mucoadhesive formulation, etc.

Compositions can be administered to the eye in various physical forms including but not limited to a liquid solution, an ophthalmic ointment or gel, or eye pack such as a cotton pledget. Liquid solutions are conveniently administered with the aid of an eye dropper and may be provided in an eye dropper bottle.

An eye dropper bottle is a container including an eye dropper which is used to remove liquid from the container. It can be glass or plastic, and may be of varying size depending upon the volume of liquid and its shelf life. Solutions that do not contain preservatives, such as ophthalmic preservatives, tend to have a shorter shelf life and thus are generally prepared in smaller volumes. Thus, in some important embodiments, the compositions are provided in eye dropper bottles that contain at a maximum, volumes on the order of 0.5 ml, or volumes on the order of 5.0 ml. These latter embodiments correspond to single use, or single week units, and optionally they do not contain ophthalmic preservatives. A plurality of such small volume bottles (e.g., vials prepared by the blow-fill-seal method) can be provided in a kit, that can optionally comprise an outer housing such as a box or bag, or a backing such as a cardboard or plastic backing. The kit can contain instructions for use of the composition.

The compositions can be formulated as ocular gels or ointments, such as those known in the art.

Compositions intended for ocular administration may contain other agents that have been described for ocular solutions, gels, etc.

In some embodiments involving ocular administration, the composition may be treated in order to eliminate color (thus rendering the solution clear and colorless). Alternatively, it may be desirable to add or change the color of the composition, particularly if color is used to confirm delivery of the composition to the eye.

In some embodiments, the ocular compositions do not contain preservatives, and rather are sterile filtered (e.g., through a 0.22 μm filter) and packaged as single use amounts. Thus, in some instances, the compositions of the invention are prepared and/or packaged in unit of use amounts. A unit of use amount may be that amount that is required for one administration, or administrations for one day, one week, one month, or longer. Preferably, a unit of unit amount will be that amount required for either one administration or for at most several days (but less than a week) of administration. Unit of use packaging is useful for preventing contamination of solutions, as it reduces the number of times an individual must contact the solution.

Ophthalmic formulations can take the form of liquids such as solutions, emulsions, dispersions, and semisolids such as gels and ointments.

Ophthalmic formulations may or may not contain ophthalmic preservatives. Ophthalmic preservatives are known in the art. Generally, such preservatives are antibiotics, as bacterial infections are one of the most common side effects of administering agents to the eye. Examples of ophthalmic preservatives include organic mercurials (e.g., phenylmercuric nitrate, phenylmercuric acetate, phenylmercuric borate, Thimerosal (Merthiolate®, Lilly)); quaternary ammonium compounds (e.g., benzalkonium chloride), benzethonium chloride, cetyl pyridinium chloride, polyquaternium-1 (POLYQUAD)); parahydroxybenzoic acid esters; and substituted alcohols and phenols (e.g., chlorobutanol, chlorobutanol/phenylethyl alcohol). Other suitable preservatives include methyl paraben and propyl paraben.

The various formulations provided herein may also be sterilized by filtering or heating, as is known in the art.

Ophthalmic formulations can further include isotonicity agents, buffering agents, preservatives (as discussed above), diluents, stabilizers, chelating agents, thickeners, etc. Examples of isotonicity agents include sodium chloride, boric acid, soidum citrate, etc. Examples of buffering agents include borate buffer, phosphate buffer, etc. The pH of ophthalmic formulations should be maintained in the range of 5-8. Examples of diluents include distilled or sterilized water or physiological saline (for aqueous formulations), and vegetable oils, liquid paraffin, mineral oil, propylene glycol, and p-octyldodecanol (for non-aqueous formulations). Examples of stabilizers include sodium sulfite and propylene glycol. An example of a suitable chelating agent is sodium EDTA. Examples of thickeners include glycerol, carboxymethylcellulose, and carboxyvinyl polymer.

A variety of other administration routes are also available. The particular mode selected will depend, of course, upon the particular active agent(s) selected, the desired results, the particular condition being treated and the dosage required for therapeutic efficacy. The methods of this invention, generally speaking, may be practiced using any mode of administration that is medically acceptable, meaning any mode that produces effective levels of intercellular junction disruption without causing clinically unacceptable adverse effects. One mode of administration is the parenteral route. The term "parenteral" includes subcutaneous injections, intravenous, intramuscular, intraperitoneal, intrasternal injection or infusion techniques. Other modes of administration include oral, mucosal, rectal, vaginal, sublingual, intranasal, intratracheal, inhalation, ocular, transdermal, etc. In some embodiments the administration of the compositions does not occur via the pulmonary route.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

One suitable oral form is a sublingual tablet. A sublingual tablet delivers the composition to the sublingual mucosa. As used herein, "tablet" refers to pharmaceutical dosage forms prepared by compressing or molding. Sublingual tablets are small and flat, for placement under the tongue and designed for rapid, almost instantaneous disintegration and release the composition to the sublingual mucosa. The term "disintegration" means breaking apart. Preferably, the sublingual tablets of the present invention disintegrate, to release the composition, within five minutes and, more preferably, within a two minute period of time. T Oral formulations can also be in liquid form. The liquid can be administered as a spray or drops to the entire oral cavity including to select regions such as the sublingual area. The sprays and drops of the present invention can be administered by means of standard spray bottles or dropper bottles adapted for oral or sublingual administration. The liquid formulation is preferably held in a spray bottle, fine nebulizer, or aerosol mist container, for ease of administration to the oral cavity. Liquid formulations may be held in a dropper or spray bottle calibrated to deliver a predetermined amount of the composition to the oral cavity. Bottles with calibrated sprays or droppers are known in the art. Such formulations can also be used in nasal administration.

The compositions of the invention can also be formulated as oral gels. As an example, the composition may be administered in a mucosally adherent, non-water soluble gel. The gel is made from at least one water-insoluble alkyl cellulose or hydroxyalkyl cellulose, a volatile nonaqueous solvent, and the composition. Although a bioadhesive polymer may be added, it is not essential. Once the gel is contacted to a mucosal surface, it forms an adhesive film due primarily to the evaporation of the volatile or non-aqueous solvent. The ability of the gel to remain at a mucosal surface is related to its filmy consistency and the presence of non-soluble components. The gel can be applied to the mucosal surface by spraying, dipping, or direct application by finger or swab.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Medical devices for the inhalation of therapeutics are known in the art. In some embodiments the medical device is an inhaler. In other embodiments the medical device is a metered dose inhaler, diskhaler, Turbuhaler, diskus or a spacer. In certain of these embodiments the inhaler is a Spinhaler (Rhone-Poulenc Rorer, West Malling, Kent). Other medical devices are known in the art and include the following technologies Inhale/Pfizer, Mannkind/Glaxo and Advanced Inhalation Research/Alkermes.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. In some embodiments the compounds provided are administered by infusion pump. In some of these embodiments the compounds are administered by infusion pump to be delivered to the blood-brain barrier. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990 and Langer and Tirrell, Nature, Apr. 1, 2004; 428(6982): 487-92, which are incorporated herein by reference.

The compositions may conveniently be presented in unit dosage form and may be prepared by any of the methods well known in the art of pharmacy.

In some embodiments the composition that is administered is in powder or particulate form rather than as a solution. In some embodiments the compositions that is administered includes sodium heparin in powder or particulate form. Examples of particulate forms contemplated as part of the invention in some embodiments are provided in U.S. patent application Ser. No. 09/982,548, filed Oct. 18, 2001, which is hereby incorporated by reference in its entirety. In other embodiments the compositions are administered in aerosol form. In other embodiments the method of administration includes the use of a bandage, slow release patch, engineered or biodegradable scaffold, slow release polymer, tablet or capsule.

In other embodiments the intercellular junction disruption agent, depending on the intercellular junction disruption agent, is administered via a route that is not normally associated with administering the intercellular junction disruption agent for therapeutic purposes. In some embodiments the intercellular junction disruption agent is not administered via a pulmonary route. In other embodiments the intercellular junction disruption agent is not administered via a gastrointestinal and/or oral route. In still other embodiments the intercellular junction disruption agent is not administered intravenously and/or subcutaneously. In yet other embodiments the intercellular junction disruption agent is not administered transdermally.

Other delivery systems can include time-release, delayed release or sustained release delivery systems. Such systems can avoid repeated administrations of the compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775 (Kent); 4,667,014 (Nestor et al.); and 4,748,034 and 5,239,660 (Leonard) and (b) diffusional systems in which an active component permeates at a controlled rate through a polymer, found in U.S. Pat. Nos. 3,832,253 (Higuchi et al.) and 3,854,480 (Zaffaroni). In addition, a pump-based hardware delivery system can be used, some of which are adapted for implantation.

Controlled release can also be achieved with appropriate excipient materials that are biocompatible and biodegradable. These polymeric materials which effect slow release may be any suitable polymeric material for generating particles, including, but not limited to, nonbioerodable/non-biodegradable and bioerodable/biodegradable polymers. Such polymers have been described in great detail in the prior art. They include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulfate sodium salt, poly(methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene, polyvinylpryrrolidone, hyaluronic acid, and chondroitin sulfate. In one embodiment the slow release polymer is a block copolymer, such as poly(ethylene glycol) (PEG)/poly(lactic-co-glycolic acid) (PLGA) block copolymer.

Examples of preferred non-biodegradable polymers include ethylene vinyl acetate, poly(meth)acrylic acid, polyamides, copolymers and mixtures thereof.

Examples of preferred biodegradable polymers include synthetic polymers such as polymers of lactic acid and glycolic acid, polyanhydrides, poly(ortho)esters, polyurethanes, poly(butic acid), poly(valeric acid), poly(caprolactone), poly(hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. The most preferred polymers are polyesters, polyanhydrides, polystyrenes and blends thereof.

In another embodiment slow release is accomplished with the use of polyanhydride wafers.

The compositions can be administered locally or the compositions can further include a targeting molecule. The targeting molecule can be attached to the polysaccharide and/or the polysaccharide-degrading enzyme and/or the biologically active molecule or some combination thereof. A targeting molecule is any molecule or compound which is specific for a particular cell or tissue and which can be used to direct the agents provided herein to a particular cell or tissue. Targeting molecules can be any molecule that is differentially present on a particular cell or in a particular tissue. These molecules can be proteins expressed on the cell surface. In one embodiment the targeting molecule targets a particular cell barrier. The cells/cell barrier can be any cells/cell barrier as provided herein. The targeting molecules can be any molecule that preferentially targets a particular molecule associated with a particular cell/cell barrier. In one embodiment the cell barrier is the blood-brain barrier. In another embodiment the targeting molecule is an antibody (e.g., a monoclonal antibody (mAb) to a receptor present on the blood-brain barrier). In one embodiment the targeting molecule is an antibody, such as monoclonal antibody OX26, to transferrin receptor (present in the blood-brain barrier as well as the liver in higher amounts than in other tissues). In another embodiment the targeting molecule is a monoclonal antibody to PGP1 (P-glycoprotein 1).

Targeting molecules can in some embodiments be used to target disease markers. In one embodiment the targeting molecule is a molecule which specifically interacts with a cancer cell or a tumor. For instance, the targeting molecule may be a protein (e.g., an antibody) or other type of molecule that recognizes and specifically interacts with a tumor antigen.

Tumor-antigens include Melan-A/MART-1, Dipeptidyl peptidase IV (DPPIV), adenosine deaminase-binding protein (ADAbp), cyclophilin b, Colorectal associated antigen (CRC)—C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100$^{Pmel117}$, PRAME, NY-ESO-1, brain glycogen phosphorylase, SSX-1, SSX-2 (HOM-MEL-40), SSX-1, SSX-4, SSX-5, SCP-1, CT-7, cdc27, adenomatous polyposis coli protein (APC), fodrin, P1A, Connexin 37, Ig-idiotype, p15, gp75, GM2 and GD2 gangliosides, viral products such as human papilloma virus proteins, Smad family of tumor antigens, lmp-1, EBV-encoded nuclear antigen (EBNA)-1, and c-erbB-2.

Some aspects of the invention also encompass kits. The kits of the invention include one or more polysaccharides and/or one or more polysaccharide-degrading enzymes (the intercellular junction disruption agent). The kits can further include one or more biologically active molecules, administration devices (e.g., an inhalation apparatus) and/or instructions for use. An inhalation apparatus, as used herein, is any device for administering a dry aerosol. This type of equipment is well known in the art and has been described in detail, such as that description found in Remington: The Science and Practice of Pharmacy, 19$^{th}$ Edition, 1995, Mac Publishing Company, Easton, Pa., pages 1676-1692. Many U.S. patents also describe inhalation devices, such as U.S. Pat. No. 6,116,237. The kits provided can also include an intercellular junction disruption inhibiting agent and/or a detection system. Detection systems can be used to determine the amount of any or all of the agents administered in the blood. Detection systems can be invasive or non-invasive. An example of an invasive detection system is one which involves the removal of a blood sample and can further involve an assay such as an enzymatic assay or a binding assay to detect levels in the blood. A non-invasive type of detection system is one which can detect the levels of the agent in the blood without having to break the skin barrier. These types of non-invasive systems include, for instance, a monitor which can be placed on the surface of the skin, e.g., in the form of a ring or patch, and which can detect the level of circulating agents. One method for detection may be based on the presence of fluorescence in the agent which is administered. Thus, if a fluorescently labeled agent is administered and the detection system is non-invasive, it can be a system which detects fluorescence. This is particularly useful in the situation when the patient is self-administering and needs to know the blood concentration or an estimate thereof in order to avoid side effects or to determine when another dose is required.

A subject is any human or non-human vertebrate, e.g., dog, cat, horse, cow, monkey, pig, mouse, rat.

As used herein, disease and disorder are used interchangeably.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Methods and Materials

Cell Culture

Calu-3 human lung adenocarcinoma epithelial cells, caco-2 human adenocarcinoma colon epithelial cells and MCF-7 human mammary gland adenocarcinoma epithelial cells were purchased from American Type Culture Collection (ATCC). 16HBE14O-human virally transformed bronchial epithelial cells were a generous gift from Dr. Gruenert (California Pacific Medical Center Research Institute, San Francisco, Calif.). Cells were grown in Eagle's Minimal Essential medium with 2 mM L-glutamine (GIBCO, Invitrogen, Carlsbad, Calif.) adjusted to contain 1.0 mM sodium pyruvate, 0.1 mM nonessential amino acids and 1.5 g/L sodium bicarbonate with 10% fetal bovine serum (FBS) and supplemented with 100 µg/mL penicillin G (Sigma, St. Louis, Mo.) and 100 µg/mL streptomycin sulfate (Sigma). The cells were plated in 75 $cm^2$ cell culture flasks and subcultured when 80%~90% confluency was reached using a 0.25% trypsin-ethylene diamine tetra acetic acid (EDTA) solution (Sigma). The 16HBE14O-cells were plated on flasks coated with fibronectin. The culture medium was changed every 2-3 days. The cells were passaged at a split ratio of 1:4.

Antibodies

The primary antibodies used were rabbit anti-human ZO-1 purchased from Zymed Labs (South San Francisco, Calif.), mouse anti-human syndecan-1 was purchased from Serotec (Raleigh, N.C.) and mouse anti-human syndecan-4 from SantaCruz Biotechnology, Inc. (Santa Cruz, Calif.) and phospho tyrosine (PY99) and Phospho FAK antibodies horse radish peroxidase (HRP) purchased from SantaCruz Biotechnology, Inc. Secondary antibodies used were goat anti-mouse HRP, goat anti-rabbit HRP purchased from SantaCruz Biotechnology, Inc and goat anti-rabbit (Texas Red) and Texas Red phalloidin purchased from Molecular Probes (Eugene, Oreg.).

Enzyme and Unfractionated Heparin (UFH) Sodium Addition

Heparinase III (hep III) was made as described previously (Godavarti R et al., 1996); heparinase I (hep I) was a generous gift from Momenta pharmaceuticals (Cambridge, Mass.); chondroitinase ABC (C-ABC) lyase was purchased from Seikagaku (East Falmouth, Mass.). Hep III was added to the apical side of the cells at a concentration of 10 µg/mL; hep I was added at a concentration of 6 µg/mL, and C-ABC was added at 50 µU/mL. The concentration of ethylene glycol tetra acetic acid (EGTA) (Sigma) used was 5 mM. All the enzymes and the EGTA were made up in serum free Eagle's Minimal Essential medium with 2 mM L-glutamine. Heparin solution was made up to a concentration of 15 mM in serum free media and added to the apical side of the cells after removing the cell medium. Ardeparin sodium and ardeparin calcium powder were added to cells at 6 mg/well, and ardeparin solution was made up to a final concentration of 18 mM.

Immunoflourescence and Confocal Microscopy

Cells grown on glass coverslips were fixed with 10% buffered formalin for 10 min. Cells were then permeabilized with 0.5% Triton-100 (Sigma) in Tris Buffer Saline with 1% Tween-20 (TBST) for 15 min. at room temperature. Nonspecific antibody binding was blocked with 0.1% bovine serum albumin (BSA) for 30 min. at room temperature. The cells were incubated with primary antibody at room temperature for 4 hours and washed 3 times with PBS. The cells were then incubated in the appropriate secondary antibody for 1 hour in the dark at room temperature and washed 3 times with PBS. Coverslips were mounted onto glass slides with SlowFade light antifade kit (Molecular Probes) and viewed under confocal microscopy (Zeiss LSM510 laser confocal scanning microscopy, Carl Zeiss, Jena, Germany).

Animal Experiments

Male Sprauge-Dawley rats (250-300 g; Charles River, Wilmington, Mass.) were used in UFH powder pulmonary delivery experiments. Heparin powder was mixed with azure A (Aldrich, St. Louis, Mo.) for the visual distribution experiment. FITC (fluorescein)-heparin powder was used in the immunohistology study. Rats were anesthetized with ketamine (80 mg/kg) and xylazine (10 mg/kg) by means of i.p. injection. The trachea was exposed and a small cut was made for insertion of the trachea tube to facilitate delivery of the polymer.

Immunoprecipitation and Western Blot Analysis

Cells were lysed for 30 min. with ice-cold RIPA (radioimmunoprecipitation) lysis buffer. The lysate was clarified by centrifugation at 14000 r.p.m. for 15 min. at 4° C. The clarified lysate was then incubated with Protein-G agarose beads for 1 hour, and equal amounts of proteins in the supernatant was then incubated for 2 hours with primary antibody polyclonal rabbit anti-ZO-1 (4 µg total antibody) (Zymed). The lysate was subsequently incubated for another 4 hours with Protein-G agarose beads (50 µL bed volume), following which the beads were isolated by configuration, washed repeatedly in RIPA buffer, and solubilised in sample buffer and boiled for 10 min.

Cells lysates or immunoprecipitates in sodium dodecyl sulfate (SDS) sample buffer were separated by 4-12% gradient gel (Invitrogen) and transferred onto nitrocellulose membranes (Amersham, Piscataway, N.J.). The membrane was then blocked with either 5% nonfat milk in Tris-buffered saline with 0.1% Tween 20 (for Western Blot) or Blotto (for immunoprecipitation) overnight and incubated with primary antibodies for 3 hours at room temperature. The membrane was then incubated in appropriate goat anti-rabbit HRP or goat anti-mouse HRP secondary antibody for 1 hour at room temperature. The secondary antibody was detected using a chemiluminescent reaction quantified using Kodak Gel Imaging System (Eastman Kodak, New Haven, Conn.).

Dot Immunoassay

Specificity and quantification of the dot immunoassay for shed syndecan-1 and -4 ectodomains has been previously described in detail (Subramanian et al., 1997). In brief, the conditioned media were diluted in buffer A (0.15 M NaCl buffered to pH 4.5 with 50 mM sodium acetate and with 0.1% Triton X-100) and applied to catonic polyvinylidine diflouride-based membranes (Immobilin-N) (Millipore, Bedford, Mass.) under mild vacuum in an immunodot apparatus (V&P Scientific, San Diego, Calif.). By acidifying the samples in buffer A, only highly anionic molecules in the conditioned media, such as proteoglycans, are retained by the cationic Immobilon-N membrane, while most proteins are cationic at this pH and pass through the membranes. The membranes were washed twice with buffer, blocked for 1 hour with Blotto (3% Carnation instant nonfat dry milk, 0.15 M NaCl in 10 mM Tris, pH 7.4), incubated with primary antibodies, washed twice with tris buffered saline (TBS) containing 0.1% Tween 20, and incubated with the appropriate HRP-conjugated anti-mouse or anti-rabbit IgG, respectively. All antibodies were diluted in Blotto with 0.1% Tween 20.

Detection was by the ECL system (Amersham) as described by the manufacturer. Results were quantified by scanning the exposed membrane with a Kodak Image Station.

Unfractionated Heparin Powder is Taken Up into the Lungs and Trachea of Mice

FITC-Heparin powder was delivered to anesthesized mice using an insufflator (Penn Century, Philadelphia, Pa.) connected to the trachea tube. At defined time intervals, lung along with trachea were dissected. For visual distribution, photos were taken using a Nikon digital camera. For immunohistology, lung and trachea tissues were embedded in OCT (optimal cutting temperature compound) (Electron Microscopy Sciences, Hatfield, Pa.) and immediately put into liquid nitrogen. The tissues were cut by cryosection and were stained for the tight junction protein ZO-1. Briefly, the tissue section was incubated in primary antibody rabbit anti-ZO-1 Texas Red (1:200) for 4 hours at room temperature and were then incubated in the corresponding secondary antibody Goat anti-rabbit (1:500) for an hour at room temperature. The analysis of the distribution of the labeled heparin and ZO-1 was done using confocal microscopy (Zeiss LSM510 laser confocal scanning microscopy, Carl Zeiss) (FIGS. 1A and 1B).

Ardeparin Sodium Powder (Not Solution) is Transported through Calu-3 Human Lung Adenocarcinoma Epithelial Cells; Ardeparin Calcium is Not Cells were seeded on transwell inserts with a mean pore size of 0.4 µm and a growing surface area of 0.33 cm$^2$ (Costar, Corning Inc., Acton, Mass.) at a density of 3×10$^5$ cells/cm$^2$ and were cultivated for 8 to 12 days. Transport experiments were carried out at 37° C. with 0.5 mL medium in basolateral chamber and 0.2 mL of test solution applied apically to the insert. For the powder delivery experiment, the cell medium was removed and the cells were washed with serum free medium. Ardeparin sodium and ardeparin calcium powder were then delivered onto the apical layer of the cells at a final concentration of 6 mg/well using the insufflator. Ardeparin sodium solution, made up in serum free media, was added to the cells to a final concentration of 18 mM (21.6 mg/well). The insert was changed to a new well with 0.5 mL fresh medium at predetermined time intervals, and the medium left in the previous well was collected as the sample for drug content test. Each experiment was performed in triplicate. The results are shown as a function of cumulative transport vs time (FIG. 2A). The solid line shows the transport of ardeparin sodium powder with time, and the dotted line shows the transport of ardeparin calcium powder with time. In FIG. 2B, the solid line shows the transport of ardeparin sodium powder, and the dotted line shows the transport of ardeparin sodium solution. All values shown are means+/−S.D. of triplicate Transwell filters.

The Fall in TEER in Calu-3 Human Lung Adenocarcinoma Epithelial Cells Caused by Unfractionated Heparin Sodium is Concentration-Dependent Cells were seeded on transwell inserts with a mean pore size of 0.4 µm and a growing surface area of 0.33 cm$^2$ (Costar, Corning Inc.) at a density of 3×10$^5$ cells/cm$^2$ and were cultivated for 8 to 12 days. The integrity of the monolayer was checked during cell growth after seeding as well as in the beginning and at the end of each transport experiment by measuring Trans Epithelial Electrical Resistance (TEER) using the Millicell-ERS Epithelial Voltmeter (Millipore). The total TEER (cell monolayer+insert) was subtracted from background TEER (insert) to yield the monolayer resistance and multiplied with the area of the insert as shown in Equation 1 (TEER=(Rtotal−Rblank)×A ($\Omega.cm^2$)).

FIG. 3 shows the fall in TEER in calu-3 cells after addition of UFH. The sugar was added to the apical side of the cells at various concentrations 1 mM (open circles), 2.5 mM (solid circles), 5 mM (open triangle), 10 mM (solid square) and 15 mM (*). TEER measurements were taken at the different times indicated in the graph. The values shown are the means+/−S.D. of triplicate Transwell filters.

Modulators of Cell Surface HSGAGs Cause Disruption of Tight Junctions in 16HBE14O-Human Virally Transformed Bronchial Epithelial Cells 16HBE14O-cells were grown to confluency on fibronectin coated coverslips for 4 to 5 days after seeding. The cells were then incubated with hep III, hep I, C-ABC and EGTA made up to the final concentration described above for 20 min. at 37° C. Using the primary rabbit anti-ZO-1 antibody and the secondary goat anti-rabbit Texas Red antibody, the cells were analyzed by the immunofluorescence and confocal microscopy technique discussed above. The results of the experiment are shown in FIG. 4. The figure shows that hep III, hep I, C-ABC and EGTA cause different amounts of disruption of the tight junctions in the 16HBE14O-cells. Localization of the tight junction protein in untreated cells is also shown as a control.

Visual Investigation of the Tight Junction and Actin Filament Disruption after Addition of UFH Powder to Calu-3 Human Lung Adenocarcinoma Epithelial Cells Calu-3 cells were seeded on gelatin coated coverslips and were allowed to grow for about 4 to 5 days to about 80% confluency. UFH powder was added to the apical side of the cells using an insufflator to ensure homogenous distribution of the powder on the coverslip. Using the primary rabbit anti-ZO-1 antibody, the FITC phalloidin (used as suggested by the vendor) and the secondary goat anti-rabbit Texas Red antibody, the cells were analyzed by the immunofluorescence and confocal microscopy technique discussed above. The results are shown in FIG. 6. Actin filaments (in green) and ZO-1 (in red) are disrupted after addition of UFH. The pattern of the filaments and ZO-1 in untreated cells is shown as a control.

Increase in Phosphorylation of ZO-1 in Calu-3 Human Lung Adenocarcinoma Epithelial Cells upon Addition of UFH Powder and Solution Calu-3 cells were seeded in 6 well plates coated with gelatin and were allowed to grow for 4 to 5 days to 80% confluency. A confluent monolayer of cells was treated with UFH powder and solution for 10 min. and 30 min. The cells were lysed using RIPA buffer and were immunoprecipitated with primary antibody against ZO-1 (rabbit anti-ZO-1) followed by analysis by SDS PAGE and Western blotting with antibodies against phospho tyrosine (mouse anti-p-Tyr HRP). The membrane was then developed and analyzed, and the results are summarized in FIG. 7. ZO-1 phosphorylation levels of untreated calu-3 cells are also shown as a control.

Addition of UFH Powder Causes a Fall in the Intracellular Calcium Levels $Ca^{2+}$ probe in living cells was conducted by using calcium indicator dye Fluo 4-AM (Molecular Probes). Fluo 4-AM was loaded onto calu-3 cells grown on a glass coverslip chamber at a concentration of 4 µm for 1 hour to saturate Fluo 4-AM with $Ca^{2+}$ to obtain maximal fluorescence. The cells were washed 3 times with PBS to remove extra Fluo 4-AM, and the cells were ready for confocal microscopy. Images were taken 0-9 min. after treatment of the cells with UFH powder and solution (20 mM) at an interval of 1 min. at 494 nm (excitation) and 516 nm (emission). FIG. 8 shows a slight fall in intracellular calcium levels after the solution addition and a marked decrease in intracellular calcium levels after UFH powder addition to calu-3 cells. This suggests that the heparin powder could be chelating extracellular calcium and hence causing an imbalance between intra and extra cellular calcium levels implicating the involvement of one or many of the proteins involved in the calcium signaling pathway.

Addition of Modulators of Cell Surface HSGAGs Causes Shedding of the Cell Surface Proteoglycan Syndecan-1 but Has No Effect on the Shedding of Syndecan-4 in 16HBE14O-Human Virally Transformed Bronchial Epithelial Cells 16HBE14O-cells were grown to about 80% confluency in 6 well plates. The cells were then incubated with 800 µL of hep III, hep I and C-ABC made up to the final concentrations described above. After incubation, the cells were examined for survival, and the conditioned media were harvested. To evaluate the changes in cell number, the cells were trypsinized and counted with a coulter-counter after incubation. The 800 µL was divided into 2 equal portions (duplicates) for the Dot Blot analysis. The Dot Immunoassay was done as explained above. The membranes were then incubated in mouse anti-syndecan-1 and in the appropriate secondary antibody and were developed and analyzed as described above. The experiment was repeated as such with the mouse anti-syndecan-4 antibody to study the shedding of syndecan-4. FIG. 9A shows syndecan-1 shedding after the different treatments. An increase in the intensity of the dot signifies an increase in shedding. FIG. 9B shows the effect of the treatments on syndecan-4 shedding. In both of the figures, the endogenous shedding of the proteogylcans is shown in untreated cells as a control.

Modulators of HSGAGs Cause Changes in Phosphorylation of FAK in 16HBE14O-Human Virally Transformed Bronchial Epithelial Cells 16HBE14O-cells were grown to about 80% confluency in 6 well plates. The cells were then incubated with 800 µL of hep III, hep I and C-ABC made up to the final concentrations discussed above. The cells were lysed using Western Running Buffer. To normalize the levels of protein in the different wells, the lysate was separated using SDS PAGE. The membrane was blocked with 5% non-fat milk and then incubated for 2 hours at room temperature with antibody against beta-actin (goat anti-beta actin) and for one hour in the dark with the secondary rabbit anti-goat HRP antibody. After normalizing the levels of protein in the different wells, the lysate was separated using SDS PAGE, and using antibodies against p-FAK the techniques described above for Western Blotting were performed. The membrane was then incubated with antibodies against total FAK to compare the ratio of p-FAK to total FAK after the different treatments. Analysis was done using the Kodak Image Station. FIG. 10 summarizes the results of the experiments. All values were normalized with respect to the untreated cells.

REFERENCES

1. Arribas, J., Coodly, L., Vollmer, P., Kishimoto, T. K., Rose-John, S., Massagué, J. 1996. Diverse cell surface protein ectodomains are shed by a system sensitive to metalloproteinase inhibitors. *J. Biol. Chem.* 271:11376-11382.
2. Asundi V K, Erdman R, Stahl R C, Carey D J. Matrix metalloproteinase-dependent shedding of syndecan-3, a transmembrane heparan sulfate proteoglycan, in Schwann cells. J Neurosci Res. Sep. 1, 2003; 73(5):593-602.
3. Atkinson K J, Rao R K. Role of protein tyrosine phosphorylation in acetaldehyde-induced disruption of epithelial tight junctions. Am J Physiol Gastrointest Liver Physiol. June 2001; 280(6): G1280-8.
4. Beauvais D M, Rapraeger A C., Syndecan-1-mediated cell spreading requires signaling by alphavbeta3 integrins in human breast carcinoma cells. Exp Cell Res. Jun. 10, 2003; 286(2): 219-32.
5. Bernfield M, Gotte M, Park P W, Reizes O, Fitzgerald M L, Lincecum J, Zako M., Functions of cell surface heparan sulfate proteoglycans. *Annu Rev Biochem.* 1999; 68:729-77. Review.
6. E Willott, M S Balda, A S Fanning, B Jameson, C V Itallie, and J M Anderson The Tight Junction Protein ZO-1 is Homologous to the Drosophila Discs—Large Tumor Suppressor Protein of Septate Junctions; Proc Natl Acad Sci USA. Aug. 15, 1993; 90 (16): 7834-7838.
7. Fitzgerald M L, Wang Z, Park P W, Murphy G, Bernfield M. Shedding of syndecan-1 and -4 ectodomains is regulated by multiple signaling pathways and mediated by a TIMP-3-sensitive metalloproteinase. *J Cell Biol. Feb.* 21, 2000; 148(4): 811-24.
8. G. T. Knipp, N. F. Ho, C. L. Barsuhn, R. T. Borchardt, Paracellular diffusion in Caco-2 cell monolayers: Effect of perturbation on the transport of hydrophilic compounds that vary in charge and size. *J. Pharm. Sci.* 86, 1105-1110 (1997).
9. Garibaldi M Kanig J L. Oral ther. Pharmacol, 1.440 (1965)
10. Godavarti R, Davis M, Venkatraman G, Cooney C, langer R, Sasisekharan R Heparinase III from *Flavobacterium heparinum*: cloning and recombinant expression in *Escherichia coli. Biochem Biophys Res Commun. Aug.* 23, 1996b; 225(3): 751-8.
11. Godavarti R, Sasisekharan R, A comparative analysis of the primary sequences and characteristics of heparinases I, II, and III from *Flavobacterium heparinum. Biochem Biophys Res Commun. Dec.* 24, 1996a; 229(3): 770-7.
12. Godavarti R, Sasisekharan R, Heparinase I from *Flavobacterium heparinum*. Role of positive charge in enzymatic activity. *J Biol Chem. Jan.* 2, 1998; 273(1): 248-55.
13. Haraj N. S., Antonetti D. A., Regulation of tight junction and loss of barrier function in pathophysiology, Int J of Biochem and cellbiol., 36(7): 1206-1237 (2004)
14. Hooper, N. M., Turner, A. J. 1999. Membrane protein secretases. *Biochem. Soc. Trans* 27:211-257.
15. J Schlondorff and C P Blobel, Metalloprotease-disintegrins: modular proteins capable of promoting cell-cell interactions and triggering signals by protein-ectodomain shedding; Journal of Cell Science 1999, Vol 112, Issue 21 3603-3617.
16. Kiessling, L. L., Gordon, E. J. 1998. Transforming the cell surface through proteolysis. *Chem. Biol* 5:R49-R62.
17. L. Gonzalez-Mariscal, A. Betanzos, P. Nava, B. E. Jaramillo, Tight junction proteins. *Prog. Biophys. Mol. Biol.* 81, 1-44 (2003).
18. Lin P, Sinha U, Betz A., Antithrombin binding of low molecular weight heparins and inhibition of factor Xa. Biochim Biophys Acta. Apr. 3, 2001; 1526(1): 105-13.
19. M. G. Farquhar and G. E. Palade. *J. Cell Biol.* 17 (1963), pp. 375-412.
20. Madara J L, Pappenheimer J R., Structural basis for physiological regulation of paracellular pathways in intestinal epithelia, J Membr Biol. 1987; 100(2): 149-64.

21. Majerus P W, Brose G J, Miletich J P, Tollefsen P M. Anticoagulant, thrombolytic, and antiplatelet drugs. In: Hardman J G, Limbrid L E, eds., Goodman and Gilman's The pharmacological bases of therapeutics, 9th ed, New York: McGraw Hill, 1996:1341-6.
22. Masahiko Itoh, Akira Nagafuchi, Seiji Moroi, and Shoichiro Tsukita, Involvement of ZO-1 in Cadherin-based Cell Adhesion through Its Direct Binding to α Catenin and Actin Filaments; J. Cell Biol. 138 (1):181-192 1997
23. Matter K, Balda M. S., "Signaling to and from tight junctions", *Nature Reviews Molecular Cell Biology* 4, 225-237 (2003).
24. Merlos-Suarez, A., Arribas, J. 1999. Mechanisms controlling the shedding of transmembrane molecules. *Biochem. Soc. Trans* 27:243-246.
25. Park P W, Pier G B, Hinkes M T, Bernfield M. Exploitation of syndecan-1 shedding by *Pseudomonas aeruginosa* enhances virulence. *Nature*. May 3, 2001; 411(6833):98-102.
26. Park P W, Pier G B, Preston M J, Goldberger O, Fitzgerald M L, Bernfield M. Syndecan-1 shedding is enhanced by LasA, a secreted virulence factor of *Pseudomonas aeruginosa*. *J Biol Chem. Feb.* 4, 2000; 275(5): 3057-64.
27. Perrimon N. and Bernfield, M., 2000. Specificities of heparan sulphate proteoglycans in developmental processes. *Nature* 404, pp. 725-728.
28. Rosenberg R. D., Shworak, N. W., Liu, J. et al., 1997. Heparan sulfate proteoglycans of the cardiovascular system. Specific structures emerge but how is synthesis regulated? *J Clin Invest* 100 11 Suppl, pp. S67-S75.
29. Sasisekharan, R. and Venkataraman, G., 2000. Heparin and heparan sulfate: biosynthesis, structure and function. *Curr Opin Chem Biol* 4, pp. 626-631.
30. Squier C A, Johnson N W. Brit Med Bull, 31: 169 (1975).
31. Subramanian S V, Fitzgerald M L, Bernfield M. Regulated shedding of syndecan-1 and -4 ectodomains by thrombin and growth factor receptor activation. J Biol Chem. Jun. 6, 1997; 272(23): 14713-20.
32. Endo K, Takino T, Miyamori H, Kinsen H, Yoshizaki T, Furukawa M, Sato H. Cleavage of syndecan-1 by membrane type matrix metalloproteinase-1 stimulates cell migration. J Biol Chem. Oct. 17, 2003; 278(42): 40764-70.
33. Beauvais D M, Rapraeger A C. Syndecans in tumor cell adhesion and signaling. Reprod Biol Endocrinol. Jan. 7, 2004; 2(1): 3.
34. Rhodes K E, Fawcett J W. Chondroitin sulphate proteoglycans: preventing plasticity or protecting the CNS? J Anat. January 2004; 204(1): 33-48. Review.
35. Sugahara K, Kitagawa H. Heparin and heparan sulfate biosynthesis. IUBMB Life. October 2002; 54(4): 163-75. Review.
36. Minagar A, Alexander J S. Blood-brain barrier disruption in multiple sclerosis. Mult Scler. December 2003; 9(6): 540-9. Review.

U.S. patent documents cited:

| | | |
|---|---|---|
| 6686341 | February, 2004 | Bijlsma et al. |
| 6312686 | November, 2001 | Staddon et al. |
| 6610653 | September, 2000 | Backstrom et al. |
| 6252045 | June, 2001 | Anderson et al. |
| 6723700 | April, 2004 | Blaschuk et al. |

Each of the foregoing patents, patent applications and references that are recited in this application are herein incorporated in their entirety by reference. Having described the presently preferred embodiments, and in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

We claim:

1. A method for enhancing the delivery of an antimicrobial agent for treating an infection to a subject with an infection, comprising:
   administering to the subject a heparinase or a heparin-like glycosaminoglycan (HLGAG) and the antimicrobial agent, wherein the delivery of the antimicrobial agent through intercellular junctions is enhanced.

2. An antimicrobial composition, comprising:
   a heparinase or a heparin-like glycosaminoglycan (HLGAG) and an antimicrobial agent for treating an infection, wherein the heparinase or HLGAG is in an amount effective to enhance the delivery of the antimicrobial agent through intercellular junctions.

3. The composition of claim 2, wherein the composition is in a form suitable for nasal administration.

4. The method of claim 1, wherein the administration is via the nasal tract.

5. The composition of claim 3, wherein the form suitable for nasal administration is a nasal spray, nasal drop or nasal gel.

6. The composition of claim 2 or 3, wherein the infection is a viral infection, a bacterial infection or a fungal infection.

7. The method of claim 1 or 4, wherein the infection is a viral infection, a bacterial infection or a fungal infection.

8. The composition of claim 6, wherein the viral infection is caused by a *Retroviridae, Picornaviridae, Calciviridae, Togaviridae, Flaviridae, Coronoviridae, Rhabdoviradae, Filoviridae, Paramyxoviridae, Orthomyxoviridae, Bungaviridae, Arena viridae, Reoviridae, Birnaviridae, Hepadnaviridae, Parvovirida, Papovaviridae, Adenoviridae, Herpesviridae, Poxviridae* or a *Iridoviridae* virus.

9. The method of claim 7, wherein the viral infection is caused by a *Retroviridae, Picornaviridae, Calciviridae, Togaviridae, Flaviridae, Coronoviridae, Rhabdoviradae, Filoviridae, Paramyxoviridae, Orthomyxoviridae, Bungaviridae, Arena viridae, Reoviridae, Birnaviridae, Hepadnaviridae, Parvovirida, Papovaviridae, Adenoviridae, Herpesviridae, Poxviridae* or a *Iridoviridae* virus.

10. The composition of claim 2 or 3, wherein the antimicrobial agent is an antiprotozoal, antifungal, antibacterial or antiviral agent.

11. The method of claim 1 or 4, wherein the antimicrobial agent is an antiprotozoal, antifungal, antibacterial or antiviral agent.

12. The composition of claim 2 or 3, wherein the heparin-like glycosaminoglycan is heparin.

13. The method of claim 1 or 4, wherein the heparin-like glycosaminoglycan is heparin.

14. The composition of claim 2 or 3, wherein the heparinase is heparinase I, heparinase II or heparinase III.

15. The method of claim 1 or 4, wherein the heparinase is heparinase I, heparinase II or heparinase III.

* * * * *

UNITED STATES PATENT AND TRADEMARK OFFICE
CERTIFICATE OF CORRECTION

PATENT NO. : 8,529,889 B2
APPLICATION NO. : 11/171490
DATED : September 10, 2013
INVENTOR(S) : Aarthi Chandrasekaran et al.

It is certified that error appears in the above-identified patent and that said Letters Patent is hereby corrected as shown below:

In the Specification

At column 1, lines 14-17, please delete

"Aspects of the invention may have been made using funding from National Institutes of Health Grant number GM57073. Accordingly, the Government may have rights in the invention."

and insert

--This invention was made with government support under Grant No. GM057073 awarded by the National Institutes of Health. The government has certain rights in the invention.--

Signed and Sealed this
Twenty-ninth Day of April, 2014

Michelle K. Lee
*Deputy Director of the United States Patent and Trademark Office*